(12) United States Patent
Kasai et al.

(10) Patent No.: US 8,373,016 B2
(45) Date of Patent: Feb. 12, 2013

(54) ABSORBENT MEMBER AND METHOD OF PRODUCING THE SAME

(75) Inventors: Takao Kasai, Tochigi (JP); Masahiko Niinomi, Tochigi (JP); Takuya Kouta, Tochigi (JP); Rumiko Kasahara, Tochigi (JP); Akira Noda, Tochigi (JP)

(73) Assignee: Kao Corporation, Tokyo (JP)

( * ) Notice: Subject to any disclaimer, the term of this patent is extended or adjusted under 35 U.S.C. 154(b) by 755 days.

(21) Appl. No.: 12/225,489

(22) PCT Filed: Mar. 19, 2007

(86) PCT No.: PCT/JP2007/055564
§ 371 (c)(1),
(2), (4) Date: Jan. 26, 2009

(87) PCT Pub. No.: WO2007/122938
PCT Pub. Date: Nov. 1, 2007

(65) Prior Publication Data
US 2010/0022978 A1    Jan. 28, 2010

(30) Foreign Application Priority Data

Mar. 23, 2006 (JP) ................................. 2006-081587
Nov. 17, 2006 (JP) ................................. 2006-311470
Nov. 17, 2006 (JP) ................................. 2006-311473
Nov. 17, 2006 (JP) ................................. 2006-311474

(51) Int. Cl.
*A61F 13/15* (2006.01)
(52) U.S. Cl. ..................... 604/367; 604/384; 604/385.01
(58) Field of Classification Search .................. 604/367, 604/370, 358, 380
See application file for complete search history.

(56) References Cited

U.S. PATENT DOCUMENTS

| | | | |
|---|---|---|---|
| 4,902,559 A | | 2/1990 | Eschwey et al. |
| 5,149,334 A | * | 9/1992 | Lahrman et al. ............... 604/367 |
| 5,300,565 A | * | 4/1994 | Berg et al. ..................... 525/54.2 |
| 5,611,981 A | | 3/1997 | Phillips et al. |

(Continued)

FOREIGN PATENT DOCUMENTS

| | | |
|---|---|---|
| DE | 43 16 668 A1 | 11/1994 |
| EP | 0 296 279 A2 | 12/1988 |

(Continued)

OTHER PUBLICATIONS

Japanese Decision of Refusal and Decision of Rejection of Amendment dated Apr. 12, 2011 for Application No. 2006-311471.

(Continued)

*Primary Examiner* — Susan Su
(74) *Attorney, Agent, or Firm* — Birch, Stewart, Kolasch & Birch, LLP

(57) ABSTRACT

An absorbent member (10) of the invention has a hydrophilic continuous fiber web (12) and lumpy particles of an absorbent polymer (13) held in the web (12). The absorbent polymer (13) is localized in part in a planar or thickness direction of the absorbent member (10). The continuous fibers in a region (M) in a planar direction of the web (12) where the absorbent polymer is distributed are in a state cut into a large number of staple fibers (122). A method of producing an absorbent member includes the step of spreading lumpy particles of an absorbent polymer (13) on a continuous fiber web (12) and pressing the continuous fibers in part of the web (12) onto the absorbent polymer (13) to cut the continuous fibers.

9 Claims, 26 Drawing Sheets

U.S. PATENT DOCUMENTS

| | | | |
|---|---|---|---|
| 5,700,254 A | 12/1997 | McDowall et al. | |
| 5,830,202 A * | 11/1998 | Bogdanski et al. | 604/378 |
| 5,977,429 A * | 11/1999 | Phillips et al. | 604/370 |
| 7,759,540 B2 * | 7/2010 | Litvay et al. | 604/379 |
| 2001/0051796 A1 * | 12/2001 | Noda et al. | 604/383 |
| 2003/0111163 A1 * | 6/2003 | Ko et al. | 156/181 |
| 2003/0116890 A1 * | 6/2003 | Chambers et al. | 264/518 |
| 2003/0135177 A1 * | 7/2003 | Baker | 604/368 |
| 2003/0139719 A1 * | 7/2003 | Nanaumi et al. | 604/374 |
| 2004/0204696 A1 * | 10/2004 | Chen | 604/367 |
| 2004/0204697 A1 * | 10/2004 | Litvay | 604/367 |
| 2006/0141891 A1 * | 6/2006 | Melius et al. | 442/416 |
| 2006/0184149 A1 | 8/2006 | Kasai et al. | |
| 2008/0119586 A1 | 5/2008 | Byerly et al. | |
| 2008/0167634 A1 * | 7/2008 | Kouta et al. | 604/367 |
| 2008/0262459 A1 | 10/2008 | Kamoto et al. | |
| 2009/0076473 A1 * | 3/2009 | Kasai et al. | 604/367 |

FOREIGN PATENT DOCUMENTS

| | | |
|---|---|---|
| EP | 1417946 A1 | 5/2004 |
| EP | 1 627 618 A1 | 2/2006 |
| JP | 50-30572 A | 10/1975 |
| JP | 57-160457 A | 10/1982 |
| JP | 1-292181 A | 11/1989 |
| JP | 2-4705 B2 | 1/1990 |
| JP | 2-74254 A | 3/1990 |
| JP | 4-504285 A | 7/1992 |
| JP | 5-247822 A | 9/1993 |
| JP | 5-261126 A | 10/1993 |
| JP | 7-24003 A | 1/1995 |
| JP | 7-275293 A | 10/1995 |
| JP | 9-111635 A | 4/1997 |
| JP | 2001-46434 A | 2/2001 |
| JP | 3193371 B2 | 5/2001 |
| JP | 2003-52749 A | 2/2003 |
| JP | 2004-159786 A | 6/2004 |
| JP | 2005-511918 A | 4/2005 |
| JP | 2005-334626 A | 12/2005 |
| JP | 2006-6741 A | 1/2006 |
| JP | 2006-15012 A | 1/2006 |
| JP | 2006015012 * | 1/2006 |
| JP | 2006-110329 A | 4/2006 |
| JP | 2006-152504 A | 6/2006 |
| JP | 2006-297073 A | 11/2006 |
| JP | 2006-297076 A | 11/2006 |
| JP | 2006-305326 A | 11/2006 |
| WO | WO 90/12130 A2 | 10/1990 |
| WO | WO-99/49826 A1 | 10/1999 |
| WO | WO 03/051253 A1 | 6/2003 |
| WO | WO 2006/003942 A1 | 1/2006 |

OTHER PUBLICATIONS

Extended European Search Report, dated Oct. 28, 2010, for European Application No. 07739007.8.

Japanese Notice of Rejection, dated Nov. 16, 2010, for Japanese Application No. 2006-311471.

A Partial English Language Translation for JP-57-160457-A is attached.

Notice of Rejection issued on Aug. 10, 2010 for Japanese Patent Application No. 2006-311471.

Japanese Notice of Rejection dated Aug. 2, 2011 for Japanese Application No. 2006-311470.

Japanese Notice of Rejection dated Aug. 2, 2011 for Japanese Application No. 2006-311474.

Office Action in Chinese Application No. 200780010310.X, dated Feb. 16, 2012.

\* cited by examiner

RA  RB

RA  RB

RA, RB

RA  RB

RA  RB

Fig. 13(a)
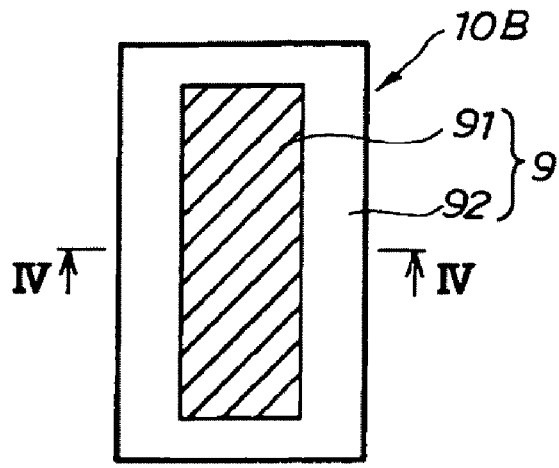
Fig. 13(b)
Fig. 14(a)
Fig. 14(b)
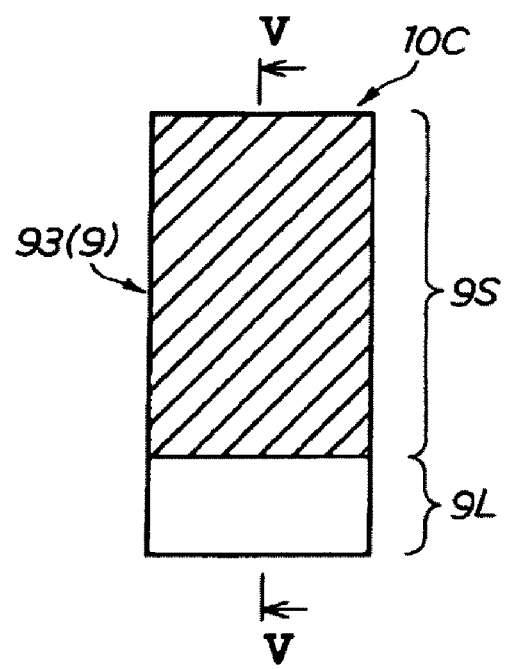
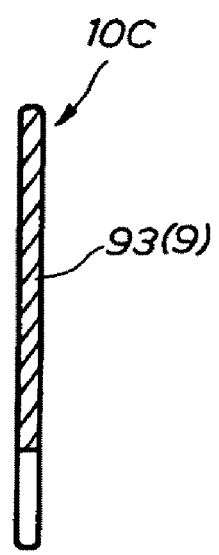

Superabsorbent polymer

Fig. 34(a)     Fig. 34(b)     Fig. 34(c)
 RA  RB         RA  RB         RA , RB
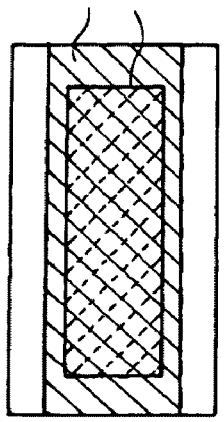 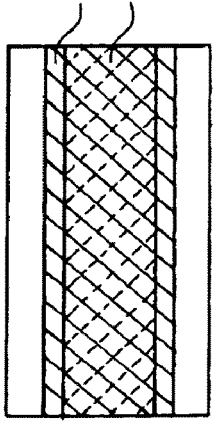 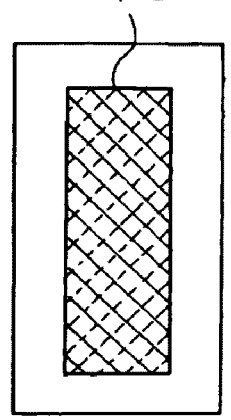
Fig. 34(d)     Fig. 34(e)
 RA  RB         RA  RB
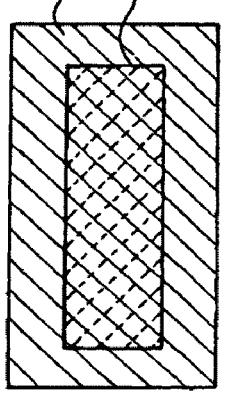 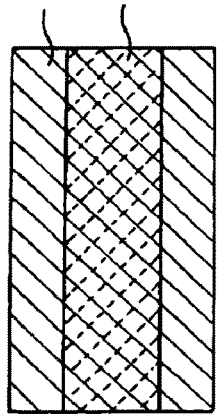
Fig. 35(a)                Fig. 35(b)
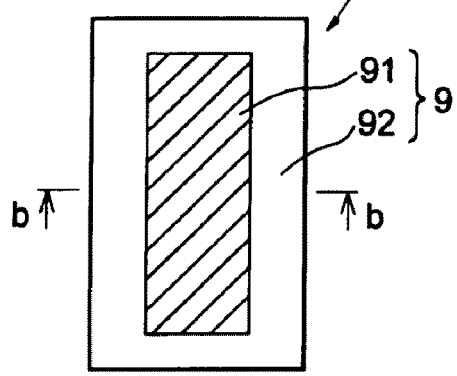 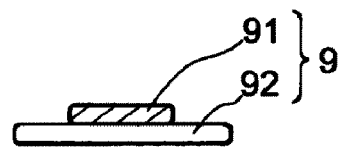

(a)

(b)

ABSORBENT MEMBER AND METHOD OF PRODUCING THE SAME

TECHNICAL FIELD

The present invention relates to an absorbent member suitable for use in various absorbent articles such as disposable diapers, sanitary napkins, and incontinence pads and a method of producing the same. The invention also relates to an absorbent article having the absorbent member.

BACKGROUND ART

Absorbent members for absorbent articles using an opened tow of continuous filaments are known. Included is an absorbent member disclosed in Patent Document 1, which has a crimped cellulose acetate fiber tow layer and a ground pulp layer superposed on one side of the tow layer, the two layers being united by pressing in the thickness direction. The absorbent member is described as having improved body fluid spreading properties. However, because cellulose acetate fiber is inferior to pulp in absorbency, a large quantity of ground pulp should be used in combination to secure sufficient absorption capacity. As a result, the absorbent member has an increased thickness, which reduces wearing comfort of the absorbent article.

A tow layer composed of continuous filaments is, however, not favorable in view of properties of wicking a fluid discharged on a skin contacting side in the thickness direction within a limited planar area (hereinafter referred to as "downward wicking properties").

A cellulose acetate fiber tow layer easily transmits a locally applied force to all over its area. Therefore, the tow layer is destroyed or bunches up easily with the wearer's motion. The absorbent member could be prevented from being destroyed or bunching to some extent by increasing the thickness of the ground pulp layer. In that case, however, the absorbent member would be bulkier, less soft, and less comfort during wear.

Patent Document 2 proposes an absorbent core composed of an upper layer, a lower layer, and an absorbent layer interposed therebetween. The absorbent layer is exemplified by a layer of spread superabsorbent polymer particles on which a fiber layer made of a cellulose acetate fiber tow is disposed. The superabsorbent polymer has a part thereof bonded to the lower layer with an adhesive and another part thereof entering the fiber tow layer. Although part of the superabsorbent polymer enters the fiber tow layer, the most part of the superabsorbent polymer is bonded to the lower layer. In other words, the fiber tow layer and the superabsorbent polymer layer are independent of each other so that the structure of the absorbent core tends to be destroyed when deformed by the wearer's motion during use of the absorbent article.

Known as a technique to prevent side leakage from a disposable diaper is to provide a ridge projecting toward the skin of a wearer on both sides of an absorbent member. However, formation of such ridges makes the production line complicated or increases the production cost.

Apart from these techniques, the assignee of the present invention previously proposed in Patent Document 1 an absorbent article having an absorbent member formed of a great number of small aggregates composed of pulp fiber, a superabsorbent polymer, and hydrophilic fiber having a longer fiber length than the pulp fiber.

Patent Document 1: JP 57-1604574A
Patent Document 2: WO 99/49826A1

DISCLOSURE OF THE INVENTION

The present invention relates to an absorbent member including a fiber aggregate containing continuous fibers and synthetic or semisynthetic staple fibers.

The present invention also relates to an absorbent member having a web of continuous fibers and lumpy particles held in the web. The continuous fibers in at least part of a region where the particles are distributed in a plane direction of the web are in a state cut into a great number of staple fibers.

The present invention also relates to a method of producing an absorbent member having a web of continuous fibers and lumpy particles held in the web, the continuous fibers in part of the web being in a state cut into a great number of staple fibers. The method includes the steps of spreading lumpy particles on a web of hydrophilic continuous fibers and pressing the web in at least part of the region where the particles have been spread in the thickness direction of the web to press the continuous fibers in that part onto the particles thereby to cut the continuous fibers.

The present invention also relates to an absorbent article having any of the above-described absorbent members. The absorbent article has the staple fibers disposed in a zone adapted to face a point of body fluid discharge of a wearer while worn (hereinafter sometimes referred to as a target zone).

The present invention provides in its first aspect an absorbent member having an absorbent core containing a fiber web. The fiber web is made mainly of synthetic or semisynthetic fibers. When the synthetic or semisynthetic fibers constituting the web are classified into four groups of fibers according to a ratio of their length to the total length of the absorbent core; a first group having the ratio less than 1/4, a second group having the ratio of 1/4 or more and less than 2/4, a third group having the ratio of 2/4 or more and less than 3/4, and a fourth group having the ratio of 3/4 or more, the fiber web contains at least three of the four groups of fibers.

The present invention also provides in its second aspect an absorbent member having an absorbent core containing a fiber web. The fiber web is made mainly of synthetic or semisynthetic fibers. When the synthetic or semisynthetic fibers constituting the web are classified into a first group having a length shorter than 25 mm, a second group having a length of 25 mm or longer and shorter than 50 mm, a third group having a length of 50 mm or longer and shorter than 100 mm, and a fourth group having a length of 100 mm or longer, the fiber web contains at least three of the four groups of fibers.

The present invention also provides a method of producing the absorbent member according to the first and second aspect of the invention. The method includes the steps of spreading particles on a web of continuous fibers and pressing the web in its thickness direction to cut the fibers. In this pressing step for cutting, the continuous fibers are pressed onto the particles and are thereby cut into a variety of lengths to provide at least three of the four groups of fibers.

The present invention also provides a method of producing the absorbent member according to the first and second aspect of the invention. The method includes a first cutting step to make a plurality of first cuts and a second cutting step to make a plurality of second cuts in a pattern different from that of the first cuts.

The present invention also provides a method of producing the absorbent member according to the first and second aspect of the invention. The method includes a cutting step in which a cutting member having randomly arranged cutting projections is pressed onto a web of continuous fibers to cut the fibers into a variety of lengths.

The present invention also provides in its third aspect an absorbent member having a web containing staple fibers and continuous fibers. The staple fibers are oriented in one planar direction of the absorbent member. The total fibers constituting the web have a degree of orientation of 1.2 or greater.

BRIEF DESCRIPTION OF DRAWING

FIG. 13(a) and FIG. 13(b) are each a view of still another embodiment of the absorbent member according to the invention, of which FIG. 13(a) is a plan, and FIG. 13(b) is a cross-section taken along line IV-IV in FIG. 13(a).

FIGS. 14(a) and 14(b) are each a view of still another embodiment of the absorbent member according to the invention, of which FIG. 14(a) is a plan, and FIG. 14(b) is a cross-section taken along line V-V in FIG. 14(a).

FIGS. 15(a) and 15(b) are each a view of still another embodiment of the absorbent member according to the invention, of which FIG. 15(a) is a plan, and FIG. 15(b) is a cross-section taken along line VII-VII in FIG. 15(a).

FIGS. 16(a) and 16(b) are each a view of still another embodiment of the absorbent member according to the invention, of which FIG. 16(a) is a plan, and FIG. 16(b) is a cross-section taken along line VI-VI in FIG. 16(a).

FIGS. 17(a), 17(b) and 17(c) are each a view of still another embodiment of the absorbent member according to the invention, of which FIG. 17(a) is a plan, and FIG. 17(b) is a cross-section taken along line VIII-VIII in FIG. 17(a).

FIG. 28(a), FIG. 28(b), and FIG. 28(c) each show a distribution pattern of superabsorbent polymer particles in Example 11; of which FIG. 28(a) is a plan, FIG. 28(b) a cross-section taken along the longitudinal direction of the absorbent member, and FIG. 28(c) a distribution curve of the superabsorbent polymer particles in the longitudinal direction of the absorbent member.

FIG. 29(a), FIG. 29(b), and FIG. 29(c) each show a distribution pattern of superabsorbent polymer particles in Example 12; of which FIG. 29(a) is a plan, FIG. 29(b) a cross-section taken along the longitudinal direction of the absorbent member, and FIG. 29(c) a graph showing the distribution of the superabsorbent polymer particles in the longitudinal direction of the absorbent member.

FIG. 34 (a), FIG. 34(b), FIG. 34(c), FIG. 34(d), and FIG. 34(e) are schematic plans of other embodiments of the absorbent member according to the third aspect of the present invention.

FIG. 35(a) is a plan of still another embodiment of the absorbent member according to the invention, and FIG. 35(b) is a cross-section taken along line b-b of FIG. 35(a).

FIG. 39(a) and FIG. 39(b) are each a view of still another embodiment of the absorbent member according to the invention, of which FIG. 39(a) is a plan, and FIG. 39(b) is a cross-section along line IV-IV in FIG. 39(a).

DETAILED DESCRIPTION OF THE INVENTION

The present invention will be described in detail based on its preferred embodiments.

Figure 1:
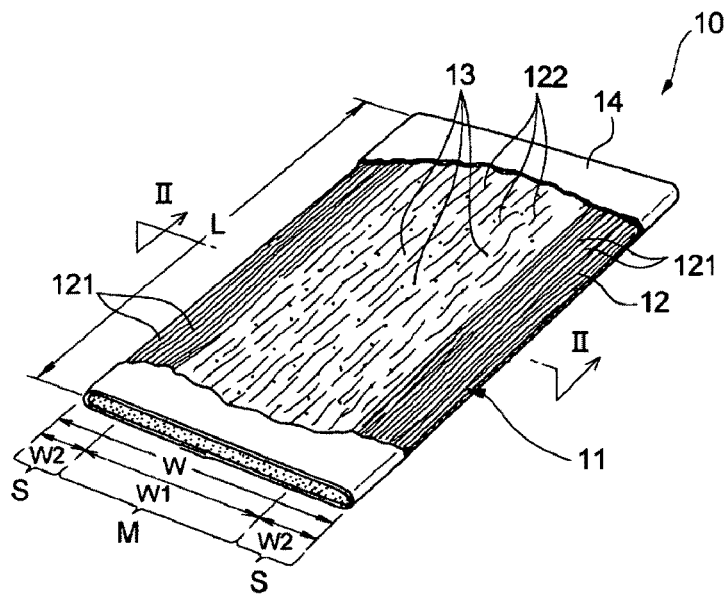
FIG. 1 is a perspective of one embodiment of the absorbent member according to the invention, with part cut away.
Figure 2:
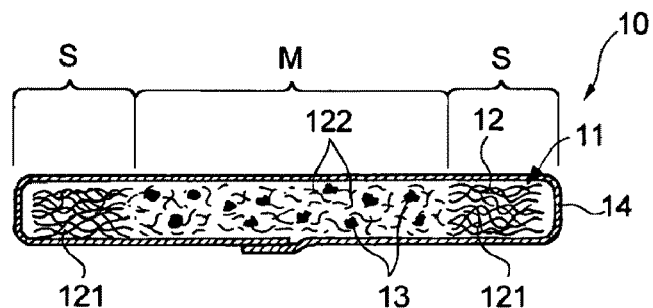
FIG. 2 is a schematic cross-section of the absorbent member of FIG. 1, taken along line II-II.

As illustrated in FIGS. 1 and 2, an absorbent member 10 according to a first embodiment includes an absorbent core 11 and a wrap sheet 14 covering the absorbent core 11. The absorbent core 11 has a web 12 of hydrophilic continuous fibers and a lumpy absorbent polymer (lumpy particles) 13 in the web 12.

The absorbent member 10 is an oblong rectangle in a plan view and is designed to be assembled into an absorbent article with its longitudinal direction coinciding with the front-to-rear direction of a wearer.

While the web 12 has originally been formed totally of continuous fibers, it has part of its continuous fibers cut into staple fibers in its finished state as the absorbent member 10. In the present invention the part formed of the staple fibers resulting from cutting the same continuous fibers as form the other part is regarded as a part of the continuous fiber web.

In the present embodiment the continuous fiber web 12 containing the staple fibers resulting from cutting the continuous fibers is "a fiber aggregate containing continuous fibers and synthetic or semisynthetic staple fibers".

The absorbent polymer 13 is localized in a part in a planar direction of the absorbent member 10. Specifically, as shown in FIGS. 1 and 2, it is localized in the part of the continuous fiber web 12 that is located, in a planar direction, in a region M of the absorbent member 10. The region M has a prescribed width and is located in the laterally middle portion of the absorbent member 10 (hereinafter also referred to as a middle region M). The absorbent polymer 13 is distributed substantially evenly in the part located in the middle region M and is substantially absent in the parts located in side regions S outboard of the middle region M.

In the part in a planar direction of the web 12 where the absorbent polymer 13 is distributed, i.e., the part located in the middle region M, there are a great number of staple fibers 122 resulting from cutting the same continuous fibers as the continuous fibers 121 constituting the parts located in the side regions S. The continuous fibers 121 constituting the part of the web 12 located in each side region S maintain the form of continuous fibers. The continuous fibers 121 in the part located in each side regions S are oriented in the longitudinal direction of the web 12.

The continuous fiber web 12 preferably contains crimped continuous fibers as the continuous fibers. The percent of crimp (JIS L0208) of the continuous fibers is preferably 10% to 90%, more preferably 10% to 60%, even more preferably 10% to 50%. The absorbent member 10 which contains crimped continuous fibers is flexibly deformable as a whole and, as assembled into an absorbent article, exhibits improved fit against a wearer's body or improved deformability to form a concave shape to enhance leak prevention.

The continuous fiber web 12 preferably contains crimped staple fibers as the staple fibers 122 resulting from cutting the continuous fibers (hereinafter also referred to as "staple fibers of continuous fiber origin"). The crimp percentage of the crimped staple fibers is preferably equal to that of the crimped continuous fibers. The absorbent polymer can be held more stably by the crimped staple fibers in the web and is thereby prevented from moving in or falling off the web.

The crimp of the continuous and the staple fibers may be either two-dimensional or three-dimensional. The percentage of crimp (or crimp percentage) of continuous fibers is defined to be a percentage of a difference between the length A of a crimped fiber in its straightened state and the natural length B of the crimped fiber to the length A, being calculated from equation:

Percentage of crimp (%)=(($A-B$)/$A$)×100

The natural length of a crimped fiber is the length of the straight line connecting the two ends of a continuous fiber in its natural state. The term "natural state" means a state of a continuous fiber hanging under its own weight with its one end fixed to a horizontal plate. The term "straightened state" means a state of a continuous fiber stretched out until no crimp remains under a minimum load. The number of crimps of the crimped continuous fibers having the recited percentage of crimp is preferably 2 to 25, more preferably 4 to 20, even more preferably 10 to 20, per centimeter. The crimp percentage of the staple fibers is obtained in the same manner, provided that the staple fiber to be measured should be at least 10 mm long.

The hydrophilic continuous fibers (inclusive of the staple fibers of continuous fiber origin) may be those essentially having hydrophilicity and/or those which are not essentially hydrophilic but have been rendered hydrophilic by hydrophilization treatment. The hydrophilic continuous fibers are preferably those essentially having hydrophilicity, more preferably cellulose acetate fibers or rayon fibers. Cellulose acetate fibers are particularly preferred for their capability of maintaining bulkiness even after being wetted. Cellulose triacetate fibers and/or cellulose diacetate fibers are preferred cellulose acetate fibers.

Nylon or acrylic fibers may be used as the continuous fibers (inclusive of the staple fibers of continuous fiber origin) to make up the web.

The hydrophilic continuous fibers (inclusive of the staple fibers of continuous fiber origin) preferably have a moisture regain of less than 10%, more preferably 1% to 8%, to secure liquid permeability. When the moisture regain is less than 10%, the fibers are prevented, even on absorbing water, from being plasticized and softened or from swelling to cause clogging. Furthermore, fibers having a high moisture regain tend to form hydrogen bonds between themselves or between different sites of the individuals because of moisture absorption or their own strong hydrophilic properties particularly when compressed in the manufacture of the absorbent article to adjust the thickness or when the absorbent article is left compressed, e.g., in a package for a long period of time. As a result, an absorbent member having such fibers tends to become hard to reduce wearing comfort and cause skin troubles by friction.

The moisture regain is measured in the method described in para. [0025] of WO99/49826A1.

The terminology "continuous fiber" as used throughout the description of the invention means a fiber having a fiber length preferably of 70 mm or longer, more preferably 80 mm or longer, even more preferably 100 mm or longer, as measured by the mean fiber length measurement method (method C) specified in JIS L1015. In cases where the whole length L (see FIG. 1) of a web per se is shorter than 100 mm, "continuous fiber" is defined as follows. When preferably at least 50%, more preferably 70% or more, even more preferably 80% or more, of the fibers making up the web extend over the whole length of the web, the fibers of the web are regarded as continuous fibers. The continuous fibers used in the present invention are generally termed "continuous filaments". A bundle of continuous filaments is generally termed "a tow". Accordingly, the terminology "continuous fiber" as used herein shall include a continuous filament.

The terminology "staple fiber" as used herein denotes a fiber having a fiber length of less than 70 mm, more preferably 5 to 70 mm, even more preferably 10 to 50 mm, as measured in the same manner as for the continuous fibers.

The absorbent member of the invention can contain very short fibers having a length of less than 5 mm or a nearly powder form the length of which would be difficult to measure or would involve a large margin of error when measured by the method of JIS L1015.

Since the continuous fibers of a part of the web are to be cut by compressively pressing the part of the web in the presence of lumpy particles (such as lumpy absorbent polymer particles) in the course of the production of the absorbent member, it is preferred that the continuous fibers used in the invention have a fiber strength of not more than 3 g/d, more preferably 0.5 to 2.5 g/d. The fiber strength is measured as follows.

Method of Measuring Fiber Strength:

The method of tensile strength measurement in "Test methods for man-made staple fibers" specified in JIS L1015 was followed. That is, a fiber is attached to a sheet of copier paper at both ends thereof with an 18 mm wide adhesive tape (Scotch Tape (trade name) from Nichiban Co., Ltd.) so as to have a spatial length (the length except the fixed parts at both ends) of 20 mm (or 10 mm in case of a short fiber). The specimen thus prepared is set between jaws of a Tensilon tensile tester (RTC-1150A, from Orientech Co., Ltd.), and, after the paper is cut along near each of the tape-fixed ends, pulled at a rate of 300 mm/min. A load cell having a full scale of 5 kg is used, and the measuring range is changed appropriately. The measurement is made at 10 points to obtain an average. A measurement value deviating 20% or more from the average is discarded, and an additional measurement is carried out.

The continuous fibers preferably have a fineness of 1.0 to 10 dtex, more preferably 1.5 to 8 dtex.

Since the continuous fibers of a part of the web are to be cut by compressively pressing the part of the web in the presence of lumpy particles (such as lumpy absorbent polymer particles) in the course of the production of the absorbent member, it is preferred that the continuous fibers used in the invention have a fiber strength of not more than 3 g/d, more preferably 0.5 to 2.5 g/d.

The staple fiber obtained by cutting the continuous fiber by a lumpy particle usually has different cross-sectional shapes between an end thereof and a middle portion thereof. The difference in cross-sectional shape between an end and a middle portion of a fiber can be decided as follows.

Method of Deciding Difference in Fiber Cross-Sectional Shape:

A cross-section of a fiber at an end and the middle is observed under an electron microscope at a magnification of 500 times or more. A decision is made based on the results of observation of ten randomly selected staple fibers. A fiber is vertically attached to a specimen mount, and the cross-sectional shape at an end of the fiber is observed from the fiber axial direction. The cross-sectional shape is an outline within the depth of focus of the electron microscope but not a projected image of the fiber cut end. The cross-sectional shape of either one of the ends is adopted. A fiber is cut at the center of its apparent length with a razor blade taking care not to cause resin tailing, and the cut end is observed in the same manner. The term "apparent length" of a fiber means a distance between both ends of a fiber, both the ends being fixed on a cardboard under a minimum load not to stretch the fiber.

The image of the end and that of the middle of a fiber are compared. When the two images have substantially the same shape and area, the fiber is regarded as having equal cross-sectional shapes between the end and the middle thereof. Otherwise, the fiber is regarded as having different cross-sectional shapes between the end and the middle thereof. The expression "substantially the same area" as used herein is intended to mean that, when an image of an end cross-section and that of a middle cross-section of a fiber are superimposed as illustrated in FIG. 21($a$), the total area S1 of the non-overlapping portion(s) a is equal to or less than 30% of the area S2 of the overlapping portion b, i.e., $S1/S2 \leq 0.3$.

The image of an end cross-section and that of a middle cross-section of a fiber should be superimposed to provide a maximum area S2 of the overlapping portion b by rotating one or both of the images about the center thereof or moving the center(s).

Figure 21A:
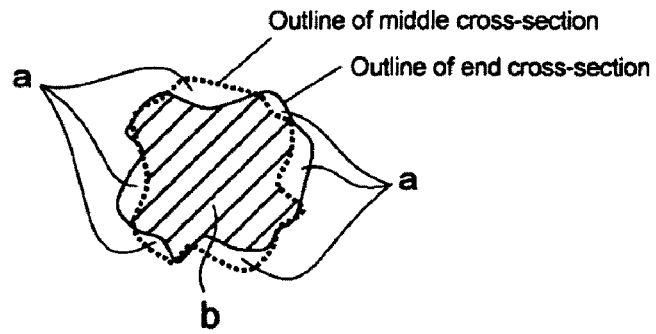
FIG. 21(a) and FIG. 21(b) are each an illustration explaining the method of evaluating cross-sectional shapes of a fiber.
Figure 21B:
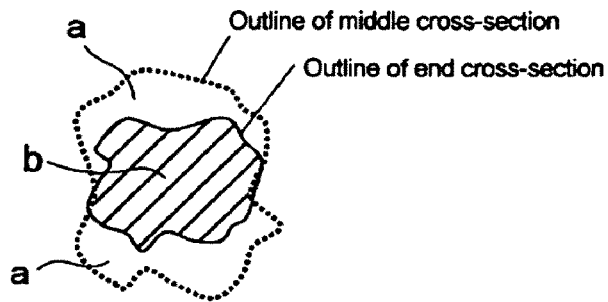

FIG. 21($a$) represents an example in which an end cross-section and a middle cross-section have substantially the same shape and area, while FIG. 21($b$) shows an example in which an end cross-section and a middle cross-section are regarded as having neither substantially the same shape nor substantially the same area.

In order to obtain good downward wicking properties, it is preferred that the staple fibers of continuous fiber origin be arranged such that the two longitudinal ends (cut ends) of individual staple fibers are located at random positions in the longitudinal direction of the absorbent member.

In the present invention, it is preferred to use lumpy particles. The term "lumpy" as used herein is intended to mean irregular and angular shapes or irregular shapes with a plurality of projections on the surface thereof.

Figure 50:
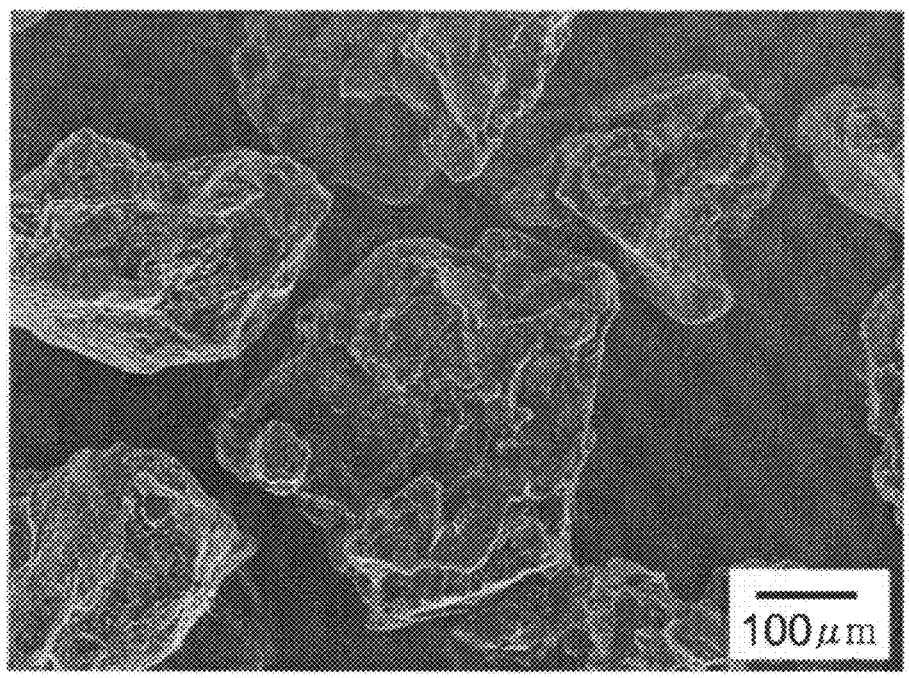
FIG. 50(*a*) is an electron micrograph of a type of lumpy absorbent polymer particles which are obtained by casting a water-containing gel of an absorbent polymer synthesized by solution polymerization into a sheet, drying the cast sheet, and grinding the dried sheet, and FIG. 50(*b*) is an electron micrograph of another type of lumpy absorbent polymer particles which are agglomerates of irregular particles formed by reverse phase suspension polymerization using a selected surface active agent under a controlled stirring force.
Figure 50:
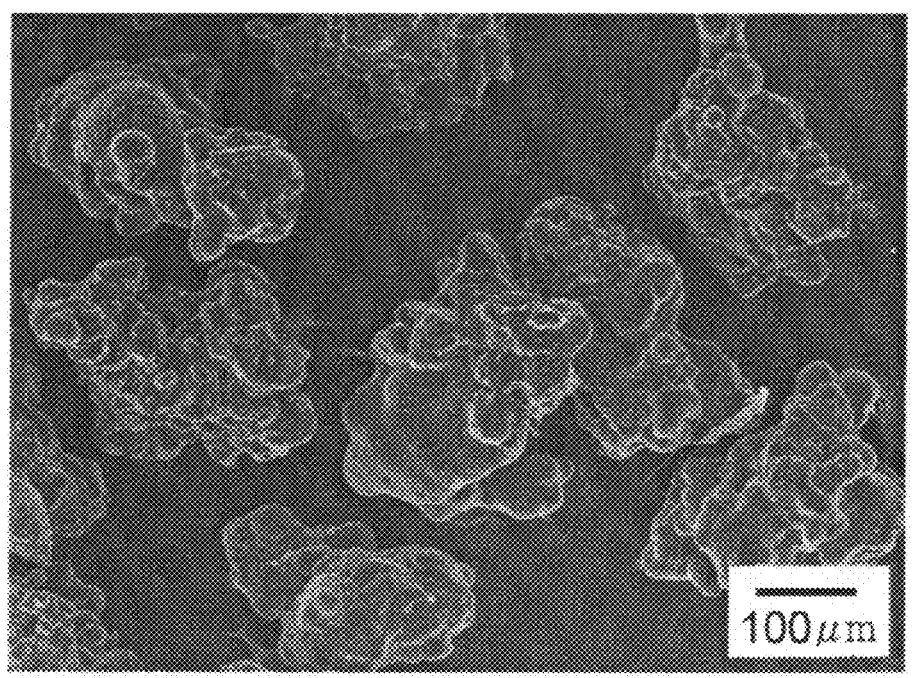

FIG. 50(a) is an electron micrograph of absorbent polymer particles having irregular and angular shapes, and FIG. 50(b) is an electron micrograph of absorbent polymer particles having irregular shapes with a plurality of projections on the surface.

The lumpy particles are preferably lumpy absorbent polymer particles. The lumpy absorbent polymer particles are obtained by casting a water-containing gel of an absorbent polymer synthesized by aqueous solution polymerization into a sheet, drying the cast sheet, and grinding the dried sheet, or the lumpy absorbent polymer particles are agglomerates of irregular particles formed by reverse phase suspension polymerization using a selected surface active agent under a controlled stirring force. On the other hand, non-lumpy absorbent polymer particles include spherical particles, agglomerates of spherical particles, fibrous particles, and flaky particles.

The lumpy absorbent polymer preferably has a bulk density of 0.5 to 0.8 $g/cm^3$, more preferably 0.55 to 0.7 $g/cm^3$. The lumpy absorbent polymer particles preferably have an average particle size of 150 to 600 µm, more preferably 200 to 500 µm.

Examples of the absorbent polymer include those conventionally used in absorbent members of disposable diapers, sanitary napkins, and the like, such as sodium polyacrylate, acrylic acid-vinyl alcohol copolymers, crosslinked sodium polyacrylate, starch-acrylic acid graft polymers, isobutylene-maleic anhydride copolymers and saponification products thereof, potassium polyacrylate, and cesium polyacrylate.

The absorbent polymer preferably has capability of absorbing at least 20 times its weight of water or physiological saline.

Examples of the lumpy particles other than the lumpy absorbent polymer include organic or inorganic particles useful as a deodorant or an antimicrobial agent such as cellulose powder, activated carbon, silica, alumina, and various minerals (e.g., zeolite, sepiolite, bentonite, and cancrinite). These lumpy particulate substances may be used either individually or in combination of two or more thereof. The inorganic particles may have part of their metal sites replaced. The lumpy particles may be used as agglomerates thereof or as a composite with a carrier. These lumpy particles may be used in combination of two or more thereof. Porous particles such as activated carbon or silica gel preferably have an average particle size of 20 to 300 µm, more preferably 50 to 150 µm, and agglomerates or composites with a carrier preferably have an average particle size of 150 to 600 µm, more preferably 200 to 500 µm. The action of these components is to subdue the odors of bodily wastes absorbed by the absorbent member or the odors originated in the material of the absorbent member.

The lumpy absorbent polymer may be used in combination with a non-lumpy absorbent polymer. In the case where the continuous fibers are cut without relying on lumpy particles, a non-lumpy polymer may be used alone.

The non-lumpy polymer is exemplified by spherical particles obtained by spray-drying a mixture of a monomer, a polymerization initiator, a crosslinking agent, etc. or by a reverse phase suspension polymerization process using a selected solvent and a selected surface active agent (spherical polymer particles with no irregularities on their surface are obtained generally by selecting a solvent making a small difference of solubility parameter from the polymer).

In the case where the continuous fibers in part of the web are cut by compressing absorbent polymer particles with, e.g., a roller, part of the absorbent polymer particles can be broken into finer particles. Because finer absorbent polymer particles are more likely to be closely packed than larger absorbent polymer particles, they can cause gel blocking or retard liquid acquisition. When the absorbent polymer is a crosslinked polymer, the weakly crosslinked inside part will be exposed by breaking, which can also result in gel blocking. Gel blocking causes a discharged fluid to remain on the surface of the absorbent member or an absorbed fluid to flow back and rewet the skin. In case such inconveniences could occur, the absorbent member of the present invention may contain a buffering agent of various kinds, either organic or inorganic, so that a buffer system may be provided when the absorbent member absorbs a bodily waste. Examples of useful buffers include acetic acid, phosphoric acid, citric acid, succinic acid, adipic acid, malic acid, lactic acid, and their salts, used either alone or in combination thereof, and various amino acids. Additionally, the organic or inorganic buffers neutralize ammonia resulting from decomposition of body wastes, e.g., urine, thereby serving to maintain a diaper neutral to weakly acidic. This will lessen the adverse influences of body wastes on the skin if a body waste should rewet the skin. In the case when fibers having an ester bond in the molecule thereof such as cellulose acetate fibers are used as the continuous fibers of the web 12, the alkali (e.g., ammonia) neutralizing function of the organic or inorganic buffer is expected to prevent the fibers from being damaged due to alkali-decomposition of the ester bonds.

The web may further contain hydrophilic powder or stable fibers for the purpose of enhancing the improvement of downward wicking properties as one of the effects of the invention and also improving liquid retentivity, absorption rate, and a dry feel. Examples of the hydrophilic powder or staple fibers include fibrillated or non-fibrillated cellulose powder, carboxymethyl cellulose and its metal salts, carboxyethyl cellulose and its metal salts, hydroxyethyl cellulose and its derivatives, silk powder, nylon powder, and staple fibers such as rayon, cotton, and wool. Preferred of them is cellulose powder; for it achieves the highest degrees of the above-mentioned improvements. The hydrophilic powder or staple fibers may be spread either before spreading the absorbent polymer or simultaneously with the absorbent polymer in the form of a blend with the absorbent polymer.

In case the staple fibers resulting from cutting the continuous fibers have too short lengths, it is preferred to bond the continuous fibers constituting the web for the purpose of improving the web shape retention, thereby to increase the recovery of the web from compression, to prevent the web from bunching, and to improve web transport properties. Bonding between the continuous fibers can be done with a water-soluble adhesive such as polyvinyl acetate and an acrylic resin emulsion.

When the continuous fibers are cellulose acetate fibers, bonding of the continuous fibers can be achieved by spreading an agent capable of dissolving or plasticizing the acetate, such as triacetin, after spreading the absorbent polymer, whereby the continuous fibers are dissolved or plasticized to adhere to each other.

Bonding the continuous fibers to each other may also be performed by dispersing synthetic pulp of a thermoplastic resin in the web and heating the synthetic pulp. The synthetic pulp is spread in the web either simultaneously with, or after or before spreading the absorbent polymer. The web is preferably sucked during the spreading from the opposite side so that the synthetic pulp and the absorbent polymer may be sufficiently distributed throughout the web. In the case where the continuous fibers are thermoplastic resin fibers, the synthetic pulp to be spread is preferably of a thermoplastic resin having a lower melting point than that of the thermoplastic resin fibers.

When the absorbent member is embossed, a large number of debossed portions where the web is densified are formed. That is, the embossed web has high fiber density portions and low fiber density portions. As a result, a difference of capillarity is created between the high density portions and low density portions, which brings about improved wicking properties of the absorbent member 10.

In order to enhance the downward wicking properties and to improve web shape retention, a sheet or a plurality of sheets made of paper, nonwoven fabric, etc. may be superposed or wrapped around the upper and/or lower side of the web and/or the side portions of the web and joined to the web with an adhesive that has previously been applied to the sheet side or by heat fusion. By this method, an absorbent member of sheet form is obtained, in which the web is held in between a pair of sheets. Such an absorbent member of sheet form has increased stiffness due to the joint with the sheet and the stiffness of the sheet per se and therefore exhibits improved handling properties and can easily be transported alone. Furthermore, the absorbent member of sheet form can easily be trimmed or punched into any desired contour in conformity to the contour of an absorbent article.

When the sheet and the web are joined with an adhesive to increase the web shape retention, the adhesive is preferably applied so as not to impair water permeability, softness, and breathability of the web. It is advantageous for this that the adhesive be applied in as fine a line as possible in a discontinuous pattern such as an array of spirals, separate lines, or "omega" shaped lines. Fibers can thus be bonded at a number of joints without ruining the characteristics of the web. This can be achieved by using, for example, UFD Fiber (trade name), a kind of hot melt adhesive applicator. Any type of adhesives, either hydrophilic or hydrophobic, may be used with no limitation. A hydrophilic adhesive is preferred. A useful hydrophilic adhesive is exemplified by Cycloflex (registered trade name of a hydrophilic hot melt adhesive from National Starch & Chemical Corp., Delaware, U.S.A.).

Although the adhesion between the sheet and the web is between the surfaces of the two adherents, the term "adhesion" as used here includes incidental bonding between fibers in the thickness direction of the web because the adhesive may penetrate into the web.

To superpose the sheet on the upper side and/or the lower side of the web is advantageous to enhance the absorbing performance of the absorbent member. To increase the absorbing performance of the absorbent member, it is preferred to use a fiber sheet or a fiber web as the sheet. Examples of such a sheet material include air-through nonwovens, air-laid nonwovens, dry processed pulp nonwovens, crosslinked pulp, paper containing crosslinked pulp, and composites of the sheet materials recited. These sheets may be used singly, or a plurality of the sheets may be used as a stack. The fibers making up the sheet preferably have a fineness of 1.7 to 12 dtex, more preferably 2.2 to 7.8 dtex, even more preferably 3.3 to 5.6 dtex. The sheet preferably has a basis weight of 15 to 200 $g/m^2$, more preferably 20 to 150 $g/m^2$, even more preferably 25 to 120 $g/m^2$. When it is demanded to improve the rate of fluid acquisition, to prevent rewet, or to facilitate fluid spread in the sheet, it is preferred to use a sheet having a basis weight of 15 to 100 $g/m^2$, more preferably 20 to 80 $g/m^2$, even more preferably 25 to 50 $g/m^2$. When it is demanded to improve the cushioning properties of the absorbent member, to prevent the absorbent member from bunching, to impart recovery from compression to the absorbent member, or to suppress dissipation of water vapor from the absorbent member, it is preferred to use a sheet having a basis weight of 25 to 200 $g/m^2$, more preferably 30 to 150 $g/m^2$, even more preferably 40 to 120 $g/m^2$.

Figure 3:
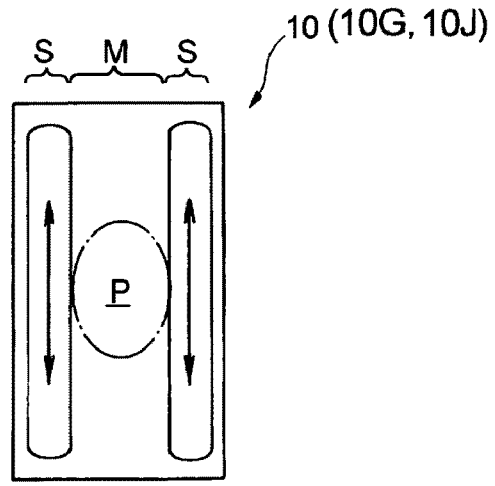
FIG. 3 is a schematic plan illustrative of the effects of the absorbent member shown in FIG. 1.

The absorbent member 10 of the present embodiment is assembled into an absorbent article such as a disposable diaper or a sanitary napkin with its middle region M (where the continuous fibers have been cut into staple fibers) located in the target zone P that is adapted to face a point of body fluid discharge of a wearer as illustrated in FIG. 3. In this mode of application, a body fluid discharged from the point of discharge (e.g., urine or menstrual blood) is smoothly drawn into the inside of the absorbent member 10 within a small planar area owing to the excellent downward wicking properties of the staple fibers. The fluid acquired into the absorbent member 10 is absorbed by the absorbent polymer 13 localized in the zone and thus stably retained in the absorbent member 10.

When the absorbent member 10 receives a considerable quantity of a fluid in a short time or acquires large quantities of a fluid duling long time use, the fluid can spread to the side regions S. Since there are continuous fibers in the side regions S, remaining non-cut and aligned in the longitudinal direction of the absorbent member, the fluid having reached the side regions S well diffuses in the longitudinal direction of the absorbent member 10 (the front-to-rear direction of a wearer), while being suppressed from diffusing across the side regions S. As a result, leakage from both side edges of the absorbent member 10 is prevented effectively, and a larger area of the absorbent member can be made effective use of.

In the present embodiment, both the absorbent polymer 13 and the staple fibers 122 of continuous fiber origin exist in the middle region M of the absorbent member 10, and the distribution range of the absorbent polymer (particles) 13 and the area in which staple fibers 122 have been generated coincide with each other.

To prevent side leakage from the absorbent member 10 incorporated in an absorbent article, the width W1 (see FIG. 1) of the area in which the staple fibers 122 have been generated (equal to the width of the middle region M) along the lateral direction of the absorbent member 10 is preferably 20% to 95%, more preferably 50% to 85%, of the whole width W (see FIG. 1) of the absorbent member 10, and the total of width W2 (see FIG. 1) of the areas in which staple fibers are substantially absent (equal to the total width of the side regions S) is preferably 5% to 80%, more preferably 15% to 50%, of the whole width W of the absorbent member 10.

The wrap sheet 14 is preferably a water permeable sheet material such as a pulp sheet (e.g., tissue paper) or a water permeable nonwoven fabric. The surfaces of the regions corresponding to the width W2 where the absorbent polymer 13 and the staple fibers 122 are substantially absent do not always need to be covered with the wrap sheet.

In view of the amount of the absorbent polymer to be used and prevention of reduction in gel feel after fluid acquisition, it is preferred that the absorbent polymer used in the preferred embodiments of the present invention have a physiological saline absorption of 30 g/g or more, more preferably 30 to 50 g/g, measured by a centrifugal dewatering method. The physiological saline absorption measurement by a centrifugal dewatering method is carried out as follows. An absorbent polymer weighing 1 g is swollen with 150 ml of physiological saline over 30 minutes, put in a 250 mesh nylon bag, and dewatered using a centrifuge at 143 G (800 rpm) for 10 minutes. The gross weight of the dewatered bag and the contents is measured, from which the absorption (g/g) by a centrifugal dewatering method is calculated according to equation:

Water absorption by centrifugal dewatering method=
(gross weight after dewatering−weight of nylon
mesh bag−dry weight of absorbent polymer−
weight of liquid retained by nylon mesh bag)/dry
weight of absorbent polymer In order to prevent gel blocking and the resultant reduction in absorbency from occurring and to prevent leakage of a fluid having passed through the polymer particles without being absorbed, it is also preferred for the absorbent polymer to have a liquid transit time of 20 seconds or less, more preferably 2 to 15 seconds, even more preferably 4 to 10 seconds, as measured by the following method. The liquid transit time is measured as follows. A cylinder having a cross-sectional area of 4.91 cm$^2$ (inner diameter: 25 mm) with its bottom closable with a cock (inner diameter: 4 mm) is prepared. In the cylinder with its bottom closed is put 0.5 g of an absorbent polymer, and the cylinder is filled with physiological saline. After the polymer is swollen to saturation and sinks to the bottom, the cock is opened to make 50 ml of the physiological saline pass through. The time required for 50 ml of the saline to pass through is taken as the liquid transit time. The liquid transit time is a measure of the gel strength of the absorbent polymer. A shorter liquid transit time indicates higher gel strength.

It is also preferred for the absorbent polymer to have high liquid permeability under load. More specifically, to effectively prevent gel blocking of the absorbent polymer from occurring, it is preferred that the absorbent polymer have a liquid permeation rate of 30 to 300 ml/min, more preferably 32 to 200 ml/min, even more preferably 35 to 100 ml/min. If the liquid permeation rate is less than 30 ml/min, the absorbent polymer particles swollen with a fluid to saturation are liable to stick to one another under load and obstruct passage of liquid (gel blocking). The higher the liquid permeation rate, the more preferred to prevent gel blocking from occurring. Occurrence of gel blocking is prevented almost certainly when the liquid permeation rate is about 40 ml/min. Where the liquid permeation rate exceeds 300 ml/min, the flow of the fluid in the absorbent member is too fast. It may follow that fixation of the liquid is insufficient, which can cause leakage, particularly when a large amount of excrement is discharged at a time or when excrement is released very fast as by older babies or by adults, or when the absorbent member is designed to have a reduced thickness. In general, to increase the liquid permeation rate means to increase the degree of crosslinking of the absorbent polymer, which results in decreasing absorption capacity of the absorbent polymer per unit weight. This leads to necessity to use an increased amount of the absorbent polymer. From these considerations, the upper limit of the liquid permeation rate shall be decided.

Method of Measuring Liquid Permeation Rate:

A filtration cylinder (inner diameter: 25.4 mm) equipped at the lower open end thereof with a metal mesh (mesh size: 150 μm) and a narrow tube (inner diameter: 4 mm; length: 8 cm) with cock (inner diameter: 2 mm) is prepared. The cylinder with the tube closed with the cock is vertically held, and 0.32 g of a sample having a particle size adjusted to 150 to 850 μm is put therein. Then, 50 ml of 0.9 wt % physiological saline is poured in the cylinder. After allowing the cylinder to stand for 30 minutes from the start of pouring the physiological saline, a circular rod weighing 21.2 g and having attached to the tip thereof a metal mesh having a mesh size of 150 μm and a diameter of 25 mm is inserted in the filtration cylinder until the metal mesh comes into contact with the sample. One minute later, a 77.0 g weight is attached to the circular rod to apply an appointed load to the sample. After the cylinder is left to stand for an additional 1 minute period, the cock is opened, and the time T1 (sec) required for the liquid level of the saline to drop from the 40 ml mark to the 20 ml mark is measured. The liquid transit time is calculated according to formula below using the thus measured time T1 (sec). In the formula T0 is the time measured with no sample in the filtration cylinder.

Liquid permeation rate (ml/min)=20×60/(T1−T0)

It is preferred that the absorbent polymer to be used in the preferred embodiments of the invention satisfy the above-mentioned characteristics. Examples of such absorbent polymers include sodium polyacrylate, acrylic acid-vinyl alcohol copolymers, crosslinked sodium polyacrylate, starch-acrylic acid graft copolymers, isobutylene-maleic anhydride copolymers and saponification products thereof, potassium polyacrylate, and cesium polyacrylate. In order for the absorbent polymer to satisfy the characteristics, a crosslinking density gradient is provided on the surface of the absorbent polymer particles, or aspherical, irregularly shaped absorbent polymer particles are used. Specifically, the methods disclosed in JP 7-184956A, col. 7, line 28 to col. 9, line 6 can be used.

Compared with conventional absorbent members containing fluff pulp as a main component, the absorbent member having the continuous fiber web provides a less dense structure with larger interstices between fibers and therefore exhibits good liquid permeability. When the absorbent polymer is slow to absorb a fluid, it is likely to happen that a fluid fails to be sufficiently absorbed by the absorbent polymer because it passes through the absorbent member before being absorbed by the absorbent polymer. Taking this into consideration, it is desirable for the absorbent polymer contained in the web to have a sufficiently high absorption rate whereby the fluid is retained within the absorbent member without fail. The absorption rate of the absorbent polymer is generally represented in the art by the value obtained by the demand wettability (DW) method. An absorption rate (ml/(0.3 g·30 sec)) according to the DW method can be measured with a DW tester generally known for carrying out the DW method. In some detail, with the liquid levels of physiological saline being equal, 0.3 g of a superabsorbent polymer is scattered on a mount (diameter: 70 mm; No. 1 glass filter having placed thereon No. 2 filter paper), and the water absorption after 30 seconds is gauged by reading the scale on the buret indicating a drop of the liquid level of physiological saline (the water absorption at the time of scattering the polymer is taken zero). The amount of absorption as measured is taken as an absorption rate. The absorption rate of an absorbent polymer can be adjusted by the particle shape and size, bulk density, crosslinking degree, and so forth.

In embodiments in which the absorbent member contains no or, if any, not more than 30% by weight of pulp, it is preferred to use an absorbent polymer having an absorption rate of 2 to 10 ml/0.3 g·30 sec, more preferably 4 to 8 ml/0.3 g·30 sec, measured by the DW method. In the production of conventional absorbent members made mainly of fluff pulp, the use of an absorbent polymer having such a high absorption rate has been avoided for fear of inducing gel blocking which leads to leakage. In the present embodiment, however, since the web exhibits high fluid acquisition properties and allows the fluid acquired to pass through at a high speed owing to its sparse structure, the absorbent polymer having such a high rate of absorption hardly causes gel blocking and, on the contrary, effectively prevents leakage.

The absorbent polymer having a short liquid transit time or a high absorption rate as described may be used alone or may be used as a mixture with or in combination with another absorbent polymer whose liquid transit time or absorption rate falls in the above-specified preferred range. For example, an absorbent polymer S1 having a relatively short liquid transit time and an absorbent polymer S2 having a relatively long liquid transit time can be used as a mixture. Comparing the absorbent polymers S1 and S2, the absorbent polymer S2 has a higher absorption capacity and a higher absorption rate but is less resistant to gel blocking. In the system containing both the absorbent polymers S1 and S2, the absorbent polymer S1, which is harder and less likely to induce gel blocking, enters between the particles of the absorbent polymer S2 having higher absorbency. As a result, the absorbent member can be made more effective use of. As another example, an absorbent polymer S3 having a relatively high absorption rate and an absorbent polymer S4 having a relatively low absorption rate may be used in combination. In this example, the absorbent polymer S3 and the absorbent polymer S4 are disposed on the backsheet side and the topsheet side, respectively, thereby increasing the rate of fluid acquisition and fluid fixing ability of the absorbent member. In still another example, the same effects are obtained by disposing the absorbent polymer S1 having a short liquid transit time and the absorbent polymer S3 having a high absorption rate on the topsheet side and the backsheet side, respectively.

By using the absorbent polymers having the above described specific absorption characteristics, the absorbent member according to the present invention has a reduced amount of rewet notwithstanding its thinness and softness. The amount of rewet is preferably 1 g or less, more preferably 0.5 g or less, even more preferably 0.25 g or less, as measured as follows. In testing a medium size disposable diaper for infants, colored saline weighing 160 g is poured on the widthwise middle portion 150 mm below the frontal waist edge of the diaper by use of a funnel. The colored saline is prepared by adding FD & C Red No. 1 to physiological saline in a concentration of 50 ppm (0.5 g per 10 liters of physiological saline). Ten minutes after completion of the pouring, a stack of ten sheets of filter paper No. 4A available from Advantech Tokyo Kaisha, Ltd. is placed on the wet portion, and a load of 3.43 kPa is applied thereon for 2 minutes to have the filter paper absorb the saline. The filter paper is weighed, and the weight gain is taken as the amount of rewet. Measurement is made three times to obtain an average. When a diaper of other size is tested, the following alterations are made. In the case of disposable diapers for infants, the load applied to the filter paper being fixed at 3.43 kPa, the amount of the saline to be poured is changed according to size (120 g for newborn and S size diapers, 160 g for other sizes). In testing absorbent articles for adults inclusive of sanitary napkins, the load applied to the filter paper is fixed at 5.15 kPa. In testing sanitary napkins, 10 g of horse blood is used in place of the colored physiological saline.

A preferred method of preparing the absorbent member 10 (an embodiment of the method of producing the absorbent member according to the present invention) will be described by way of FIG. 4.

Figure 4:
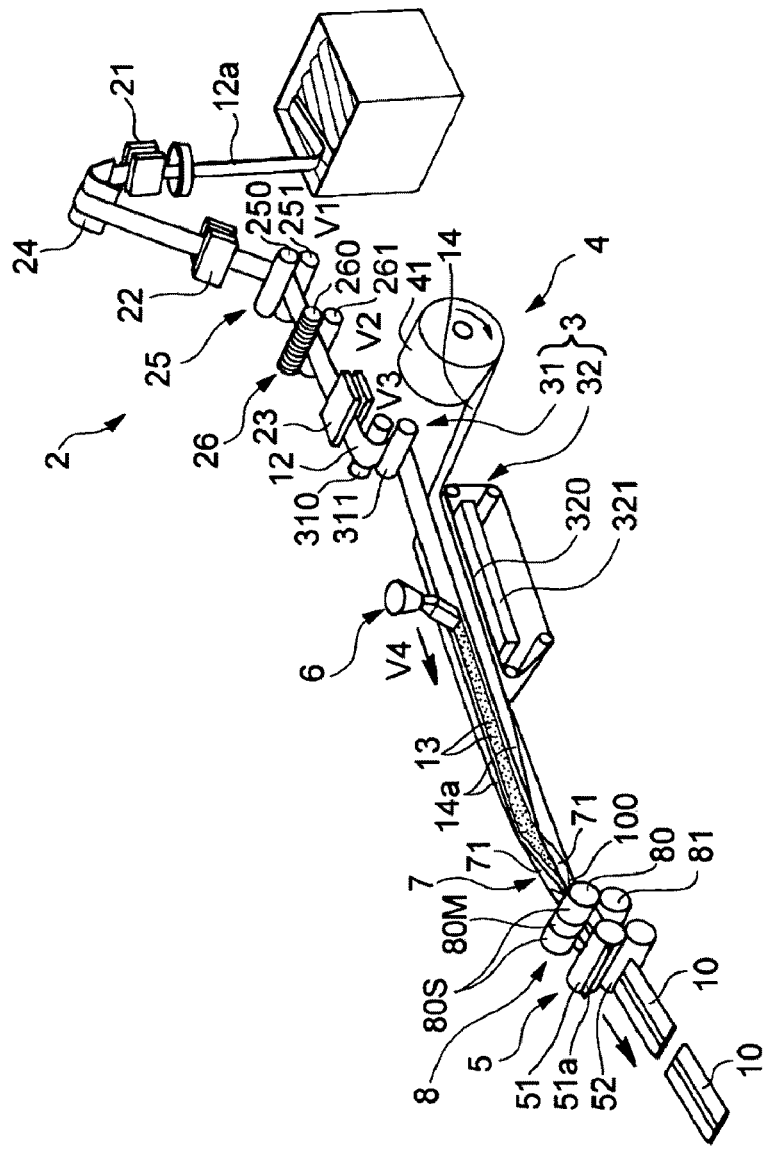
FIG. 4 is a schematic perspective of the apparatus for carrying out one embodiment of the method of producing the absorbent member according to the invention.

The apparatus of producing an absorbent member shown in FIG. 4 includes a tow opening mechanism 2 in which a continuous fiber tow 12a is opened while being conveyed under tension in the machine direction to form a continuous fiber web 12; a tension relaxing mechanism 3 in which the tow-opened web 12 is relieved from the tension and conveyed to the position where a polymer 13 is fed; a rap sheet feeding mechanism 4 for feeding a wrap sheet 14 on one side of the continuous fiber web 12; an absorbent polymer feeding mechanism 6 for feeding an absorbent polymer 13 on the side of the web 12 opposite to the side of the rap sheet 14; a folding mechanism 7 in which both lateral side portions 14a of the rap sheet 14 extending from both edges of the web 12 are folded over the other side to cover both sides of the web 12; and a continuous fiber cutting mechanism 8 in which the web wrapped on both sides thereof in the rap sheet is compressed in its thickness direction together with the rap sheet to cut the continuous fibers in part of the web 12.

The tow opening mechanism 2 is configured to continuously draw a tow 12a from a bale (a tow band in a folded and compressed form) and open the tow 12a during conveyance. The tow opening mechanism 2 has banding jets (tow opening units) 21 to 23, a guide 24 between the banding jets 21 and 22 to once raise and then lower the tow 12a, and a pre-tensioning unit 25 and a blooming unit 26 between the banding jets 22 and 23. Each of the banding jets 21, 22, and 23 is a unit for opening and laterally spreading the running tow by blowing air. The pre-tensioning unit 25 includes a pair of rollers 250 and 251 that nip the tow 12a opened by the banding jet 21 and feed it at a prescribed speed. The blooming unit 26 includes a grooved metal roller 260 having a large number of parallel grooves and teeth threaded along the direction of rotation and an anvil roller 261 the periphery of which is made of rubber. A difference of rotational speed is provided between the pre-tensioning unit 25 and the blooming unit 26, and the teeth of the grooved roller 260 press part of the fibers to give tension while the part of the fibers entering the grooves of the grooved roller 260 are not given tension, whereby the tow 12a is further opened.

The tension relaxing mechanism 3 includes a feed unit 31 downstream the banding jet 23 and a vacuum conveyor 32. The feed unit 31 has a pair of rollers 310 and 311 rotatably driven at a speed lower than the peripheral speed V2 of the blooming unit 26. The feed unit 31 is configured to superpose the continuous fiber web 12, which is obtained by opening the tow 12a in the tow opening mechanism 2, on the upper side of a rap sheet 14 fed on the vacuum conveyor 32 while giving the web 12 a tension lower than the tension applied between the pre-tensioning unit 25 and the blooming unit 26. The vacuum conveyor 32 has an air-permeable endless belt 320 driven at a running speed V4 that is still lower than the feeding speed V3 of the feed unit 31 (i.e., the peripheral speed of the pair of rollers 310 and 311) and a suction box 321. The web 12 superposed on the rap sheet 14 running on the vacuum conveyor 32 is further conveyed by the endless belt 320 to the polymer feed position while being relaxed from the tension.

The rap sheet feeding mechanism 4 is configured to feed the rap sheet 14 to one side of the continuous fiber web 12. The rap sheet feeding mechanism 4 includes means for unrolling the rap sheet 14 and a guide roller (not shown) for guiding the unrolled rap sheet 14 to the vacuum conveyor 32. The unrolling means has a roll 41 of the rap sheet 14 and a drive unit (not shown) for unrolling the roll 41.

The absorbent polymer feeding mechanism 6 is configured to spread absorbent polymer particles 13 from a polymer feed port placed above the upper side (opposite to the side of the rap sheet 14) of the continuous fiber web 12. The suction box 321 is provided on the opposite side of the upper run of the endless belt 320 to the polymer feed port. The absorbent polymer is spread while being sucked from the opposite side of the web 12 by the suction box 321. The width of the polymer feed port in the direction perpendicular to the running direction (longitudinal direction) of the web 12 is smaller than the width of the web so that the polymer 13 may be distributed in only the middle portion having a predetermined width of the web 12.

The folding mechanism 7 has a folding guide 71 on both sides of the machine direction. While the rap sheet 14 is continuously transported under tension by a pair of rollers 80 and 81 of the continuous fiber cutting mechanism 8, the side portions 14a thereof laterally extending from both edges of the web 12 are folded over the upper side of the web 12 as guided by the guides 71 to cover the upper side of the web 12. Thus, the web 12 has its both upper and lower sides covered by the rap sheet 14.

The continuous fiber cutting mechanism 8 includes a pair of rollers 80 and 81, between which the continuous fiber web 12 covered with the rap sheet 14 is compressed in its thickness direction. The composite composed of the continuous fiber web 12 with the polymer particles spread thereon and the rap sheet 14 wrapping the web will also hereinafter be referred to as a continuous-form absorbent member 100.

The roller 80 has a peripheral surface 80M having a prescribed width in the axially middle portion and peripheral surfaces 80S in the portions located on both sides of the middle surface 80M in the axial direction. The surface 80M is made of an elastic material such as rubber or silicone, and the peripheral surfaces 80S are each made of a hard material (inelastic material) such as a metal (e.g., steel). The width of the peripheral surface 80M made of an elastic material in the direction perpendicular to the web 12 is substantially the same as the width of the polymer feed port in the same direction.

Downstream the continuous fiber cutting mechanism 8 is provided a continuous-form absorbent member cutting mechanism 5. The continuous-form absorbent member cutting mechanism 5 includes a cutter roller 51 having a cutting blade 51a extending in the axial direction and an anvil roller 52 and is configured to cut the continuous-form absorbent member 100 into individual absorbent members, each of which is to be assembled into an absorbent article.

The absorbent member 10 is produced by use of the above-described apparatus as follows. As illustrated in FIG. 4, in the tow opening mechanism 2, a tow band 12a is continuously drawn from a bale and spread by applying compressed air in the banding jets 21 to 23 and by stretching taking advantage of the peripheral speed difference between the pre-tensioning unit 25 and the blooming unit 26 thereby to obtain a continuous fiber web 12.

The resulting web 12 is transported through the feed unit 31 and superposed on the rap sheet 14 supplied on the vacuum conveyor 32.

While the web 12 and the wrap sheet 14 are transported on the vacuum conveyor 32, the absorbent polymer 13 is spread on the web 12 by the absorbent polymer feeding mechanism 6.

In the present embodiment, the absorbent polymer 13 is spread over only a prescribed width in the laterally middle portion of the web 12. The absorbent polymer 13 is spread in a continuous manner in the longitudinal direction of the web 12. The amount of the absorbent polymer 13 to be spread is preferably equal to or greater than, more preferably twice or more times, even more preferably three or more times, the basis weight of the web 12 to cut the continuous fibers as desired. When, for example, the web 12 has a basis weight of 30 g/m$^2$, the amount of the absorbent polymer 13 to be spread is preferably 30 to 400 g/m$^2$, more preferably 60 to 300 g/m$^2$.

In the present embodiment, the web 12 obtained by opening the tow 12a is superposed on the wrap sheet 14 in a state contracted as compared with the most stretched state during tow opening. More specifically, the opening of the tow 12a is effected by driving the blooming unit 26 at a peripheral speed V2 higher than the peripheral speed V1 of the pre-tensioning unit 25. On the other hand, the running speed V4 of the wrap sheet 14 (equal to the running speed of the endless belt 320 of the vacuum conveyor 32) is lower than the peripheral speed V2 of the blooming unit 26. That is, the tension imposed to the web 12 on the vacuum conveyor 32 is relaxed to cause the continuous fibers to develop crimps. In that way, the preferred crimp percentage previously recited can be achieved efficiently. In the present embodiment, the most stretched state of the tow 12a while being opened is the stretched state between the pre-tensioning unit 25 and the blooming unit 26.

The wrap sheet 14 used in the present embodiment has a width enough to cover both the upper and lower sides of the web 12. After the absorbent polymer 13 is supplied to the web 12, both side portions 14a of the wrap sheet 14 extending from both edges of the web 12 are folded to cover the upper side of the web 12 by the folding mechanism 7 as illustrated in FIG. 4. The wrap sheet 14 can be of any material conventionally used to wrap an absorbent core.

The continuous-form absorbent member 100 is then compressed to cut the continuous fibers by the continuous fiber cutting mechanism 8. The compression and the resultant fiber cutting are achieved by introducing the continuous-form absorbent member 100 into the nip of the pair of rollers 80 and 81 to press a part or the whole of the area of the web 12 where the absorbent polymer 13 has been spread in the thickness direction.

Figure 5:
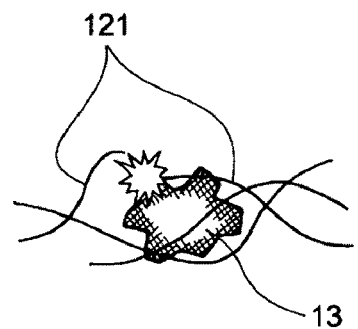
FIG. 5 is an illustration of a continuous fiber being cut by an absorbent polymer.

The continuous fiber cutting takes place within a region in which the absorbent polymer 13 has been spread and which is pressed between the peripheral surface 80M of one of the rollers (the roller 80) made of an elastic material and the peripheral surface of the other roller (the roller 81) made of a hard material. As illustrated in FIG. 5, the continuous fibers 121 are pressed onto the lumpy absorbent polymer particles 13 and cut thereby.

The continuous-form absorbent member 100 having the continuous fibers in part of the web 12 cut is then cut by the continuous-form absorbent member cutting mechanism 5 into individual absorbent members 10 of a size appropriate to the type and size of an absorbent article in which the resulting absorbent member is assembled.

According to the method of the present embodiment, the absorbent member 10 having the aforementioned structure can be produced efficiently and continuously.

Examples of the absorbent article in which the absorbent member of the invention is assembled include disposable diapers, sanitary napkins, panty liners, and incontinence pads. Usually, the absorbent article has a liquid permeable topsheet, a liquid impermeable or water repellent backsheet, and an absorbent member interposed between these sheets.

According to the method of producing the absorbent member 10 according to the present embodiment, an absorbent member having a portion with excellent downward wicking properties in any desired site can be produced with good efficiency by appropriately selecting the area of spreading the lumpy absorbent polymer and the area of cutting the continuous fibers by compressing.

While in the foregoing method of making the absorbent member the step of cutting the continuous fibers by means of a compressing roller is preceded by spreading the absorbent polymer on the continuous fiber web, the same effect is obtained when the continuous fibers are previously cut before the absorbent polymer is spread. In this case, the continuous fibers are cut by a known method, for example, introducing the web into the bite between rollers having a number of slits or cutting the web with a cutter blade, a water jet, a laser beam, etc. The continuous fiber web with part of the continuous fibers cut can be transported on a conveyor, etc. as such because the cut fibers are entangled with each other because of their crimps.

FIGS. 6(a) through 6(e) are each a schematic representing another embodiment of the absorbent member according to the invention. In FIGS. 6(a) to 6(e), a region RA hatched with solid lines from top left to bottom right is the area where the absorbent polymer is spread (equal to the distribution range of the absorbent polymer), and a region RB hatched with dotted lines from top right to bottom left is the area of the web 12 that is compressed to produce staple fibers of continuous fiber origin.

Figure 6A:
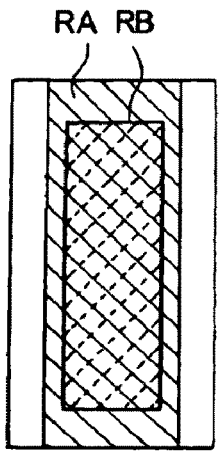
FIG. 6(a), FIG. 6(b), FIG. 6(c), FIG. 6(d), and FIG. 6(e) are each a schematic plan representing another embodiment of the absorbent member according to the invention.

In the absorbent member shown in FIG. 6(a), the region RB having staple fibers is included in the region RA having the absorbent polymer distributed. More specifically, the region RB having staple fibers is narrower than the region RA having the absorbent polymer distributed in both the longitudinal and lateral directions of the absorbent member.

The absorbent member of FIG. 6(a) is produced by the above-described method of producing an absorbent member in which the roller 80 is a roller having a cutting section made of an elastic material and a non-cutting section made of a hard material such as a metal (inelastic material) alternating with each other in the circumferential direction on the peripheral surface thereof. The width of the cutting section in the direction perpendicular to the web 12 is smaller than the width of the polymer feed port in the same direction. The part of the continuous fibers pressed between the elastic material-made cutting section of the roller 80 and the hard material-made peripheral surface of the roller 81 are cut. The metal-made non-cutting section may be replaced with a recess between adjacent cutting sections. The recess serves as a non-cutting section where the continuous fibers are not cut.

Figure 6B:
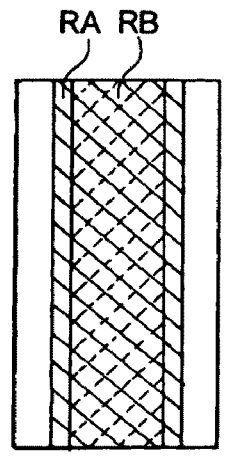

In the absorbent member shown in FIG. 6(b), too, the region RB having staple fibers is included in the region RA having the absorbent polymer distributed. More specifically, the width of the region RB having staple fibers is smaller than that of the region RA having the absorbent polymer distributed in the width direction of the absorbent member, while the region RA having the absorbent polymer distributed and the region RB having the staple fibers have the same length in the longitudinal direction of the absorbent member.

The absorbent member of FIG. 6(b) is obtained by the above-described method of producing an absorbent member in which the roller 80 is a roller of which the elastic material-made peripheral surface 80M has a smaller width than the polymer feed port in the direction perpendicular to the web 12.

Figure 6C:
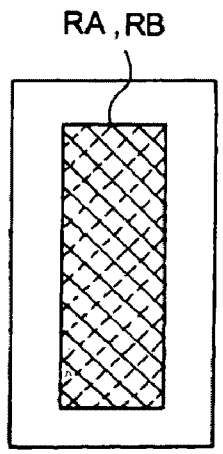

In the absorbent member shown in FIG. 6(c), the region RA having the absorbent polymer distributed and the region RB having the staple fibers coincide with each other. The absorbent member of FIG. 6(c) is prepared by the above-described method of producing an absorbent member in which the absorbent polymer is spread intermittently and in which the roller 80 is a roller having an elastic material-made cutting section and a non-cutting section (i.e., a hard material-made (inelastic material-made) section or a recess) alternating with each other in the circumferential direction on the peripheral surface thereof. The width of the cutting section in the direction perpendicular to the web 12 is equal to the width of the polymer feed port in the same direction.

Figure 6D:
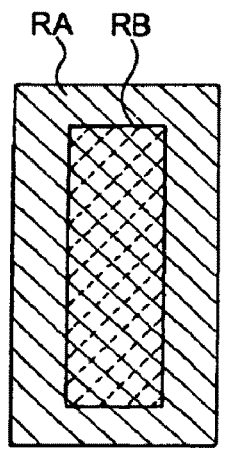
Figure 6E:
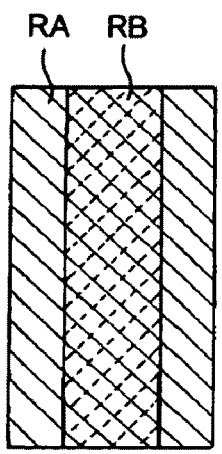

In the absorbent members illustrated in FIGS. 6(d) and 6(e), the region RB having the staple fibers is narrower than the region RA having the absorbent polymer distributed. The absorbent member of FIG. 6(d) is obtained by the above-described method of producing an absorbent member in which the absorbent polymer is spread over the entire area of the web and in which the roller 80 is a roller having a cutting section made of an elastic material and a non-cutting section made of a hard material (inelastic material) or a recessed non-cutting section alternating with each other in the circumferential direction on the peripheral surface thereof, the cutting section having the same width as the polymer feed port in the direction perpendicular to the web 12. The absorbent member of FIG. 6(e) is prepared by the above-described method of producing an absorbent member in which the absorbent polymer is spread over the entire area of the web and in which the roller 80 is a roller having a continuous cutting section made of an elastic material in the circumferential direction on the peripheral surface thereof, the cutting section having the same width as the polymer feed port in the direction perpendicular to the web 12. In FIGS. 6(d) and 6(e), the continuous fibers are present in the area other than the region RB.

The absorbent member of the present invention may be designed to have a front and a rear end portion thereof composed of the continuous fibers and have numerous staple fibers of continuous fiber origin disposed between the front and the rear end portions as in the examples illustrated in FIGS. 6(a), 6(c), and 6(d). In such cases, it is preferred that the absorbent member have the continuous fibers disposed in both the lateral side portions thereof such that the portion having the staple fibers is surrounded by the portion having the continuous fibers. It is not essential, nevertheless, for the absorbent member to have continuous fibers on both lateral side portions thereof.

The absorbent member having any of the configurations of FIGS. 6(a) through 6(d) exhibits excellent downward wicking properties in the region RB where staple fibers have been created. When assembled into an absorbent article such as a disposable diaper or a sanitary napkin with the region RB located in the target zone that is adapted to face a point of body fluid discharge of a wearer, the absorbent member smoothly absorbs a body fluid discharged from the point of discharge (e.g., urine or menstrual blood) through a small planar area and stably retains the fluid in the absorbent polymer localized in that area. When a considerable quantity of a fluid is supplied to or absorbed by the absorbent member to reach the lateral side portions of the absorbent member, the fluid well diffuses in the longitudinal direction of the absorbent member (the front-to-rear direction of a wearer) along the continuous fibers oriented in the longitudinal direction of the absorbent member. As a result, a large area of the absorbent member can be made effective use of, while diffusion of the fluid across the absorbent member is suppressed.

Figure 7:
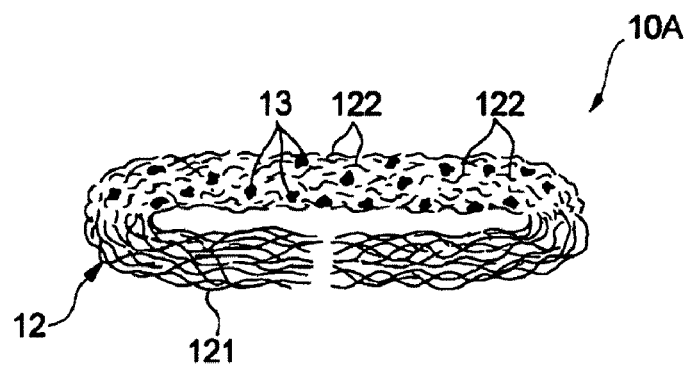
FIG. 7 is a cross-section of still another embodiment of the absorbent member according to the invention (equivalent to FIG. 2).

FIG. 7 illustrates an absorbent member according to still another embodiment of the present invention. An absorbent member 10A shown in FIG. 7 has lumpy absorbent polymer particles 13 unevenly distributed across the thickness direction, that is, the lumpy absorbent polymer 13 is localized in one of the upper and lower sides of the absorbent member. The continuous fibers in substantially the whole planar area of the part having the one-sided distribution of the absorbent polymer 13 are cut into a large number of staple fibers 122.

The absorbent member 10A is obtained by providing a continuous fiber web the width of which is double that of the absorbent member 10A, spreading the absorbent polymer 13 in the laterally middle region of the web, compressing the middle region between an elastic material member and a metallic member to cut the continuous fibers in that region into the staple fibers 122, and folding the side regions outboard of the middle region over the middle region to cover the middle region.

The absorbent member 10A is preferably assembled into an absorbent article such that the side where the lumpy absorbent polymer particles 13 are localized may face the skin of a wearer.

Figure 8:
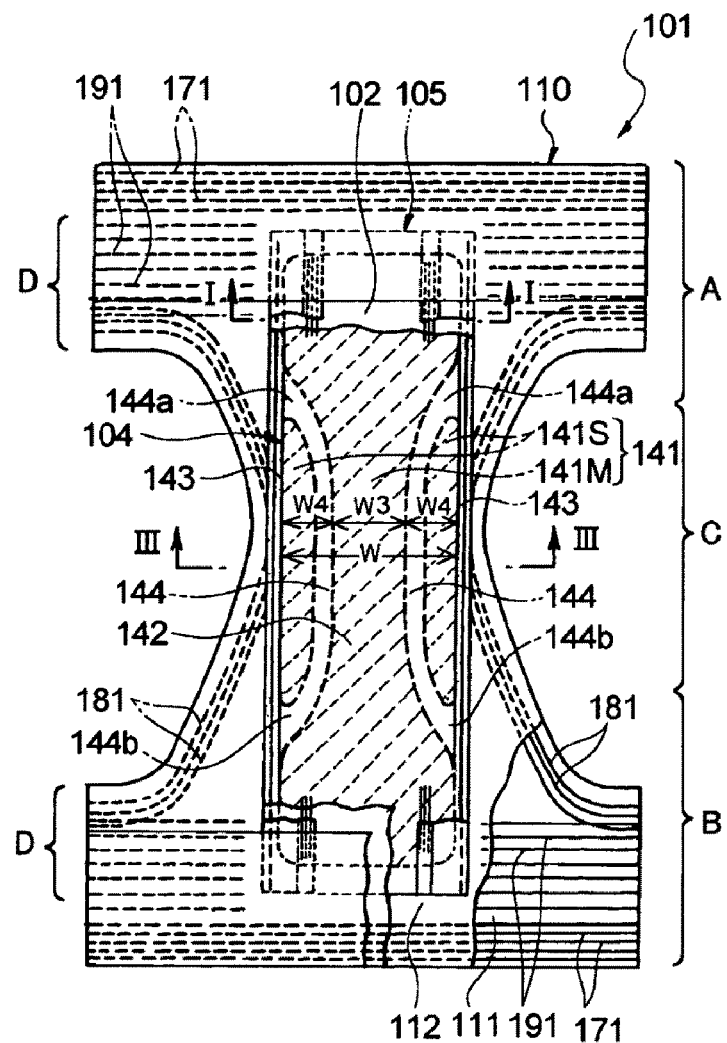
FIG. 8 is a developed plan of a disposable diaper (an embodiment of the absorbent article of the invention) in which a still another embodiment of the absorbent member according to the invention is used.
Figure 9:
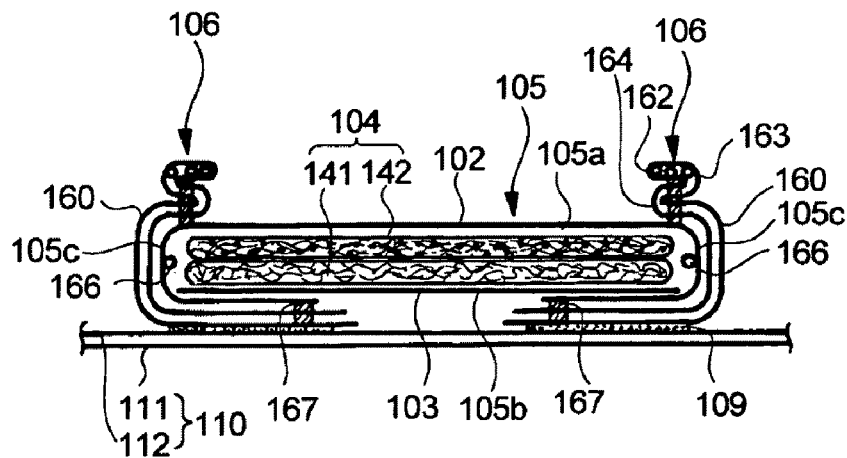
FIG. 9 is a schematic cross-section taken along line I-I in FIG. 8.
Figure 10:
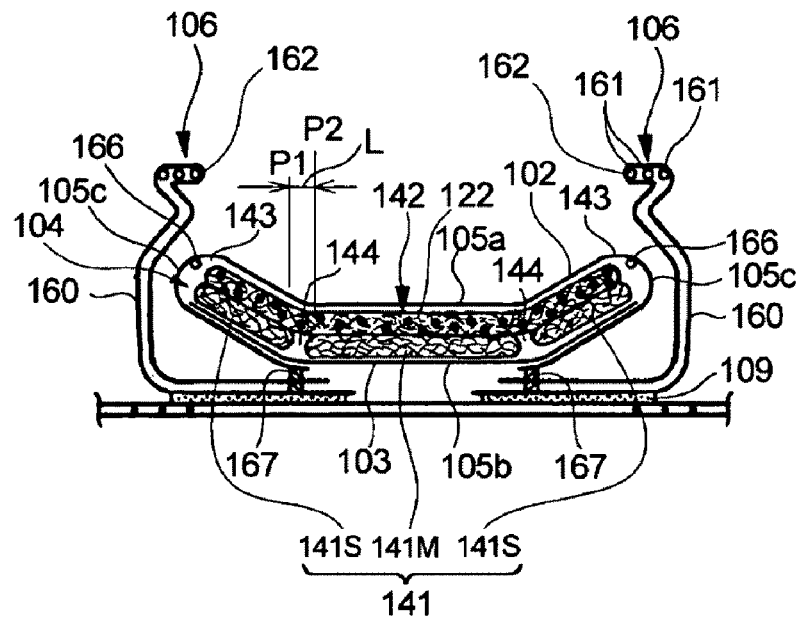
FIG. 10 is a schematic cross-section taken along line III-III of the absorbent member shown in FIG. 8 during use.

FIGS. 8 through 10 represent a pull-on diaper 101 having assembled therein an absorbent member 104 according to yet another embodiment of the present invention. The disposable diaper 101 represents one of preferred embodiments of the absorbent article according to the invention.

The disposable diaper 101 includes an absorbent assembly 105 and an outer cover 110. The absorbent assembly 105 has a liquid permeable topsheet 102, a liquid impermeable or water repellent backsheet 103, and a liquid retentive absorbent member 101 interposed between the topsheet 102 and the backsheet 103. The outer cover 110 has both the side edges of its stomach section A and both the side edges of its back section B joined to each other to make the shape of a pair of pants with a waist opening and a pair of leg openings. FIG. 8 is a developed plan view of the diaper with its side joints cut apart and with all the elastic members used in various parts stretched out flat.

The outer cover 110 is composed of two sheets 111 and 112 and elastic members fixed at the respective positions between the two sheets. As illustrated in FIG. 8, the disposable diaper 101 has waist elastic members 171 that form waist gathers along the edge of the waist opening, leg elastic members 181 that form leg gathers along the edge of each leg opening, and below-waist elastic members 191 that form below-waist gathers in the below-waist portion D (a portion from 20 mm below the edge of the waist opening to the upper end of each leg opening) in two regions separate in the lateral direction. All of these elastic members 171, 181, 191 are fixed between the sheets 111 and 112 in their stretched state with a hot-melt adhesive or a like bonding means. The sheet 111 extends from both the front and the rear ends of the sheet 112, and, after the absorbent assembly 105 is disposed on the sheet 112 of the outer cover 110, the extensions are folded back over and bonded to the absorbent assembly 105 to wrap around the respective ends of the absorbent assembly 105.

As illustrated in FIGS. 8 to 10, the absorbent member 104 of the present embodiment includes a first absorbent core 141 that constitutes the garment-facing side of the absorbent member 104 and a second absorbent core 142 that constitutes the opposite, skin-facing side. The first absorbent core 141 is disposed on the garment-facing side of the second absorbent core 142.

The absorbent member 104 of the present embodiment contains, in its second absorbent core 142, a continuous fiber web and lumpy particles distributed in the web. A large number of staple fibers are present as a result of cutting the continuous fibers in at least part of the region in a planar direction of the web where the particles are distributed.

The second absorbent core 142 is a rectangle in a plan view extending over substantially the whole length of the absorbent assembly 105 inclusive of the absorbent member 104 and being slightly narrower than the width of the absorbent assembly 105.

The first absorbent core 142 is generally rectangular in a plan view but has missing parts 144 in both lateral side portions thereof in the crotch section C of the diaper 101. The missing parts 144 facilitate deforming the absorbent member 104 into a three-dimensional shape. The absorbent member 104 typically undergoes a deformation in the lateral direction to form a dished cross-section taken in the transverse direction of the diaper (e.g., the cross-section shown in FIG. 10), or a deformation in the longitudinal direction of the diaper to form a dished cross-section taken in the longitudinal direction of the diaper, or combination of these deformations.

In the present embodiment, each of the missing parts 144 of the first absorbent core 141 is along the longitudinal direction of the absorbent member 104 at a position away from the edge 143 of the absorbent member 104 in the crotch section C of the diaper.

The language "away from the edge 143 of the absorbent member 104 in the crotch section C of the diaper" used to describe the position of forming the missing parts 144 is intended to mean that the missing parts 144 are away from the respective edges 143 in at least the longitudinally central position of the diaper. The term "longitudinally central position of the diaper" denotes a position at which the total length of the diaper in its developed and stretched out state is divided into equal halves, which position is indicated by line III-III in FIG. 8.

As illustrated in FIG. 8, each of the missing parts 144 in the first absorbent core 141 has longitudinal ends 144a and 144b both of which are open on the respective side edges 143 of the absorbent member 104. To put it another way, the first absorbent core 141 is divided into three pieces: a middle piece 141M that is located in the lateral middle of the absorbent member 104 in at least the crotch section C and a pair of side pieces 141S that are on opposite sides of the middle piece 141M in the crotch section C. The term "missing part" as used herein is intended to include a gap created between divided pieces like the missing parts 144 in the present embodiment.

The absorbent member 104 of the present embodiment has a countless number of staple fibers in the laterally middle portion of the second absorbent core 142 in the crotch section C of the diaper 101, which portion corresponds to the target zone of the diaper 101. More specifically, staple fibers of continuous fiber origin exist in the portion of the second absorbent core that overlies the portion of the first absorbent core 141 located between the opposing missing parts 144 (a part of the middle piece 141M). Thus, the target zone of the diaper 101 has enhanced downward wicking properties to provide ensured prevention of leakage and to reduce an uncomfortable sticky feel. On the other hand, the portions of the continuous fiber web overlying the side pieces 141S have the constituent continuous fibers 121 remaining non-cut, thereby preventing a fluid from further spreading in the lateral direction of the diaper and providing improved protection against side leakage.

In an modified embodiment, the staple fibers of continuous fiber origin may exist in both the portion overlying the portion of the first absorbent core 141 located between the opposite missing parts 144 (a part of the middle piece 141M) and the portions overlying the side pieces 141S, while the portions overlying the missing parts 144 have the continuous fibers 121 remaining continuous (non-cut). In this case, too, the same effects as by the above-mentioned diaper can be obtained.

As illustrated in FIGS. 9 and 10, the first absorbent core 141 of the present embodiment is superposed on the garment-facing side of the second absorbent core 142. Accordingly, both the missing parts 144 of the first absorbent core 141 are under the second absorbent core 142. The term "skin facing side" as used with respect to an absorbent member is the side of the absorbent member that is adapted to face the skin of a wearer while worn, and the term "garment facing side" as used for an absorbent member is the side of the absorbent member that is adapted to face opposite to the skin of a wearer.

Having the missing parts 144, the absorbent member 104 according to the present embodiment has improved deformability into a three-dimensional shape. Specifically, both the side portions of the absorbent member 104, i.e., the portions located on both sides of the middle piece 141M of the first absorbent core easily rise toward the wearer's skin while the diaper is worn as illustrated in FIG. 10.

It is preferred that the distance W4 (see FIG. 8) between the side edge 143 of the absorbent member and the missing part 144 (the inboard end of the missing part 144) be 10% to 40%, more preferably 20% to 30%, of the width W (see FIG. 8) of the absorbent member 104. This is advantageous for the side portions of the absorbent member 104 to rise in a good fashion to form an ideal three-dimensional shape that can wrap around the point of discharge and for the middle piece 141M located in the laterally middle portion of the absorbent member 104 to prevent the absorbing member from bunching up in the crotch section. The distance W3 (see FIG. 8) between the opposite missing parts 144 is preferably 20 to 120 mm, more preferably 40 to 100 mm.

The width of each missing part 144 in the diaper width direction is preferably 3 to 20 mm, more preferably 5 to 15 mm. The length of the missing part 144 in the diaper's longitudinal direction (which is equal to the length of the side piece 141S in the diaper's longitudinal direction in the present embodiment) is preferably 10 to 35 cm, more preferably 15 to 30 cm, in the case of diapers for children and 15 to 55 cm, more preferably 20 to 50 cm, in the case of diapers for adults.

The second absorbent core 142 has a smaller bending stiffness than the first absorbent core 141 in the diaper width direction.

The bending stiffness of the second absorbent core 142 in the diaper width direction is preferably smaller than that of the first absorbent core 141 by 10 to 50 g, more preferably by 20 to 40 g. The bending stiffness of the second absorbent core 142 in the diaper width direction is preferably 50 g or less, more preferably 40 g or less, and that of the first absorbent core 141 is preferably 30 to 80 g, more preferably 40 to 70 g.

The diaper width direction bending stiffness of the first and the second absorbent core is measured as follows.

Method of Measuring Diaper Width Direction Bending Stiffness:

Bending stiffness can be measured with a handle-o-meter. The measurement with a handle-o-meter is as follows. JIS L1096 (testing methods for woven fabrics) is followed. A 100 mm by 150 mm specimen is cut out of an absorbent member with the width and length coinciding with those of the absorbent member. The specimen is placed on the platform having a 30 mm wide slot with the length perpendicular to the slot. A 2 mm thick penetrator blade presses the center of the specimen into the slot, and the resistance (g) to 8 mm penetration from the slot is measured through a load cell. In the present invention, a handle-o-meter HOM-2 available from Daiei Kagaku Seiki Co., Ltd. was used. The measurement is made on three points to obtain an average.

The absorbent member 104 in the present embodiment has a generally rectangular shape that is elongated in the front-to-rear direction of the diaper in a plan view. The absorbent member 104 is totally wrapped in a water-pervious wrap sheet (not shown) made of tissue paper or water-pervious nonwoven fabric and fixed between the topsheet 102 and the backsheet 103.

In the diaper 101 of the present embodiment, the topsheet 102 extends from both side edges of the absorbent member 104, and the extensions are folded to the garment facing side of the absorbent member 104 and fixed to the backsheet 103 via an adhesive (not shown), etc. on the garment facing side of the absorbent member.

The first absorbent core 141 and the second absorbent core 142 may be individually wrapped in the respective wrap sheets. The first absorbent core 141 and the second absorbent core 142 may or may not be joined in parts with an adhesive, etc.

The disposable diaper 101 further includes a pair of anti-leakage cuffs 106 extending in the diaper length direction on both lateral sides of the absorbent assembly 105. As shown in FIGS. 9 and 10, each of the anti-leakage cuffs 106 is formed of a cuff-forming sheet 160 and elastic members 161 fixed to the cuff-forming sheet 160 in their stretched state.

Each of the cuff-forming sheet 160 is preferably disposed to cover the side edge face 105c of the absorbent assembly 105. The phrase "cover the side edge face of the absorbent assembly 105" as used herein means that the cuff-forming sheet 160 forms a standing anti-leakage cuff in the crotch portion of the diaper so as to make it less likely for the side edge face of the absorbent assembly to come into direct contact with the wearer's skin.

More specifically, with the diaper 101 being in a developed and stretched out state (see FIG. 8), the cuff-forming sheet 160 preferably straddles the side edge face of the absorbent assembly 105 with one end on the skin facing side 105a of the absorbent assembly 105 and the other on the garment facing side 105b in the stomach section A and the back section B (and preferably the crotch section C) of the diaper 101. The cuff-forming sheet 160 is preferably fixed to the skin facing side 105a of the absorbent assembly 105 in the stomach section A and the back section B. Being so designed, the anti-leakage cuffs are ready to wrap around the respective side edge faces of the absorbent assembly to provide improved protection against leakage. The term "skin facing side 105a" is the side of the absorbent assembly 105 that is adapted to face the skin of a wearer while worn, and the term "garment facing side 105b" is the side of the absorbent assembly 105 that is adapted to face opposite to the skin of a wearer.

As shown in FIG. 10, the anti-leakage cuffs 106 are able to stand in at least the crotch section C. Each anti-leakage cuff 106 has elastic members 161 fixed along its free end 162. In the stomach section A and the back section B, the anti-leakage cuff 106 is folded into three along folding lines 163 and 164 and fixed to the skin facing side of the absorbent assembly 105 by a known bonding means such as heat sealing or an adhesive.

The cuff-forming sheet 160 used in the disposable diaper 101 is an elongated rectangular, water-repellent sheet having a predetermined width that is folded into two panels along a longitudinal folding line, the facing two panels being bonded with a hot melt adhesive or by partial heat or ultrasonic sealing. The elastic members 161 are fixed in their stretched state between the facing two panels.

As illustrated in FIG. 10, the cuff-forming sheet 160 is fixed to the absorbent assembly 105 in the crotch section C at a position inboard of the side edge face 105c of the absorbent assembly 105 to form a joint 167. The joint 167 provides a fixed end of the anti-leakage cuff 106. The joint 167 is formed by bonding the cuff-forming sheet 160 and the extended and folded-over portion of the topsheet 102 by a known bonding means such as heat sealing, high frequency sealing, ultrasonic sealing, or a hot-melt adhesive.

The absorbent assembly 105 has an elastic member 166 for raising each side portion thereof attached in its stretched state along a position outboard of each of the joints 167. The elastic member 166 is disposed along each lateral side edge of the absorbent assembly 105 to straddle the stomach section A and the back section B. While in the diaper 101 of the present embodiment, the elastic member 166 is arranged along each side edge of the absorbent assembly 105, the position of the elastic member 166 is not limited thereto as long as it is outboard of the joint 167. For example, the elastic member 166 may be disposed between the absorbent member 104 and the part of the topsheet 102 lying on the skin facing side of the absorbent member 104, between the absorbent member 104 and the backsheet 103, or on the inner side of the wrap sheet (not shown) wrapping the absorbent member 104. The elastic member 166 may be provided at two or more of these positions. It is preferred, nevertheless, to provide the elastic member 166 on or near both side edges of the absorbent assembly 105.

The joint 167 on each side is preferably about 5 to 50 mm, more preferably about 10 to 30 mm, inboard from the side edge face 105c of the absorbent assembly 105.

It is preferred that the position P1 of the fixed end of the anti-leakage cuff 106 and the position P2 of the missing part 144 (the position of the inboard end of the missing part 144) in the width direction in the crotch section C of the diaper 101 be substantially coincident with each other as illustrated in FIG. 10. The fixed end of the anti-leakage cuff 106 is the part where the cuff-forming sheet 160 is bonded to the absorbent assembly 105 at the end opposite to the free end of the anti-leakage cuff 106. The positions P1 and P2 substantially coinciding with each other, the side portions of the absorbent assembly 5 rise more satisfactorily to form an ideal three-dimensional shape that can wrap around the point of discharge to provide better protection against leakage.

Taking precision errors during the production into consideration, the expression "the positions P1 and P2 substantially coincide with each other" includes not only complete coincidence but also a situation in which the positions P1 and P2 are out of alignment by a distance L (see FIG. 10) up to 10 mm.

All the previously recited preferred ranges of the distance W4 between the side edge 143 of the absorbent member 104 and the missing part 144, the width W of the absorbent member, the distance W3 between the opposite missing parts 144, the width of each missing part, the distance between the joints 167 and the respective side edges 105c of the absorbent assembly 105, and the distance between the positions P1 and P2 are the values measured at the longitudinally middle position of the diaper.

According to the structure of the disposable diaper 101 of the present embodiment, as shown in FIG. 10 both side portions of the absorbent member 104 or the absorbent assembly 105 rise to form a dish shape concave to the skin owing to the easy-to-rise configuration of the side portions of the absorbent member 104, the presence of the elastic members 166, and the specific location of the joints between the absorbent assembly 105 and the cuff-forming sheets 160. The dished shape holds body wastes. Even when a large quantity of urine is discharged in a short time or a hard-to-absorb waste such as watery or loose stool is discharged, the dished shape hardly allows the waste to leak. Should a leakage occur from the dished shape, leakage from the diaper can be blocked by the anti-leakage cuffs 106 wrapping around the side edges of the absorbent assembly 105. That is, even if a body waste runs off the edge of the side portion of the absorbent assembly in the crotch section, the diaper exhibits excellent anti-leakage performance because the anti-leakage cuffs 106 standing outboard the absorbent assembly blocks further running of the waste. In addition, the presence of the anti-leakage cuffs 106 makes it less likely for the side edge of the absorbent assembly to come into direct contact with the wearer's skin. This prevents discomfort during wear.

The crotch section C is inwardly laterally compressed easily from both sides with the motion of the wearer. Because the compressive force applied to the crotch section C from both sides by the motion of the wearer is relaxed by the rising of the side portions of the absorbent member 104, the absorbent member 104 exhibits improved resistance to bunching or roping.

In cases when the missing part 144 widens due to, e.g., the wearer's motion of spreading out his or her legs or twisting the upper body to separate the middle piece 141M of the first absorbent core 141 (the piece located in the lateral middle of the first absorbent core 141) and the side portion of the absorbent member further apart, the widened gap between the middle piece 141M and the side portion of the first absorbent core 141 is duly covered with the less stiff second absorbent core 142 so as to prevent leakage through the gap because the second absorbent core 142 overlies the missing parts 44 of the first absorbent core 141.

The disposable diaper 101 according to the present embodiment provides markedly improved protection against side leakage. This allows for reducing the width of the absorbent assembly or the width of the crotch section C to provide a better fit while retaining the improvement of anti-leakage performance or minimizing reduction of anti-leakage performance. In this case, the pair of anti-leakage cuffs 106 rise upright to the wearer's skin to secure a sufficient height and is, if collapsed, less likely to narrow the effective area of absorption, so that the above effect is further ensured.

As compared with an absorbent member having continuous fibers, the absorbent member having staple fibers in the second absorbent core raises its side portions more easily with no tightening of fibers as well as exhibiting downward wicking properties in its middle region. The absorbent member thus exhibits further improved prevention against side leakage. It is therefore preferred that the staple fibers or the lumpy particles used to produce the staple fibers be localized in the laterally middle region of the second absorbent core.

A disposable diaper satisfying the following conditions is a preferred example of a diaper having such a reduced width of the crotch section. The maximum width of the absorbent member 104 is 60 to 140 mm, more preferably 80 to 120 mm, in the stomach section A and the back section B and 50 to 140 mm, more preferably 70 to 120 mm, in the crotch section C.

In FIGS. 9 and 10 the reference numeral 109 indicates an adhesive bonding the absorbent assembly 105 and the outer cover 110.

The first absorbent core 141 used in the present embodiment is preferably designed such that a fluid spreads faster in the diaper width direction than in the diaper length direction so as to take more time to reach the front end of the diaper thereby to provide better protection against leakage from the front end.

A rate of fluid spreading in a certain direction could be increased by forming a directional channel, e.g., by embossing but is preferably increased by aligning the constituent fibers in that direction. In which of the width and the length directions the rate of fluid spreading is higher (a fluid spreads faster) can be determined by comparing Klemm absorption heights of specimens cut out along the width and the length directions of a sample.

FIGS. 13 through 17 illustrate other embodiments of the absorbent member according to the present invention. Each of the absorbent members 10B to 10F shown in FIGS. 13 to 17 contains staple fibers in the hatched region.

The absorbent member 10B illustrated in FIGS. 13(a) and 13(b) is composed of an absorbent core 9 and a wrap sheet (not shown) wrapping the absorbent core 9. The absorbent core 9 is a dual layered fiber aggregate composed of an upper fiber layer 91 made mainly of staple fibers and a lower fiber layer 92 made mainly of continuous fibers. The wrap sheet covers the upper and lower sides and both side edge faces of the absorbent core 9 in the same manner as in the absorbent member 10 shown in FIGS. 1 and 2. The absorbent member including "a fiber aggregate containing continuous fibers and synthetic or semisynthetic staple fibers" can be such an absorbent core having a fiber aggregate wrapped in a wrap sheet like the absorbent member 10B.

The staple fibers in the absorbent member 10B are localized in the upper fiber layer 91 that is adapted to face the skin of a wearer as assembled into an absorbent article, while the continuous fibers are localized in the lower fiber layer 92 that is adapted to face the opposite side to the skin facing side. In other words, the continuous fibers and the staple fibers are localized in different positions in the thickness direction of the absorbent member.

The upper fiber layer 91 preferably contains staple fibers having a fiber length less than 70 mm in a proportion of 50% to 100%, more preferably 60% to 100%, even more preferably 80% to 100%, by weight based on the total fibers constituting the upper fiber layer 91. The lower layer fiber 92 preferably contains continuous fibers having a fiber length more than 70 mm in a proportion of 50% to 100%, more preferably 60% to 100%, even more preferably 80% to 100%, by weight based on the total fibers making up the lower layer fiber 92.

The absorbent member 10B of FIGS. 13(a) and 13(b) exhibits excellent downward wicking properties in its upper fiber layer 91 containing the staple fibers. Therefore, an absorbent article such as a disposable diaper or a sanitary napkin having the absorbent member 10B incorporated therein with the upper fiber layer 91 facing a point of discharge of a wearer is able to smoothly wick a body fluid (e.g., urine or menstrual blood) discharged from a point of discharge through a small area of the absorbent member. When a considerable quantity of a fluid is supplied to or absorbed by the absorbent member to reach the lateral side portions of the absorbent member or the garment-facing surface of the upper fiber layer 91, the fluid well diffuses in the longitudinal direction of the absorbent member (the front-to-rear direction of a wearer) along the continuous fibers oriented in the longitudinal direction of the absorbent member. As a result, a large area of the absorbent member can be made effective use of, while spread of the fluid across the absorbent member is suppressed to provide excellent protection against side leakage.

While in the absorbent member 10B the upper fiber layer 91 is narrower than the lower fiber layer 92, the upper fiber layer 91 and the lower fiber layer 92 may have substantially the same width.

Each of the absorbent members 10C to 10F shown in FIGS. 14 through 17 includes an absorbent core 9 formed of a single layered fiber aggregate 93 and a wrap sheet (not shown) wrapping the absorbent core 9. The wrap sheet covers the upper and lower sides of the absorbent core 9. The wrap sheet preferably covers the upper and lower sides of at least a region 9S of the absorbent core 9 where staple fibers are localized.

Each of the absorbent members 10C to 10F shown in FIGS. 14 to 17 has staple fibers localized in the hatched region and continuous fibers localized in the non-hatched region. In other words, the continuous fibers and the staple fibers are localized in different regions in the plane of these absorbent members.

The absorbent member 10C illustrated in FIGS. 14(a) and 14(b) has an absorbent core 9 formed of a fiber aggregate 93. The absorbent core 9 (fiber aggregate 93) has a region 9S where staple fibers are localized as one of the longitudinal end portions and a region 9L where continuous fibers are localized as the other longitudinal end portion. When the absorbent member 10C is assembled in a diaper with its region 9S having the staple fibers straddling the crotch section and the stomach section of the diaper and its region 9L having the continuous fibers disposed in the back section of the diaper, the diaper exhibits excellent downward wicking properties in its crotch section and provides effective protection against leakage from the front end. In contrast, when the absorbent member 10C is assembled the other way around, leakage from the rear end is prevented effectively.

Figures 15A, 15B:
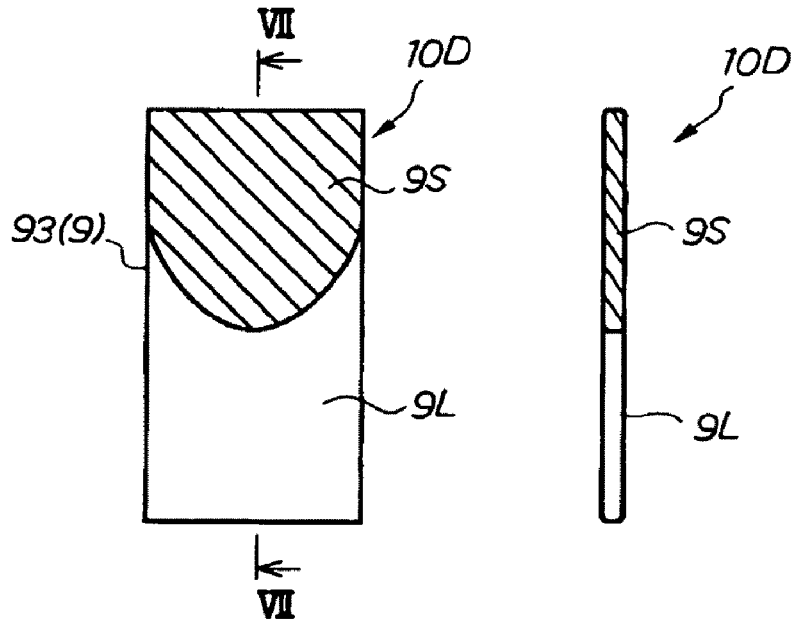

The absorbent member 10D illustrated in FIGS. 15(a) and 15(b) has an absorbent core 9 formed of a fiber aggregate 93. The absorbent core 9 has a horseshoe-shaped region 9S where staple fibers are localized as one of the longitudinal end portions and a region 9L where continuous fibers are localized as the other longitudinal end portion. An absorbent polymer is localized in the region 9S. When the absorbent member 10D is incorporated in a diaper with its region 9L located so as to face the back of a wearer, the diaper absorbs urine preferentially in its stomach side and has the urine retained by the absorbent polymer present in the stomach side. As a result, the region 9S increases in thickness, which serves to prevent loose stool from flowing to the front of the wearer.

Figure 16A:
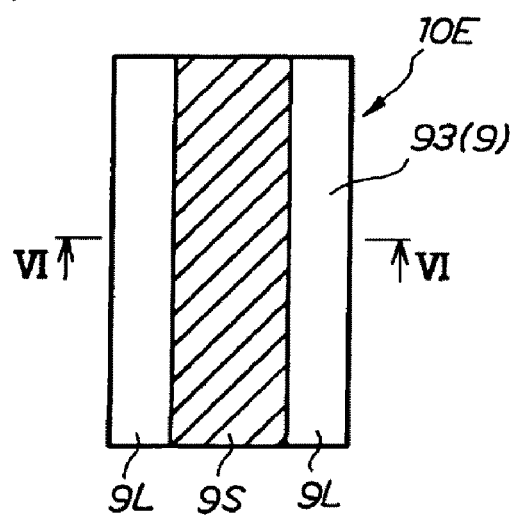
Figure 16B:
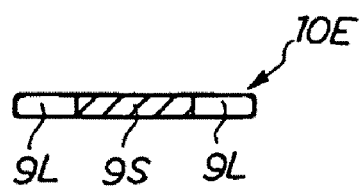

The absorbent member 10E illustrated in FIGS. 16(a) and 16(b) has an absorbent core 9 formed of a fiber aggregate 93. The absorbent core 9 has a region 9S where staple fibers are localized in its laterally middle portion and a region 9L where continuous fibers are localized on each lateral side of the region 9S. The part of the fiber aggregate 93 where staple fibers are localized, i.e., the region 9S preferably contains staple fibers having a fiber length less than 70 mm in a proportion of 50% to 100%, more preferably 60% to 100%, even more preferably 80% to 100%, by weight based on the total fibers constituting the region 9S. The preferred proportion (inclusive of the more preferred and even more preferred ranges) of the staple fibers recited above applies to the similar region in the absorbent member 10 shown in FIGS. 1 and 2 (namely, the part of the continuous fiber web 12 which is located in the middle region M of the absorbent member 10) and in the above-described absorbent members 10C and 10D. The region 9L of the fiber aggregate 93 having continuous fibers localized therein and containing substantially no or only a small amount of staple fibers compared with the region 9S preferably contains continuous fibers having a fiber length more than 70 mm in a proportion of 50% to 100%, more preferably 60% to 100%, even more preferably 80% to 100%, by weight based on the total fibers making up the region 9L.

The configuration of the absorbent member 10E shown in FIGS. 16(a) and 16(b) produces the same effects as by the absorbent member 10 of FIGS. 1 and 2. Similarly to the aforementioned absorbent member 104, the absorbent member 10E, when incorporated into a diaper with its longitudinal direction coinciding with the front-to-rear direction of the diaper, easily raises both side portions thereof toward the skin of a wearer with the aid of elastic members to form barriers against side leakage. The elastic member for raising the side portions of the absorbent member 10E may be disposed, e.g., on the skin-facing side or the garment-facing side of the absorbent member 10E, near both the side edges of the absorbent member 10E, or inside the absorbent member 10.

Figure 17A:
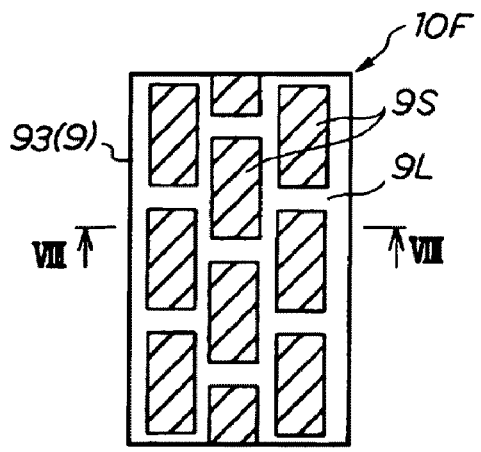
Figure 17B:
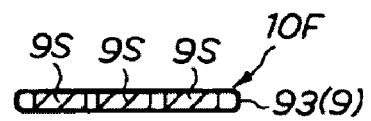
Figure 17C:
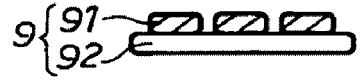

The absorbent member 10F in FIGS. 17(a) to 17(c) has an absorbent core 9 formed of a fiber aggregate 93. The absorbent core 9 has regions 9S containing staple fibers discretely arranged therein. A plurality of the staple fiber-containing regions, being discretely arranged in either a random or a regular pattern, quickly absorb a fluid, swell, and bulge out. The bulges thus formed serve to maintain ventilation between the skin and the diaper even after the swelling. While in FIG. 17(b) the staple fiber-containing regions 9S are discretely arranged in the fiber aggregate flush with the upper surface of the fiber aggregate, the absorbent core 9 may be composed of fiber layers 91 and 92, of which the layer 92 is made mainly of continuous fibers, and the layer 91 is made mainly of staple fibers and is divided into a number of discrete pieces as illustrated in FIG. 17(c).

The staple fiber-containing regions 9S contains a large amount of an absorbent polymer compared with the region 9L containing only a small amount of staple fibers. The absorbent polymer weight ratio is 9S/9L=10/1 to 1.5/1 by weight. It is rather preferred that an absorbent polymer be substantially absent in the region 9L containing only a small amount of staple fibers. The phrase "substantially absent" as used herein means that the ratio of the absorbent polymer content in the region 9L to that in the region 9S is less than $1/10$. That is, the phrase is intended to include unintentional incorporation of a slight amount of an absorbent polymer, which is intended to be located in the region 9S, into the region 9L in the manufacture of the absorbent member. With the absorbent polymer so located, the region 9S bulges over the region 9L to secure ventilation.

The staple fibers used in all the absorbent members 10B to 10F are synthetic or semisynthetic fibers. Although by and large conventional absorbent members use pulp fiber, use of staple fibers that are not of pulp origin provides an absorbent member that does not collapse when wetted and continues exhibiting downward wicking properties for repeated discharges of a body fluid.

Examples of the synthetic fibers that can be used as staple fibers include polyethylene, polypropylene, polyethylene terephthalate, polybutylene terephthalate, polytetramethylene terephthalate, nylon, acrylic fibers, and vinylon, either alone or in the form of conjugate fiber (e.g., a concentric or eccentric sheath/core configuration or a side-by-side configuration). Examples of semisynthetic fibers that can be used as staple fibers include rayon, cellulose triacetate and/or cellulose diacetate.

The synthetic or semisynthetic fibers enumerated above can be used either individually or as a combination of two or more thereof. The term "synthetic or semisynthetic" as used herein is intended to include a combination of synthetic fibers and semisynthetic fibers.

The absorbent members 10B to 10F are different from the absorbent member 10 of the first embodiment in that the staple fibers contained therein are not those created by cutting continuous fibers using lumpy particles.

The upper fiber layer 91 of the absorbent member 10B shown in FIGS. 13(a) and 13(b) can be formed of a carded web (a web prepared using a carding machine), an air-laid web (a web formed by using an air stream), a wet processed web (a web formed by using water), or the like. The fibers constituting a carded web have the form of staple before being carded. On the other hand, the lower fiber layer 92 of the absorbent member 10B can be formed of a tow-opened web prepared in the same manner as for the aforementioned absorbent member. The lower fiber layer 92 may also be formed of a web prepared by melt spinning (such as a spun-laid web) or a web obtained by splitting a unstretched film or a stretched film of an extruded molten resin.

Figure 18A:
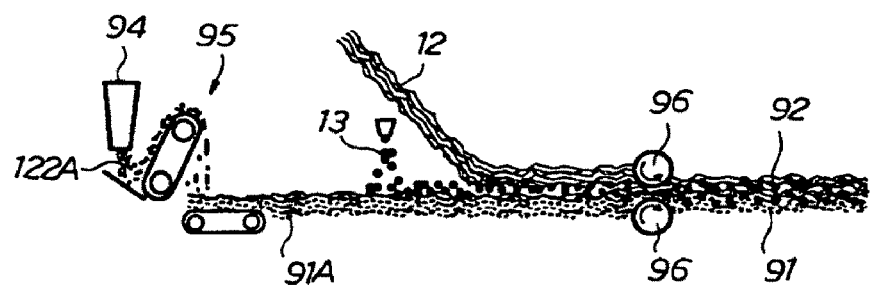
FIG. 18(a) and FIG. 18(b) each illustrate another example of the method of producing the absorbent member according to the invention.

FIG. 18(a) represents an example of a method of producing the absorbent member 10B.

In the method illustrated in FIG. 18(a), staple fibers 122A metered from hopper 94 are fed to carding machine 95, where the staple fibers 122A are carded into a continuous-form web 91A. Non-lumpy absorbent polymer particles 13 are spread on a prescribed part of the web 91A, and a tow-opened, continuous fiber web 12 is superposed on the polymer-spread side of the web 91A. The resulting laminate is passed between a pair of rollers 96 and pressed in its thickness direction. The pressing between the rollers 96 should be conducted under such conditions as to reduce the thickness of the laminate to impart shape retention without causing substantial cutting of the continuous fibers. After being pressed between the rollers 96, the laminate is wrapped in a wrap sheet fed from a wrap sheet feeding mechanism (not shown). The wrapped laminate of continuous form is then cut to length to obtain individual absorbent members 10B in a continuous manner.

In the method described, the absorbent polymer 13 is distributed between the carded web 91A and the continuous fiber web 12. The resulting absorbent member 10B has the absorbent polymer localized on and near the interface between the upper fiber layer 91 and the lower fiber layer 92 in the thickness direction.

Figure 18B:
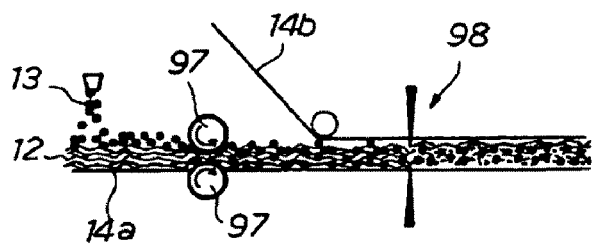

FIG. 18(b) represents an example of the method of producing the absorbent member 10C to 10F.

In the method illustrated in FIG. 18(b), a tow-opened, continuous fiber web 12 is continuously transported as supported by an extensible sheet 14a. Non-lumpy particles of an absorbent polymer 13 are spread on the web 12. The web 12 having the absorbent polymer 13 spread thereon is passed between a pair of rollers 97 to press the polymer particles 13 into the web 12. An extensible sheet 14b is superposed on the opposite side of the web 12 to the polymer-spread side (on the side opposite to the sheet 14a), and the web 12 as sandwiched in between the sheets 14a and 14b is passed through a continuous fiber cutting unit 98 to cut the continuous fibers in part of the web 12.

The continuous fiber cutting unit 98 is designed to cut continuous fibers regardless of the presence or absence of lumpy particles. Such a cutting unit is exemplified by a unit including a pressing member with cutting projections on its peripheral surface or on one side thereof. The pressing member is configured to press the web 12 sandwiched between the sheets 14a and 14b to cut the continuous fibers by the cutting projections thereof. The continuous fiber cutting unit 98 is preferably designed not to cause the cutting projections to make a hole through the extensible sheets 14a and 14b.

Figure 19:
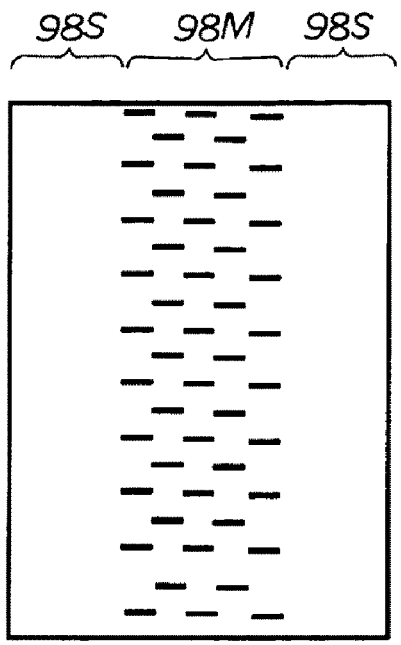
FIG. 19 is a developed plan of the pressing roller used in the method of FIG. 18(b), illustrating an example of arrangement of cutting projections.

In FIG. 19 is illustrated an example of arrangement of the cutting projections of the cutting unit 98 that can be used to make the absorbent member 10E shown in FIGS. 16(a) and 16(b). FIG. 19 is a development view of a pressing roller, showing the pattern of arrangement of the cutting projections on the peripheral surface (the surface of a pressing member). As illustrated in FIG. 19, the pressing roller has cutting projections arranged in a staggered pattern in a portion 98M that corresponds to the laterally middle portion of the web 12. Pressing the web 12 against the portion 98M results in formation of a great number of staple fibers in the middle region of the web 12. Because the cutting projections are not provided in portions 98S that correspond to both the side portions of the web 12, substantially no staple fibers are created in the side portions of the web 12. The absorbent members 10C, 10D, and 10F can be produced in the same manner except for altering the pattern of arranging the cutting projections on the surface of the pressing member.

In still other embodiments of the absorbent member according to the present invention, there are provided absorbent members having any of the configurations shown in FIGS. 14 through 17 in which the staple fibers in the respective hatched regions are created by cutting continuous fibers by the method illustrated in FIG. 4 with an alteration of the pattern for spreading the lumpy particles.

Figure 20:
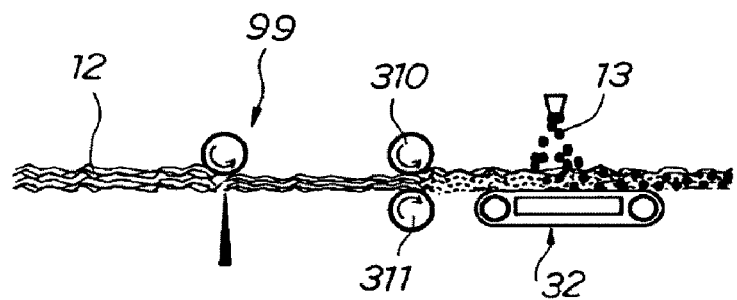
FIG. 20 illustrates a method of producing still another embodiment of the absorbent member according to the invention.

FIG. 20 illustrates a method of producing still another embodiment of the absorbent member according to the present invention.

In the method of FIG. 20, a tow-opened continuous fiber web 12 is fed to a continuous fiber cutting unit 99, where the continuous fibers are cut in part to create stable fibers of continuous fiber origin in part. The web 12 containing the staple fibers and the continuous fibers remaining non-cut is then stretched by a difference in peripheral speed between the cutting unit 99 and a pair of rollers 310 and 311. While the web is being stretched, the continuous fibers that have been cut incompletely are completely separated apart to create staple fibers. The stretched state of the web is relaxed between the pair of rollers 310 and 311 and a vacuum conveyor 32, and an absorbent polymer 13 is fed to the web in the relaxed state while being sucked by the vacuum conveyor 32 from the opposite side of the web. The web having the absorbent polymer is wrapped in a wrap sheet fed from a wrap sheet feeding mechanism (not shown) and cut to the length of individual absorbent members.

Any cutting unit that can cut fibers can be used as the cutting unit 99 with no particular limitation, including a rotary die cutter, a score cut blade, and a laser.

The above-described method produces an absorbent member formed of a fiber aggregate containing both the continuous fibers and the staple fibers of continuous fiber origin in a mixed state.

It is preferred that the fibers constituting the staple fiber-containing fiber aggregate or the continuous fiber web be not bonded to each other so as not to interfere with the absorbent polymer swell. As used herein, the term "bonded" refers to a state in which fibers are united through fusion such that they are not debonded even when the absorbent polymer swells. The term does not include a state in which fibers intertwine or engage with each other or stick to each other via a water-soluble binder so that they are enabled to move relative to one another as a result of loosening of or being freed from, by elimination or by swelling of the absorbent polymer.

While the present invention has been described based on its preferred embodiments, various changes and modifications can be made thereto. For example, the continuous fiber web containing the staple fibers of continuous fiber origin and an absorbent polymer may be used in the form of a laminate with a dry-laid web containing fluff pulp. In that case, the absorbent member shown in FIGS. 1 and 2 or the absorbent member shown in any one of FIGS. 6(a) to 6(e) may be superposed on a dry-laid web containing fluff pulp, and the resulting laminate may be wrapped in a wrap sheet to make an absorbent member. Such an absorbent member is preferably used in an absorbent article with the continuous fiber web 12 facing the skin of a wearer. The first absorbent core 141 in the absorbent member 104 is a fluff pulp-containing dry-laid web.

Examples of the fluff pulp-containing dry-laid web include a dry-laid web made solely of fluff pulp, a mixed dry-laid web made of fluff pulp and absorbent polymer particles, a mixed dry-laid, thermally united web made from fluff pulp and thermally fusible synthetic fibers, a mixed dry-laid, thermally united web made from fluff pulp, absorbent polymer particles, and thermally fusible synthetic fibers, an embossed, dry-laid web of fluff pulp, an embossed, mixed dry-laid web of fluff pulp and absorbent polymer particles, and a mixed dry-laid web made of fluff pulp having been sprayed with water and absorbent polymer particles. The fluff pulp content of the fluff pulp-containing dry-laid web may be 50% to 100% by mass.

While a dual layered absorbent member, such as the absorbent member 10A illustrated in FIG. 7, can be obtained by folding side portions of a wide web over one side of the web, a dual layered absorbent member may be obtained by superposing a continuous fiber web having part of the continuous fibers cut into staple fibers and a continuous fiber web containing no staple fibers of continuous fiber origin.

The absorbent article of the present invention may have the above-described absorbent member 104 replaced with any of the aforementioned other absorbent members. The absorbent article of the invention may be a conventional open type diaper with fasteners as well as a pull-on type diaper. The absorbent member according to the invention may be used as a sublayer to be interposed between an absorbent member having a common structure used in conventional disposable diapers, etc. and a topsheet.

The absorbent article of the invention having the absorbent member according to any of the foregoing preferred embodiments may have two or more pairs of opposing gathers. For example, the absorbent article fragmentally shown in FIG. 11 has an absorbent member 201 and a leg flap 220 that extends laterally outward from each side edge of the absorbent member 201. The leg flap 220 has elastic threads 221 disposed at the side edge thereof in the longitudinal direction of the article in their stretched state to form a leg gather 222. The absorbent article also has a pair of first standing gathers 223 and a pair of second standing gathers 224, the base of each of which is located between the leg gather 222 and the side edge of the absorbent member 201. The first standing gathers 223 is on the side of the leg gather while the second standing gathers 224 on the side of the absorbent member.

The three pairs of gathers are preferably designed such that the outermost one may have a higher contractibility than the rest of three. That is, the contractive forces of the leg gather 220, the first standing gather 223, and the second standing gather 224 being taken as L1, L2, and L3, respectively, a preferred relation is L1 greater than both L2 and L3 (L1>L2, L3). It is more preferred that the contractive force gradually decreases from the outermost to the innermost, i.e., L1>L2>L3 for the following reasons.

Absorbent articles have been designed based on the concept that thickness reduction without causing leakage could be accomplished by providing gathers having high contractibility so as not to leave a gap between a wearer's body and the absorbent article. However, strongly contractible gathers tend to leave marks on the skin and, when combined with a thin and pliable absorbent member as provided in the invention, tend to curl up the absorbent article, making diapering difficult. Moreover, too strong contractive force of gathers creates downward force to cause displacement while worn. These inconveniences associated with conventional absorbent articles can be averted by providing a pair of leg gathers and two or more pairs of standing gathers with their contractibility satisfying the above-described relation.

The contractive force of a gather is measured as follows. A specimen cut out of a gathered part is tested on a tensilon tester ORIENTEC RTC-1150A to plot a hysteresis curve. The stress in the retracting curve is taken as a contractive force. The pulling and retracting speeds are 300 mm/min. The initial span length of the specimen is 100 mm, and the maximum elongation is 100 mm (stretched to double the initial length). The stress at 50 mm back from the maximum stretched length in the retracting curve of the hysteresis is read as a contractive force of the specimen. Measurement is made on five specimens per sample to obtain an average. When the maximum elongation does not reach 100 mm, the stress required for stretching the specimen to an elongation of 50 mm is taken as a contractive force of the specimen.

The contractibility of the gathers can be adjusted by, for example, changing at least one of the thickness of the elastic members, extensibility of the elastic members, and the number of the elastic members, and the like. The contractibility of the leg gather 222 is preferably exerted only in the crotch section of an absorbent article.

Figure 11:
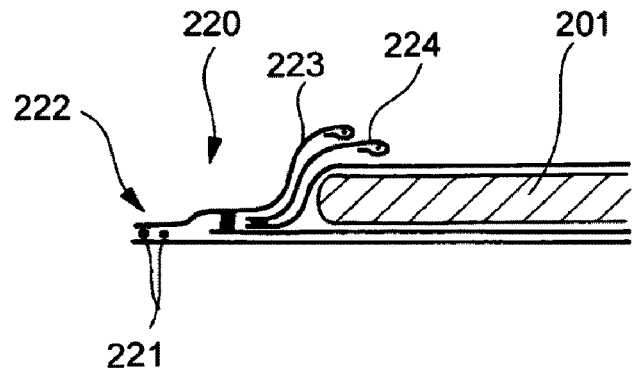
FIG. 11 is a schematic illustrating a transverse cross-sectional structure of another embodiment of the absorbent article according to the invention.
Figure 12:
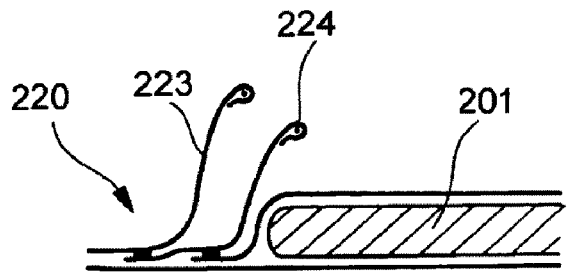
FIG. 12 is a schematic illustrating a transverse cross-sectional structure of still another embodiment of the absorbent article according to the invention (equivalent to FIG. 11).

While the absorbent article shown in FIG. 11 has a pair of leg gathers and two pairs of standing gathers, the absorbent article of the invention having any of the absorbent members of the aforementioned embodiments may have two or more pairs of standing gathers facing each other but no leg gathers. For instance, FIG. 12 fragmentarily illustrates an absorbent member having two pairs of opposing standing gathers; a first standing gather 223 and a second standing gather 224. In this embodiment, too, it is preferred that the contractibility of standing gathers decreases inboard for the same reason as described above.

Preferred embodiments of the first and second aspects of the present invention will then be described.

Figure 22:
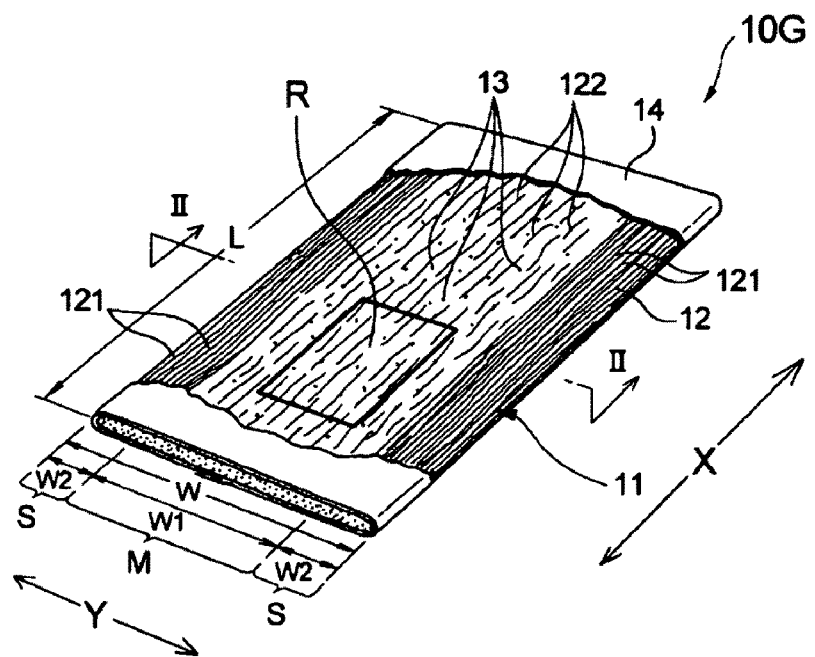
FIG. 22 is a perspective of an embodiment of the absorbent member according to the second or third aspect of the invention, with part cut away.

FIG. 22 illustrates an absorbent member 10G. The absorbent member 10G has an absorbent core 11 containing a fiber web 12. The fiber web 12 is made mainly of synthetic or semisynthetic fibers. The synthetic or semisynthetic fibers constituting the web are divided into four groups of fibers according to the ratio of their length to the total length L of the absorbent core 11. A first group of fibers have the ratio of less than 1/4. A second group of fibers have the ratio of 1/4 or more and less than 2/4. A third group of fibers have the ratio of 2/4 or more and less than 3/4. A fourth group of fibers have the ratio of 3/4 or more. The fiber web 12 contains at least three of the four groups of fibers. The cross-section of the absorbent member 10G taken along line II-II in FIG. 22 is equal to the cross-section of FIG. 2.

The absorbent member 10G will be described in greater detail. The absorbent member 10G includes an absorbent core 11 and a wrap sheet 14 wrapping the absorbent core 11. The absorbent core 11 has a fiber web 12 and an absorbent polymer 13 held in the fiber web 12. The fiber web 12 contains fibers of a variety of lengths from a sufficiently small length relative to the length L of the absorbent core 11 to almost the same length as L. The fiber web 12 is made mainly of synthetic or semisynthetic fibers.

To provide a measure to determine whether the fiber web 12 contains fibers of a variety of lengths, the constituent synthetic or semisynthetic fibers are divided into four groups of fibers according to the ratio of their length to the length of the absorbent core 11; a first group of fibers having the ratio of less than 1/4, a second group of fibers having the ratio of 1/4 or more and less than 2/4, a third group of fibers having the ratio of 2/4 or more and less than 3/4, and a fourth group of fibers having the ratio of 3/4 or more. According to the first aspect of the invention, whether the fiber web 12 contains at least three of the four groups of fibers is used as a criterion.

When the fiber web 12 constituting the absorbent core 11 contains at least three of the first to fourth groups of fibers, the absorbent member 10G exhibits excellent downward wicking properties and resistance to destruction or bunching by an outer force imposed during use. It is more preferred that the fiber web 12 contain all of the first to fourth groups of fibers.

Presence of fibers belonging to the first group secures downward wicking properties and resultant improvement of absorption rate. Presence of fibers classified into the second group not only serves for downward wicking but also imparts increased strength to the absorbent member to provide protection from destruction by an outer force imposed during use because fibers with certain lengths can intertwine with one another. Presence of fibers of the third group facilitates fluid spreading over a wider area in planar directions of the absorbent member to prevent local swell of the absorbent member thereby to prevent rewet and a resultant skin trouble as well as leakage due to a local flood. Presence of fibers classified as the fourth group provides advantages such as structural stabilization of the whole absorbent member (resistance to bunching) and improvement of transportability of the absorbent member in the production line.

Designing for Good Balance Between Downward Wicking and Planar Spread of Fluid:

Designing an absorbent member based on the following concept achieves a good balance between downward wicking and planar spread both related to absorption. Force related to fluid absorption in an absorbent member includes a capillary force of a fiber aggregate (inclusive of absorbency of a superabsorbent polymer, capillarity between particles of a superabsorbent polymer, and capillarity between a superabsorbent polymer particle and a fiber) and an outer force (e.g., the pressure of urination and a body weight). Absorption by an absorbent member is believed to be the result of entanglement of these forces. In other words, because a pressure of urination is applied during urination as a force related to absorption, vertical or downward wicking and rapid absorption can be achieved by using short fibers. After completion of urination, absorption is governed by the capillary force of the fiber aggregate so that the planar spreading force by long fibers brings about the above-described advantages, i.e., to prevent local swell of the absorbent member thereby to prevent rewet and a resultant skin trouble as well as leakage due to a local flood.

Whether the fiber web 12 contains at least three out of the four groups of fibers can be determined as follows. As illustrated in FIG. 22, a region R measuring, for example, 100 mm (in the width direction of the web) by 200 mm (in the length direction of the web) is marked on the fiber web 12 constituting the absorbent core 11. Thirty fibers are randomly drawn from the region R with tweezers, and the length of each of the fibers is measured. The fibers are classified by length into the first to fourth groups. When at least two fibers are classified into one group, the fiber web is regarded as containing the fibers of that group. When this applies to three or more groups of fibers, then the fiber web is regarded as "containing at least three out of the four groups of fibers". When this applies to each of the four groups of fibers, then the fiber web is regarded as "containing all of the first to fourth groups of fibers".

The dimension of the region R is subject to adjustment as appropriate to the size and shape of the absorbent member (or the size and shape of the fiber web in the case where the fiber web is disposed in a part of the absorbent member). The dimension in the longitudinal direction should be more than a half the total length of the absorbent member (or the fiber web). More specifically, Dimension of region $R$ in the longitudinal direction (mm)=[(total length of absorbent member)×1/2+10] (mm)

The dimension of the region R in the width direction is the maximum width that the absorbent member (or the fiber web) can measure over the whole length thereof. For instance, when the absorbent member (or the fiber web) has a constant width over its whole length, that width is the width of the region R. When the absorbent member (or the fiber web) has a width varied in the longitudinal direction (e.g., T-shaped or I-shaped), the width at the narrowest part is the width of the region R. The position of the region R (i.e., the position of sampling) in the absorbent member (or the fiber web) is such that the center of the region R is within a portion that is to be applied to the crotch of a wearer (the lowest body part) while the absorbent article is worn.

If there should be a missing part in the position of sampling of the absorbent member (or the fiber web), the region R is selected from a portion anterior to the missing part. In this case, the dimension of the region R is decided according to the above-described guidance except for the missing part.

The term "longitudinal direction" as used here with respect to the absorbent member (or the fiber web) refers to the direction in which the fibers classified as a group of the longest fibers are oriented, or, if the fibers are not oriented in a specific direction, this term means the longitudinal direction of the absorbent article.

In the case when the fiber length distribution varies from part to part in the absorbent member, that is, when the regions having the respective fibers of the first to fourth groups do not overlap at all or overlap in part with each other in the planar or thickness direction of the fiber web 12, the region R is sectioned into three blocks in its longitudinal direction and three blocks in its width direction to make 9 blocks in total, and three fibers are drawn from each block to determine the fiber length distribution of the whole absorbent member, from which whether the absorbent member contains at least three out of the first to fourth groups of fibers is judged.

It is preferred for the absorbent member to contain fibers classified as the first group from the standpoint of downward wicking properties. It is also preferred for the absorbent member to contain fibers classified as the fourth group in view of structural stabilization of the whole absorbent member (resistance to bunching) and improvement of transportability in the production line. From the comprehensive viewpoint, it is preferred that the absorbent member contains all of the first to fourth groups of fibers.

In the case where three or four of the first to fourth groups of fibers are present in a mixed state in the fiber web 12, the proportions of the first, second, third, and fourth groups of fibers in the fibers constituting the fiber web 12 are preferably 0% to 80%, 0% to 80%, 0% to 80%, and 0% to 50%, respectively, more preferably 10% to 60%, 10% to 60%, 10% to 60%, and 5% to 30%, respectively. This preference does not apply, however, to the case where three or more of the four groups of fibers are unevenly distributed in the fiber web 12.

The size of the absorbent core 11 is decided as appropriate to the intended use of the absorbent member 4 and the like. For example but not for limitation, the whole length L of the absorbent core is preferably 100 to 600 mm, more preferably 150 to 500 mm, for use in diapers for children; preferably 250 to 900 mm, more preferably 300 to 800 mm, in the case of diapers for adults; and preferably 50 to 500 mm, more preferably 70 to 450 mm, for use in sanitary napkins or incontinence pads.

The fiber web 12 used in the present embodiment is prepared from a crimped continuous fiber web 12A as will be described with reference to the production method. Accordingly, the fibers drawn from the fiber web include crimped fibers. The length of such a crimped fiber is measured as the fiber has a crimp. That is, the fiber length of a crimped fiber is the "natural length" of the fiber as referred to in the measurement of percentage of crimp hereinafter described.

The fiber web 12 preferably contains crimped fibers as in the present embodiment. The percent of crimp (JIS L0208) of the crimped fibers is preferably 10% to 90%, more preferably 10% to 60%, even more preferably 10% to 50%. The absorbent member 10G of which the fiber web 12 contains crimped fibers is flexibly deformable as a whole and, as assembled into an absorbent article, exhibits improved fit against a wearer's body or improved deformability to form a concave shape to enhance leak prevention. Furthermore, the absorbent polymer can be held more stably by the crimped staple fibers in the web 12 and is thereby prevented from moving in or falling off the web.

It is preferred that the above-recited preferred range of crimp percentage be satisfied by at least the first group of fibers, more preferably by the first group of fibers and the group of longest fibers present in the absorbent member, even more preferably by all the groups of fibers present in the absorbent member.

The crimp of the fibers may be either two-dimensional or three-dimensional. The percentage of crimp (or crimp percentage) of the fibers is defined to be a percentage of a difference between the length A of a crimped fiber in its straightened state and the natural length B of the crimped fiber to the length A, being calculated from equation:

$$\text{Percentage of crimp (\%)} = ((A-B)/A) \times 100$$

The natural length of a crimped fiber is the length of the straight line connecting the two ends of a fiber in its natural state. The term "natural state" means a state of a fiber hanging under its own weight with its one end fixed to a horizontal plate. The term "straightened state" means a state of a fiber stretched out until no crimp remains under a minimum load. The number of crimps of the crimped fibers having the recited percentage of crimp is preferably 2 to 25, more preferably 4 to 20, even more preferably 10 to 20, per centimeter.

Describing the absorbent member 10G of the present embodiment in more detail, the absorbent member 10G is an oblong rectangle in a plan view and is designed to be assembled into an absorbent article with its longitudinal direction coinciding with the front-to-rear direction of a wearer. In the absorbent member 10G of the present embodiment, the fibers making up the fiber web 12 are oriented generally in a specific planar direction (direction X in FIG. 22).

Where the fibers of the fiber web 12 (particularly the fibers of the longest fiber group present in the absorbent member) are oriented generally in a specific planar direction (direction X in FIG. 22) as in the present embodiment, the whole length L of the absorbent core 11 is the length L in the orientation direction (direction X). Where the fibers of the fiber web 12 are not oriented in a specific direction, the whole length of the absorbent core 11 is the length in the direction coincident with the front-to-rear direction of a wearer during use. In the case where the fibers of the fiber web 12 in the absorbent member of FIG. 22 are oriented in direction Y perpendicular to direction X, the dimension in the width direction of the absorbent core 11 (substantially equal to the width W of the absorbent member) is the whole length of the absorbent core 11.

All the fibers classified into the first to fourth groups of fibers according to the present embodiment are synthetic or semisynthetic fibers.

Examples of the synthetic fibers include polyethylene, polypropylene, polyethylene terephthalate, polybutylene terephthalate, polytetramethylene terephthalate, nylon, and acrylic fibers. Examples of the semisynthetic fibers include rayon, cellulose acetate (cellulose triacetate and cellulose diacetate), Lyocell, Tencel, and cuprammonium. The synthetic or semisynthetic fibers enumerated above can be used either individually or as a combination of two or more thereof. The phrase "synthetic or semisynthetic" as used herein is intended to include a combination of synthetic fibers and semisynthetic fibers.

As compared with absorbent members made mainly of conventionally commonly employed pulp fiber, using the fiber web made mainly of synthetic or semisynthetic fibers enables controlling a fiber length, fiber thickness or hydrophilicity over broad ranges. This makes it feasible to design an absorbent member so as to reduce fluid remaining and rewet. The absorbent member having the fiber web made mainly of synthetic or semisynthetic fibers have advantages, including resistance to collapse when wetted, reduced reduction in absorption rate with repetition of absorption, high compressive strength when wetted that reduces rewet, capability of controlling the fiber length and thickness that guarantees resistance to breakage even with a reduced thickness of the absorbent member, and ease of bonding to other members making up an absorbent article.

While the fiber web 12 in the present embodiment has a synthetic or semisynthetic fiber content of 100%, the fiber web 12 may contain fibers other than the synthetic or semisynthetic fibers. Nevertheless, the content of the synthetic or semisynthetic fibers in the total constituent fiber of the fiber web 12 is preferably 80% to 100% by weight, more preferably 90% to 100% by weight. Examples of fibers other than the synthetic or semisynthetic fibers include pulp fiber and cotton fiber.

The first to fourth groups of fibers constituting the fiber web 12 are preferably hydrophilic fibers. Hydrophilic fibers include those essentially having hydrophilic properties and those essentially having no hydrophilic properties but having been made hydrophilic as a result of hydrophilization treatment. Fibers essentially having hydrophilic properties are preferred. Cellulose acetate fibers or rayon fibers are more preferred. In particular, cellulose acetate fibers are preferred; for a cellulose acetate fiber web keeps bulkiness even when wetted. Cellulose triacetate and/or cellulose diacetate are preferably used as cellulose acetate.

In the absorbent member 10G of the present embodiment, the absorbent polymer 13 is unevenly distributed in a planar direction of the absorbent member 10G. Specifically, as shown in FIGS. 22 and 2, the absorbent polymer 13 is localized in the part of the web 12 that is located in a plan view in a region M of the absorbent member 10G. The region M is a laterally middle portion of the absorbent member 10G with a prescribed width (hereinafter also referred to as a middle region M). The absorbent polymer 13 is distributed substantially evenly in the part of the web located in the middle region M of the absorbent member and is substantially absent in the parts located in side regions S outboard of the middle region M.

The fiber web 12 has fibers 122 classified as the first group of fibers distributed substantially evenly in the middle region M of the absorbent member 10G. Fibers classified as the second to fourth groups of fibers, while now shown, are also distributed in substantially the same region where the fibers 122 are distributed. That is, fibers belonging to the first to fourth groups of fibers are present in a mixed state in the middle region M.

The mixed presence of the fibers belonging to the four groups of fibers assures that the absorbent member exhibits downward wicking properties with associated improvement in absorption rate, improved strength of the absorbent member, and improved liquid spreading properties. A good balance between downward wicking properties and spreading properties can be achieved through the above-described "Designing for Good Balance between Downward Wicking and Planar Spread of Fluid".

Almost all the fibers making the part of the fiber web 12 corresponding to the side regions S of the absorbent member 10G are fibers 121 extending over the whole length of the absorbent core 11 and classified as the fourth group of fibers.

The embodiment in which the fiber web 12 contains at least three out of the first to fourth groups of fibers may be exemplified by an embodiment in which the fibers classified into the first to fourth groups are distributed in different regions that do not overlap at all in either the planar direction or the thickness direction of the web 12. However, it is preferred that the regions having respective fibers of three or more groups overlap at least partially with each other in the planar or thickness direction of the web 12. While in the present embodiment all the fibers of the first to fourth groups are distributed in the middle region M, it is possible to distribute only the fibers of the first to third groups in a mixed state in the middle region M. The width W1 of the region where the first to third groups of fibers or all the first to fourth groups of fibers exist (the middle region M in the case of the present embodiment) is preferably 20% to 100%, more preferably 50% to 90%, of the total width W of the absorbent member 10G.

Examples of the absorbent polymer 13 include those conventionally used in absorbent members of disposable diapers, sanitary napkins, and the like, such as sodium polyacrylate, acrylic acid-vinyl alcohol copolymers, crosslinked sodium polyacrylate, starch-acrylic acid graft polymers, isobutylene-maleic anhydride copolymers and saponification products thereof, potassium polyacrylate, and cesium polyacrylate.

As previously stated, in view of the amount of the absorbent polymer to be used and prevention of reduction in gel feel after fluid acquisition, it is preferred that the absorbent polymer 13 have a physiological saline absorption of 30 g/g or more, more preferably 30 to 50 g/g, measured by a centrifugal dewatering method.

As previously stated, in order to prevent gel blocking and the resultant reduction in absorbency from occurring and to prevent leakage of a fluid having passed through the polymer particles without being absorbed, it is also preferred for the absorbent polymer to have a liquid transit time of 20 seconds or less, more preferably 2 to 15 seconds, even more preferably 4 to 10 seconds.

As previously mentioned, it is also preferred for the absorbent polymer to have high liquid permeability under load.

The absorbent member 10G according to the present embodiment provides the same effects as by the absorbent member 10 described above by way of FIG. 3.

Under some conditions of use, a pressure is imposed to a part or parts of the absorbent member to immobilize the fibers in the part or parts. If the fibers are long, both ends thereof would be immobilized, which can result in tightening of fibers (fixing of the structure) when the absorbent member (specifically, the absorbent polymer) swells, and eventually interfere with swell.

In order to prevent fibers clinging to the superabsorbent polymer particles from tightening and hindering swell of the superabsorbent polymer under pressure imposed during use of the absorbent article, it is preferred for the fiber web 12 to contain fibers-classified as the first or second group (fibers having short lengths).

Bunching or roping of an absorbent member interferes with manifestation of stable performance and causes discomfort during use. Bunching occurs when an absorbent member fails to relax a stress imposed thereto. If the fiber web 12 is totally made up of continuous fibers, a stress imposed to part of the absorbent member would be transmitted via the fibers and exerted all over the absorbent member to cause bunching of the whole absorbent member. Where the fiber web 12 contains the first, second, and third groups of fibers, in contrast, a tensile or compressive force, if applied to part of the absorbent member 10G during use, will not be exerted all over the absorbent member. The absorbent member is thus prevented from bunching.

The wrap sheet 14 is preferably a water permeable sheet material such as tissue paper or a water permeable nonwoven fabric.

A preferred method of preparing the absorbent member 10G (an embodiment of the method of producing the absorbent member according to the present invention) will be described by way of FIG. 23. The method of the present embodiment for producing the absorbent member 10G is implemented by using apparatus illustrated in FIG. 23 in the same manner as in the previously described method of producing the absorbent member 10. The description about the apparatus illustrated in FIG. 4 and the method of producing the absorbent member 10 using the apparatus applies to the apparatus of FIG. 23 and the method of producing the absorbent member 10G using the apparatus unless otherwise specified.

In the present embodiment, absorbent polymer is spread on a continuous fiber web 12A that is obtained by opening a tow 12a. That is, particles of an absorbent polymer 13 are used as "particles".

It is preferred to use absorbent polymer particles at least part of which are lumpy. The lumpy absorbent polymer particles are obtained by casting a water-containing gel of an absorbent polymer synthesized by solution polymerization into a sheet, drying the cast sheet, and grinding the dried sheet, or the lumpy absorbent polymer particles are agglomerates of irregular particles formed by reverse phase suspension polymerization using a selected surface active agent under a controlled stirring force. On the other hand, non-lumpy particles include spherical particles, agglomerates of spherical particles, fibrous particles, and flaky particles.

The lumpy absorbent polymer particles preferably have an average particle size of 150 to 600 µm, more preferably 200 to 500 µm. This preference of particle size applies to lumpy particles other than the absorbent polymer particles.

Examples of the particles that can be used include not only absorbent polymer but organic or inorganic particles useful as a deodorant or an antimicrobial agent such as cellulose powder, activated carbon, silica, alumina, and various minerals (e.g., zeolite, sepiolite, bentonite, cancrinite, hectorite, and smectite). The inorganic particles may have part of their metal sites replaced. The particles may be used in the form of agglomerates thereof or as a composite with a carrier. These particulate substances may be used either individually or in combination of two or more thereof. Agglomerates or composites with a carrier preferably have an average particle size of 150 to 600 µm, more preferably 200 to 500 µm.

In the present embodiment, the absorbent polymer 13 is spread in a continuous manner in the machine direction of the web 12A on only a region with a prescribed width in the laterally middle of the web 12A.

The absorbent polymer 13 preferably has a bulk density of 0.5 to 0.8 g/cm$^3$, more preferably 0.55 to 0.7 g/cm$^3$, to facilitate creating fibers of various lengths that can be classified into the first to third groups of fibers by cutting the continuous fibers as will be described later.

In order to facilitate creating fibers of various lengths that can be classified into the first to third groups of fibers by cutting the continuous fibers as will be described later, it is preferred that the particle size distribution of absorbent polymer 13 be such that the average particle size ranges from 250 to 450 µm and that the proportion of particles of 425 µm or greater is 5% to 40%. It is more preferred that the proportion of particles of 425 µm or greater be 10% to 35% to achieve efficient fiber cutting thereby to reduce a rough feel of the absorbent member. Because larger particles are less close-packed, the fibers are cut more efficiently when wedged between such superabsorbent polymer particles or between such a superabsorbent polymer particle and a roller.

The superabsorbent polymer 13 may be spread in a continuous manner but with a basis weight variation in the longitudinal direction or in a discontinuous manner in the longitudinal direction. In order to achieve efficient cutting of continuous fibers, the amount of the superabsorbent polymer to be spread is at least equivalent to, preferably twice or more times, more preferably three or more times, the amount of the continuous fibers. Accordingly, in continuously spreading with a basis weight variation, the ratio of the superabsorbent polymer to the continuous fibers is varied in the machine direction between regions A where the ratio is less than 1 and regions B where the ratio is 1 or greater, preferably 2 or greater, even more preferably 3 or greater. The higher the basis weight of the superabsorbent polymer, the higher the probability of fiber cutting and the shorter the resulting cut fibers. The proportions and distributions of the first to third groups of fibers can be controlled by controlling the distribution of the regions A and B.

As previously described, presence of short fibers such as the first group of fibers secures downward wicking properties and resultant improvement of absorption rate but can concentrate a fluid to increase rewet. This problem can be solved by distributing an increased amount of a superabsorbent polymer in the region having the first group of fibers. On the other hand, since a region having longer fibers, for example, the third group of fibers serves for the function of spreading a fluid in a wider area in the planar directions of the absorbent member, the amount of the superabsorbent polymer to be spread in the region is decreased to enhance the fluid spreading properties making use of the fiber orientation.

Because non-lumpy superabsorbent polymer particles are less capable of cutting fibers than lumpy superabsorbent polymer particles, the fiber length distribution can also be controlled by using a mixture of lumpy superabsorbent polymer particles and non-lumpy superabsorbent polymer particles or spreading these different kinds of particles in different regions.

Cutting of fibers can be controlled by adjusting the ratio of the superabsorbent polymer to the fiber. Therefore, the fiber length distribution can be controlled by changing the amount of the fiber with a certain amount of the superabsorbent polymer. That is, the fiber web is designed to have a region having the fibers in an amount less than the superabsorbent polymer (a region where the fibers are easily cut) and a region having the fibers in an amount equal to or greater than that of the superabsorbent polymer (a region where the fibers are hardly cut) to provide a region having short fibers and a region having part of the fibers non-cut.

Methods of providing a region having a relatively large amount of short fibers include using a roller the surface of which has a reduced hardness (for example, using rubber having a decreased JIS hardness, measured with, e.g., type A durometer, Ascar A type specified in JIS K6253), reducing the roller diameter to increase the linear pressure, using a combination of these rollers, and passing the web through rollers repeatedly. Reducing the roller hardness helps the fibers or superabsorbent polymer particles to bite into the roller surface to ensure cutting.

In the present embodiment, the wrap sheet 14 has a width enough to cover both the upper and lower sides of the web 12A. After the absorbent polymer 13 is fed on the web 12A (2 portions), both side portions 14a of the wrap sheet 14 are folded over to cover the upper side of the web 12A (2 portions) by means of a folding mechanism 7 as illustrated in FIG. 23. The wrap sheet 14 can be of any material conventionally employed to wrap an absorbent core in.

In the present embodiment, too, the continuous-form absorbent member 100 is subjected to compression by pressure application in the aforementioned continuous fiber cutting mechanism 8 thereby to cut the continuous fibers. The compression and the resultant cutting of continuous fibers can be carried out by passing the continuous-form absorbent member 100 through a pair of rollers 80 and 81 to press, in the thickness direction, a part or the whole of the region of the web 12A having the absorbent polymer 13 spread thereon.

The continuous fiber cutting takes place within an area in which the absorbent polymer 13 has been spread and which is pressed between the peripheral surface 80M of one of the rollers (the roller 80) made of an elastic material and the peripheral surface of the other roller (the roller 81) made of a hard material. As illustrated in FIG. 5, the continuous fibers 121 are pressed onto the lumpy absorbent polymer particles 13 and cut thereby.

The continuous-form absorbent member 100 having the continuous fibers in part of the web 12A cut is then cut by the continuous-form absorbent member cutting mechanism 5 into individual absorbent members 10G having a desired length appropriate to the type and size of an absorbent article in which the resulting absorbent member is to be assembled.

According to the method of the present embodiment, the absorbent member 10G having the aforementioned structure can be produced efficiently and continuously.

As described, the production method according to the present embodiment includes the steps of spreading lumpy particles of an absorbent polymer on a web of continuous fibers and pressing the web in its thickness direction to cut the continuous fibers of the web into various lengths.

The terminology "a continuous fiber web" as used herein means a web of fibers having a fiber length equal to or longer than the whole length of the absorbent core 11 as measured by the mean fiber length measurement method (method C) specified in JIS L1015. The continuous fibers used in the present invention are generally termed "continuous filaments". A bundle of continuous filaments is generally termed "a tow". Accordingly, the terminology "continuous fiber" as used herein shall include a continuous filament.

Seeing that the web of continuous fibers is to be compressively pressed in the presence of lumpy particles (such as lumpy absorbent polymer particles) to cut the continuous fibers as in the production method of the present embodiment, it is preferred that the continuous fibers have a fiber strength of not more than 3 g/d, more preferably 0.5 to 2.5 g/d.

The fiber strength is measured as follows.
Method of Measuring Fiber Strength:

The method of tensile strength measurement in "Test methods for man-made staple fibers" specified in JIS L1015 was followed. That is, a fiber is attached to a sheet of copier paper at both ends thereof with an 18 mm wide adhesive tape (Scotch Tape (trade name) from Nichiban Co., Ltd.) so as to have a spatial length (the length except the fixed parts at both ends) of 20 mm (or 10 mm in case of a short fiber). The specimen thus prepared is set between chucks of a Tensilon tensile tester (RTC-1150A, from Orientech Co., Ltd.), and, after the paper is cut along near each of the tape-fixed ends, pulled at a rate of 300 mm/min. A load cell having a full scale of 5 kg is used, and the measuring range is changed appropriately. The measurement is made at 10 points to obtain an average. A measurement value deviating 20% or more from the average is discarded, and an additional measurement is carried out.

The continuous fibers preferably have a fineness of 1.0 to 10 dtex, more preferably 1.5 to 8 dtex.

The first to fourth groups of fibers obtained by the production method of the present embodiment are arranged such that the two longitudinal ends (cut ends) of individual cut fibers are located at random positions in the longitudinal direction of the absorbent member.

Although the first to fourth groups of fibers obtained by the production method of the present embodiment are not bonded to one another, they may be bonded to one another if desired. Bonding of fibers can be achieved either before or after the step of cutting the continuous fibers by, for example, thermally bonding the fibers at their intersections (e.g., by through-air bonding), heat embossing, or spraying or applying a binder or a plasticizer. An adhesive may be used to bond the fibers.

Another method of producing the absorbent member according to the first and/or the second aspect of the invention will then be described with reference to FIGS. 24 and 25.

Figure 23:
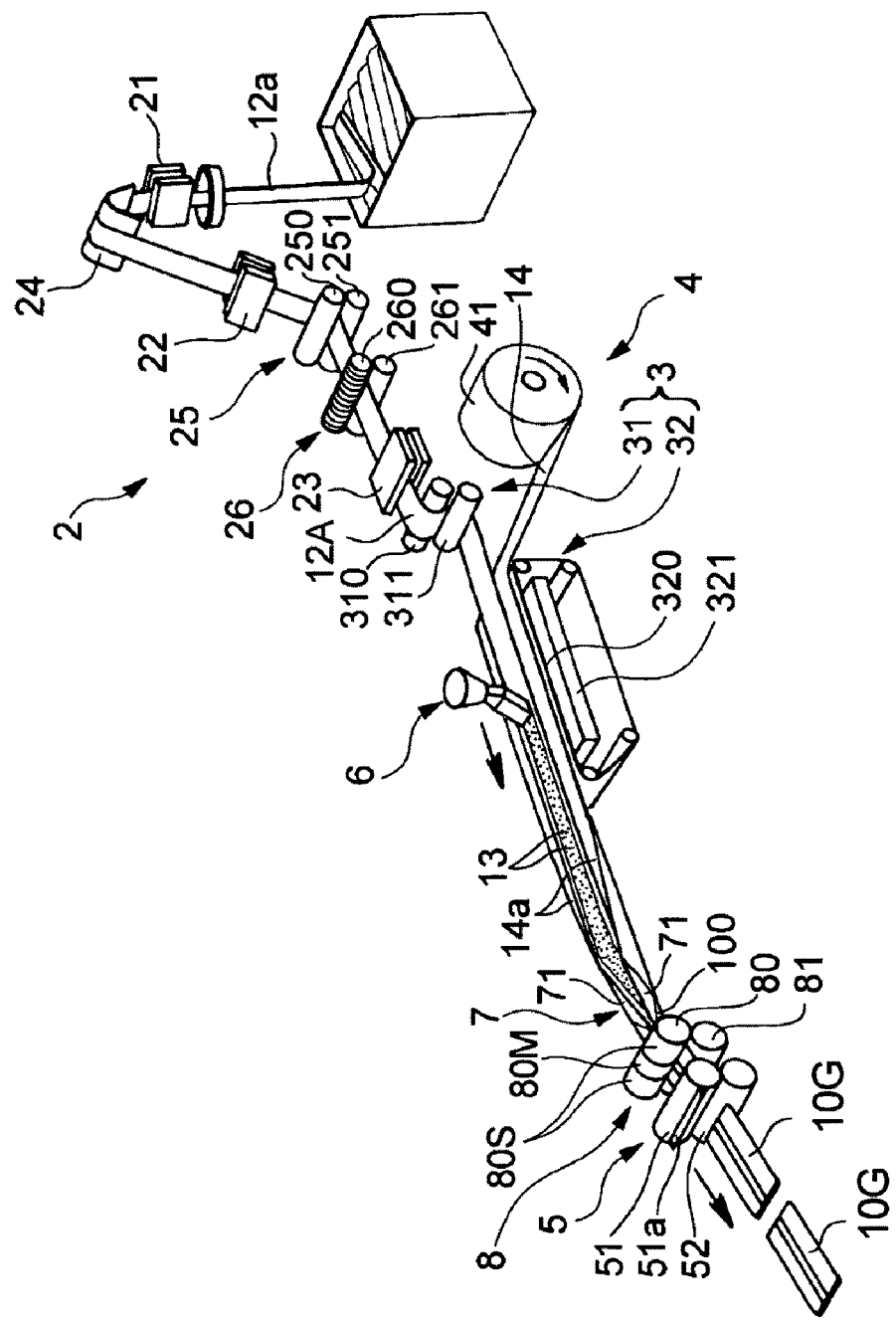
FIG. 23 is a perspective illustrating one embodiment of the method of producing the absorbent member according to the invention with the apparatus for carrying out it.
Figure 24:
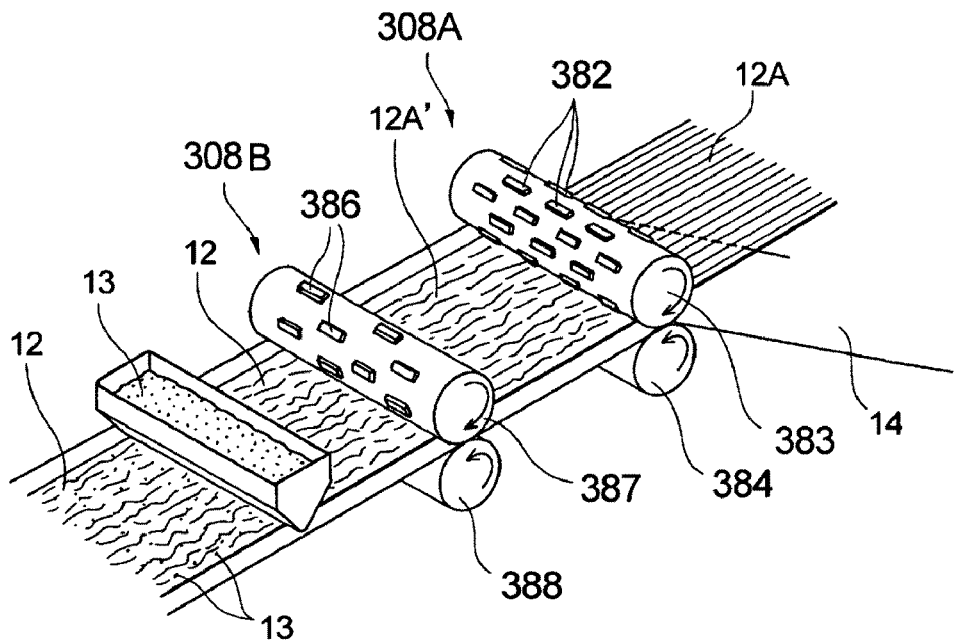
FIG. 24 is a perspective illustrating another embodiment of the method of producing the absorbent member according to the invention.

The production method illustrated in FIG. 24 includes the steps of superposing a continuous fiber web 12A obtained in the same manner as in the embodiment shown in FIG. 23 on a wrap sheet 14 and cutting the continuous fibers successively in a first cutting mechanism 308A and a second cutting mechanism 308B.

The first cutting mechanism 308A includes a cutter roller 383 having a large number of blades 382 on its peripheral surface and an anvil roller 384 that receives the blades 382 of the cutter roller 383 on its peripheral surface. The first cutting mechanism provides the web 12A being introduced into the nip of these rollers with a large number of first cuts 385 (first cutting step).

The second cutting mechanism 308B includes a cutter roller 387 having a large number of blades 386 on its peripheral surface and an anvil roller 388 that receives the blades of the cutter roller 387 on its peripheral surface. The second cutting mechanism provides the web 12A' being introduced into the nip of these rollers with a large number of second cuts 389 (second cutting step).

In the present embodiment, the pattern of the first cuts 385 made in the first cutting step and the pattern of the second cuts 389 made in the second cutting step are different. More specifically, the pattern of the first cuts 385 are composed of lines 385L of cuts regularly spaced in the running direction of the web 12A, each line 385L being composed of a plurality of cuts arranged in series in the width direction of the web 12A. The positions of the cuts of one of the lines 385L in the width direction of the web 12A are out of alignment with those of the cuts of adjacent lines 385L by half the pitch of the cuts in every line of cuts. The pattern of the second cuts 389 is composed of lines 389L of a plurality of cuts regularly spaced in the running direction of the web 12A, each line 389L being oblique to the longitudinal direction of the web 12A. The positions of the cuts of one of the lines 389L in the width direction of the web 12A are out of alignment with those of the cuts of adjacent lines 389L by a distance less than half the pitch of the first cuts in every line 385L.

By successively cutting the continuous fibers of the continuous fiber web through the first and second cutting steps in different patterns in that way, the continuous fibers are cut into a variety of lengths, and the fiber web 12 containing the first to third groups of fibers can easily be obtained.

After lumpy or non-lumpy particles of the absorbent polymer 13 are spread on the resulting fiber web 12, the web is cut to the length of an absorbent article to provide an absorbent member (not shown) of an embodiment of the present invention. In the present embodiment a wrap sheet 14 is superposed on one side of the continuous fiber web before cutting the continuous fibers, and another wrap sheet (not shown) is superposed on the other side after spreading the absorbent polymer 13. The fiber web 12 thus covered by the two wrap sheets is then cut to the length of an absorbent article.

According to the above-described embodiment of the method of producing the absorbent member 10G, it is easy to control the fiber lengths and the fiber length distribution.

Still another embodiment of the method of producing the absorbent body according to the invention will be described with reference to FIGS. 26 and 27.

Figure 26:
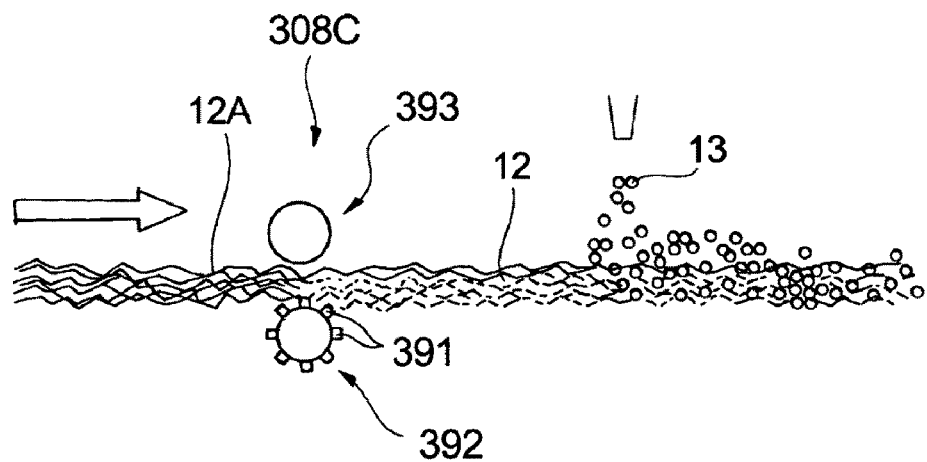
FIG. 26 schematically illustrates still another embodiment of the method of producing the absorbent member according to the invention.

The production method illustrated in FIG. 26 includes the steps of superposing a wrap sheet (not shown) on one side of a continuous fiber web 12A obtained in the same manner as in the embodiment shown in FIG. 23 and cutting the continuous fibers by a cutting mechanism 308C.

The cutting mechanism 308C is composed of a pressing roller 392 having a large number of projections 391 on its peripheral surface and a backup roll 393 having a smooth peripheral surface disposed in an opposite relation with the pressing roller. The cutting mechanism 308C cuts the continuous fibers of the web 12A being introduced between the two rollers by pressing the continuous fibers between the projections 391 and the peripheral surface of the backup roller 393.

Figure 27:
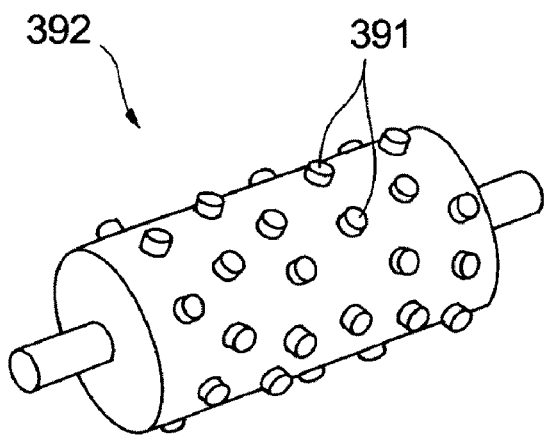
FIG. 27 is an enlarged perspective of an example of the pressing roller that can be used in the method of FIG. 26.

As illustrated in FIG. 27, the projections 391 of the pressing roller 392 are randomly arranged at various distances from one another. The fiber web 12 containing the first to third groups of fibers can easily be obtained by cutting the continuous fibers into various lengths using such randomly arranged cutting projections.

After lumpy or non-lumpy particles of the absorbent polymer 13 are spread on the resulting fiber web 12, the web is cut to the length of an absorbent article to provide an absorbent member (not shown) of an embodiment of the present invention. In the present embodiment a wrap sheet 14 is superposed on one side of the continuous fiber web before cutting the continuous fibers, and another wrap sheet (not shown) is superposed on the other side after spreading the absorbent polymer 13. The fiber web 12 thus covered by the two wrap sheets is then cut to the length of an absorbent article.

According to the above-described embodiment of the method of producing an absorbent member, it is possible to independently control the superabsorbent polymer distribution and the fiber distribution.

The difference between the absorbent member according to the second aspect of the present invention and that of the first aspect consists in the criteria of classifying the constituent synthetic or semisynthetic fibers into the first to fourth groups. In the second aspect of the invention, fibers sampled from a fiber web (synthetic or semisynthetic fibers) in the same manner as in the first aspect of the invention are classified into first to fourth groups; a first group having a length shorter than 25 mm, a second group having a length of 25 mm or longer and shorter than 50 mm, a third group having a length of 50 mm or longer and shorter than 100 mm, and a fourth group having a length of 100 mm or longer. The absorbent member according to the second aspect of the invention contains at least three of the four groups of fibers.

The embodiments of the absorbent member according to the second aspect of the invention and the embodiments of the method of producing the same are exemplified by those described with respect to the first aspect of the invention, except for replacing the making of the first to fourth groups of fibers as classified by the criteria adopted in the first aspect by the making of the first to fourth groups of fibers as classified by the criteria adopted in the second aspect. That is, the second aspect of the invention is equal to the first aspect, except for the difference in the criteria of classifying the constituent synthetic or semisynthetic fibers into four groups. Accordingly, the description about the first aspect of the invention, inclusive of the preferred structure and the like, applies to the second one except for the above-described difference.

The absorbent members of the first and second aspects of the invention and methods of producing them are not limited to the foregoing embodiments, and various changes and modifications can be added to the foregoing embodiments as exemplified as follows.

While the absorbent member 10G described contains the first to fourth groups of fibers in a mixed state in the fiber web 12 in the middle region M of the absorbent member 10G, the first to fourth groups of fibers may be present in a mixed state over the whole width of the fiber web 12 in the width direction of the absorbent member 10G.

The fiber web 12 may be formed of a plurality of subwebs each containing at least one of the first to fourth groups of fibers. In this case, the fiber web 12 has a fiber length distribution in its thickness direction.

The fiber web 12 may be laminated with a dry-laid web containing fluff pulp. The fiber web 12 and the fluff pulp-containing dry-laid web may be separately wrapped in respective wrap sheets and then stacked on each other, or the fiber web 12 and the fluff pulp-containing dry-laid web may be stacked on each other and wrapped in a wrap sheet to make a unitary absorbent member. Such an absorbent member is preferably assembled into an absorbent article with the fiber web 12 being adapted to face the skin of a wearer.

Examples of the fluff pulp-containing dry-laid web include a dry-laid web made solely of fluff pulp, a mixed dry-laid web made of fluff pulp and absorbent polymer particles, a mixed dry-laid, thermally united web made from fluff pulp and thermally fusible synthetic fibers, a mixed dry-laid, thermally united web made from fluff pulp, absorbent polymer particles, and thermally fusible synthetic fibers, an embossed, dry-laid web of fluff pulp, an embossed, mixed dry-laid web of fluff pulp and absorbent polymer particles, and a mixed dry-laid web made of fluff pulp having been sprayed with water and absorbent polymer particles. The fluff pulp content of the fluff pulp-containing dry-laid web may be 50% to 100% by mass.

Figure 25:
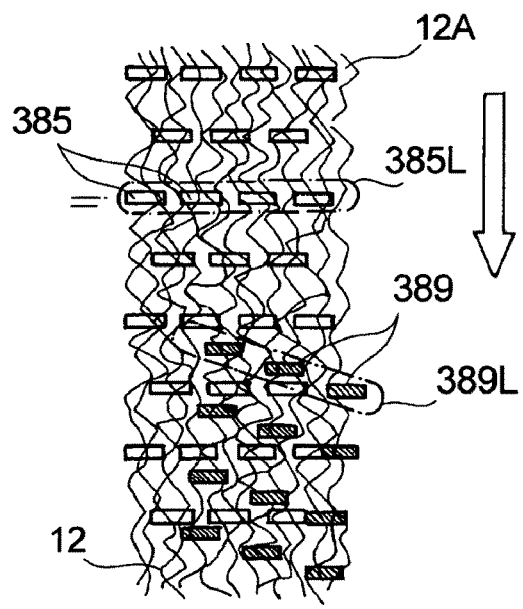
FIG. 25 illustrates the patterns of first and second cuts formed in the embodiment illustrated in FIG. 24.

The pressing roller 392 in the embodiment illustrated in FIGS. 26 and 27 may be replaced with the same cutter roller as used in the embodiment shown in FIGS. 24 and 25, except for replacing the regular arrangement of the blades of the cutter roller with the random arrangement of the projections of the pressing roller 392.

The sets of the cutter roller and the anvil roller in the embodiment illustrated in FIGS. 24 and 25 may be replaced with sets of a pressing roller and a backup roller like the set used in the embodiment illustrated in FIGS. 26 and 27, provided that the pattern of the cuts formed are different between the first and second cutting steps.

Examples of the absorbent article in which the absorbent member of the invention is assembled include disposable diapers, sanitary napkins, panty liners, and incontinence pads. Usually, the absorbent article has a liquid permeable topsheet, a liquid impermeable or water repellent backsheet, and an absorbent member interposed between these sheets.

The third aspect of the present invention will now be illustrated based on its preferred embodiments with reference to the drawing.

Figure 30:
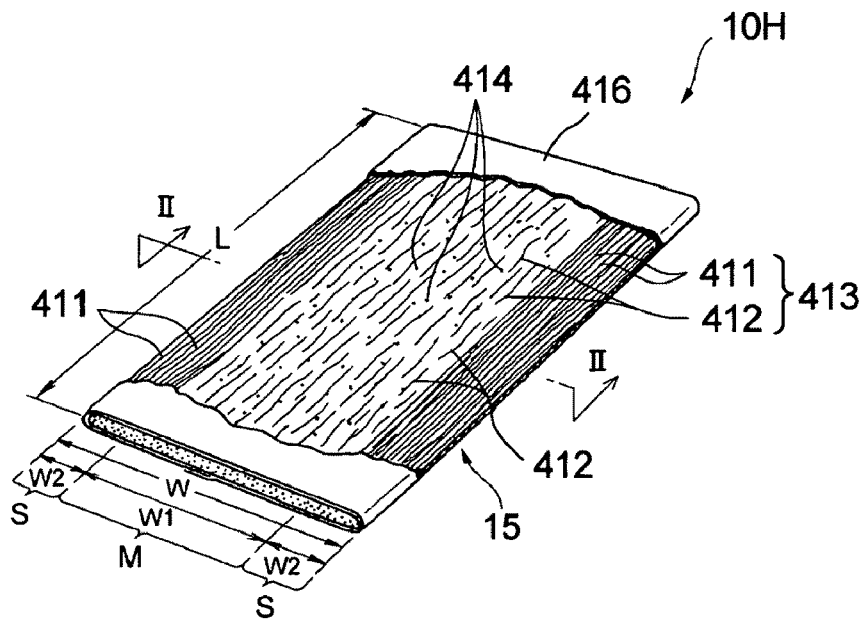
FIG. 30 is a perspective of one embodiment of the absorbent member according to the invention, with part cut away.
Figure 31:
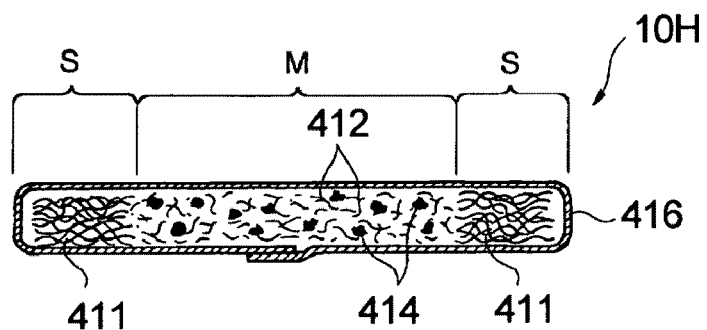
FIG. 31 is a cross-section of the absorbent member of FIG. 30, taken along line II-II.

FIG. 30 is a perspective of an embodiment of the absorbent member according to the invention, with part cut away. FIG. 31 is a cross-section taken along line II-II of FIG. 30. As shown in FIGS. 30 and 31, the absorbent member 10H of FIG. 30 includes an absorbent core 415 and a wrap sheet 416 wrapping the absorbent core 415; the absorbent core 415 is composed of a web 413 and particles 414 held in the web 413; and the web 413 contains continuous fibers 411 and staple fibers 412. The core 415 in the absorbent member 10H of the present embodiment has a single-ply structure. The absorbent member 10H is an elongated rectangle in a plan view and, when assembled into an absorbent article, has its longitudinal direction coinciding with the front-to-rear direction of a wearer while worn.

In the present embodiment, the particles 414 contained in the web 413 are particles of an absorbent polymer. The absorbent polymer particles 414 are unevenly distributed in a planar direction of the absorbent member 10H. Specifically, as shown in FIGS. 30 and 31, it is localized in a region M of the absorbent member 10H. The region M has a prescribed width and is located in the laterally middle portion of the absorbent member 10H in a plan view (hereinafter also referred to as a middle region M). The absorbent polymer 414 is distributed substantially evenly in the middle region M and is substantially absent in side regions S outboard of the middle region M.

In the part where the absorbent polymer 414 is distributed in a planar direction of the web 413, i.e., in the part located in the middle region M are there a great number of the staple fibers 412. On the other hand, there are the continuous fibers 411 in the parts located in the side regions S. The continuous fibers 411 and the staple fibers 412 are thus localized in different parts of the absorbent body 10H in a plan view. This does not mean to exclude the possibility that a small amount of the continuous fibers 411 exist in the middle region M or a small amount of the staple fibers 412 exist in the side regions S.

The staple fibers 412 present in the middle region M are oriented in one planar direction of the absorbent member 10H. The continuous fibers 411 present in the side regions S are oriented in one planar direction of the absorbent member 10H similarly to the staple fibers 412. The continuous fibers 411 and the staple fibers 412 have the same orientation direction. Specifically, the continuous fibers 411 and the staple fibers 412 are both oriented in the longitudinal direction of the absorbent body 10H.

Figure 32:
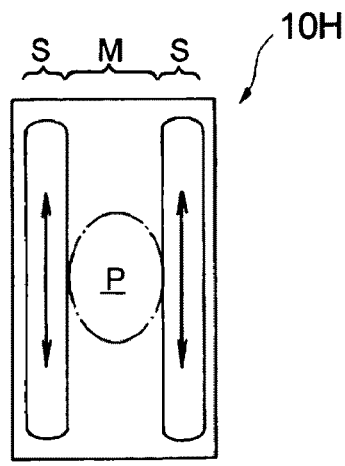
FIG. 32 is a schematic plan illustrative of the effects of the absorbent member shown in FIG. 30.

The absorbent member 10H is assembled into an absorbent article such as a disposable diaper or a sanitary napkin with its middle region M (where the continuous fibers have been cut into staple fibers) located in the target zone P that is adapted to face a point of body fluid discharge of a wearer as illustrated in FIG. 32. When the fibers existing in the middle region M of the absorbent member 10H are oriented in the longitudinal direction of the absorbent member 10H, a body fluid discharged in the middle region M is smoothly drawn into the inside of the absorbent member 10H within a small planar area. The fluid acquired into the absorbent member 10H is absorbed by the absorbent polymer 414 localized in that region and thus stably retained in the absorbent member 10H. From this viewpoint, the total constituent fibers in the middle region M of the absorbent member 10H have a degree of orientation of 1.2 or higher, preferably 1.4 or higher. The recited degree of orientation is higher than that of staple fibers in a carded web obtained by carding staple fibers. Where, in particular, the staple fibers 412 present in the middle region M are oriented in the longitudinal direction of the absorbent member 10H, a fluid discharged in the middle region M is more smoothly drawn into the absorbent body 10H through a small planar area owing to the excellent downward wicking properties of the staple fibers 412. From this point of view, it is preferred that the degree of orientation of the staple fibers 412 be 1.2 or higher, more preferably 1.3 or higher, even more preferably 1.4 or higher.

The degree of orientation of the whole web can be measured with a microwave molecular orientation analyzer MOA-2001A from Kanzaki Co., Ltd. Before measurement, a load of 24.5 kPa is applied to an absorbent member to be measured for 12 hours to eliminate the influences of thickness recovery, wrinkles, and the like. In the case when the absorbent member is taken from a product, a load is previously applied to the product in the same manner, and the absorbent member taken out from the thus conditioned product is further treated by load application in the same manner. The absorbent member must be removed from the product while retaining its structure so as to minimize error of measurement. For this, it is advisable to mark the product with a frame of prescribed size for sampling and take out a sample without distorting the frame.

A sample is taken along the longitudinal direction of the absorbent member and set on the analyzer with its length vertical. The sampling size depends on the analyzer. The product may be designed to have the fibers of the absorbent member oriented in either the longitudinal or width direction of the absorbent member. In this case, the sample is set on the analyzer with the fiber orientation direction vertical. As long as the measured value falls within the recited range, the fibers are regarded as being oriented.

A case is assumed in which the superabsorbent polymer in the absorbent member hinders the measurement. In such a case, the absorbent member is sandwiched between metal meshes or something to fix the structure, dipped in an ascorbic acid solution, exposed to sunlight to dissolve the superabsorbent polymer, and washed with water, and the degree of orientation of the residual fibers is measured.

The degree of orientation of only the staple fibers or the continuous fibers can be measured as follows. The degree of orientation of the web is measured beforehand. The proportions of the staple fibers and the continuous fibers in the measurement area to be measured are then determined. Where the proportion of the staple fibers or the continuous fibers exceeds 80%, the degree of orientation of the total fibers of that area of the web is regarded as the degree of orientation of the fibers existing in a proportion exceeding 80%. Where the continuous fibers to staple fibers ratio is 20/80 to 80/20, staple fibers are appropriately drawn out evenly throughout the whole area of a sample, followed by measuring the degree of orientation of the sample. Drawing the staple fibers and the subsequent measurement are repeated. For every measurement, the continuous fibers/staple fibers ratio of the sample is calculated from the amount of the fibers drawn out, and the measured orientation degree is plotted against the continuous fibers/staple fibers ratio. The degree of orientation of the staple fibers or the continuous fibers is obtained by extrapolating the resulting plot.

When the absorbent member 10H receives a considerable quantity of a fluid in a short time or acquires large quantities of a fluid after long time use, the fluid can diffuse to the side regions S. Since there are continuous fibers 411 in the side regions S oriented in the longitudinal direction of the absorbent member 10H, the fluid having reached the side regions S well spreads in the longitudinal direction of the absorbent member 10H (the front-to-rear direction of a wearer) as depicted in FIG. 32, while being suppressed from spreading across the side regions S. As a result, leakage from both side edges of the absorbent member 10H is prevented effectively, and a large area of the absorbent member can be made effective use of. To ensure this effect, it is preferred that the degree of orientation of the continuous fibers 411 be 1.2 or higher, more preferably 1.4 or higher. The degree of orientation of the continuous fibers 411 can be measured in the same manner as for the stable fibers 412.

Specific methods for orienting the continuous fibers 411 and the staple fibers 412 will be described later with respect to the method of producing the absorbent member 10H.

To further ensure the above-described effects, it is preferred that the basis weight of the continuous fibers in the absorbent member 10H be 10 to 100 g/m² and that that of the staple fibers be 10 to 100 g/m². A preferred weight ratio of the continuous fibers 411 to the staple fibers 412 is 5/95 to 80/20, more preferably 20/80 to 50/50.

To the same effect, the basis weight of the absorbent polymer is preferably 10 to 500 g/m², and the weight ratio of the web 413 containing the continuous fibers 411 and the staple fibers 412 to the absorbent polymer is preferably 1/0.5 to 1/15, more preferably 1/2 to 1/10.

To prevent side leakage that can occur when the absorbent member 10H is incorporated in an absorbent article, the width W1 (see FIG. 30) of the region where the absorbent polymer 414 is distributed (equal to the width of the middle region M) along the width direction of the absorbent member 10H is preferably 20% to 95%, more preferably 50% to 85%, of the total width W (see FIG. 30) of the absorbent member 10H, and the total of widths W2 (see FIG. 30) of the regions where the absorbent polymer is absent (equal to the total width of the side regions S) is preferably 5% to 80%, more preferably 15% to 50%, of the total width W of the absorbent member 10H.

The continuous fibers 411 are preferably crimped continuous fibers. The percent of crimp (JIS L0208) of the continuous fibers 411 is preferably 10% to 90%, more preferably 10% to 60%, even more preferably 10% to 50%. The absorbent member 10H which contains crimped continuous fibers 411 is flexibly deformable as a whole and, as assembled into an absorbent article, exhibits improved fit against a wearer's body or improved deformability to form a concave shape to enhance leak prevention.

Similarly, the staple fibers 412 are preferably crimped fibers. The crimp percentage of the crimped staple fibers 412 is preferably equal to that of the crimped continuous fibers 411. The absorbent polymer 414 can be held more stably by the crimped staple fibers 412 in the web 413 and is thereby effectively prevented from moving in or falling off the web 413.

The crimp of the continuous and the staple fibers may be either two-dimensional or three-dimensional. The percentage of crimp is defined to be a percentage of a difference between the length A of a crimped fiber in its straightened state and the natural length B of the crimped fiber to the length A, being calculated from equation:

Percentage of crimp (%)=$((A-B)/A) \times 100$

The natural length of a crimped fiber is the length of the straight line connecting the two ends of a fiber in its natural state. The term "natural state" means a state of a fiber hanging under its own weight with its one end fixed to a horizontal plate. The term "straightened state" means a state of a fiber stretched out until no crimp remains under a minimum load. The number of crimps of the crimped continuous fibers 411 and the crimped staple fibers 412 having the recited percentage of crimp is preferably 2 to 25, more preferably 4 to 20, even more preferably 10 to 20, per centimeter.

The continuous fibers 411 are preferably hydrophilic. Hydrophilic continuous fibers 411 may be those essentially having hydrophilicity and/or those which are not essentially hydrophilic but have been rendered hydrophilic by hydrophilization treatment. Preferred examples of the hydrophilic continuous fibers essentially having hydrophilicity include cellulose acetate fibers and rayon fibers. A web of cellulose acetate fibers is particularly preferred for its capability of maintaining bulkiness even after being wetted. Cellulose triacetate fibers and/or cellulose diacetate fibers are preferred cellulose acetate fibers. Nylon or acrylic fibers are also useful as hydrophilic continuous fibers 411.

Similarly to the continuous fibers 411, the staple fibers 412 are preferably hydrophilic. The description on the material and the like of the continuous fibers 411 applies to the staple fibers 412. The staple fibers 412 may be of the same material as or a different material from that of the continuous fibers 411.

In the case when the continuous fibers 411 and/or the staple fibers 412 are hydrophilic, their moisture regain is preferably less than 10%, more preferably 1% to 8%, to secure liquid permeability. When the moisture regain is less than 10%, the fibers are prevented from being plasticized and softened or from swelling and causing clogging even on absorbing water. Furthermore, fibers having an excessively high moisture regain tend to form hydrogen bonds between themselves or between different sites of the individuals because of moisture absorption or their own strong hydrophilic properties particularly, when compressed in the manufacture of the absorbent article to adjust the thickness or when the absorbent article is left compressed, e.g., in a package for a long period of time. As a result, an absorbent member having such fibers tends to become hard to reduce wearing comport and cause skin troubles by friction. The moisture regain is measured in accordance with the method described in JP 7-24003, para. [0025].

The terminology "continuous fiber" as used in the third aspect of the invention refers to a fiber having a fiber length preferably of 70 mm or longer, more preferably 80 mm or longer, even more preferably 100 mm or longer, as measured by the mean fiber length measurement method (method C) specified in JIS L1015. In cases where the whole length L (see FIG. 30) of a web per se is shorter than 100 mm, for example, where the whole length of the absorbent article is less than 100 mm, a fiber having a length of at least 50%, more preferably 70% or more, even more preferably 80% or more, of the whole length L of the web is defined to be "a continuous fiber". The continuous fibers used in the present invention are generally termed "continuous filaments". A bundle of continuous filaments is generally termed "a tow". Accordingly, the terminology "continuous fiber" as used herein shall include a continuous filament.

The terminology "staple fiber" as used with respect to the third aspect of the invention denotes a fiber having a fiber length of less than 70 mm, more preferably 5 mm or more and less than 70 mm, even more preferably 10 to 50 mm, as measured in the same manner as for the continuous fibers. Pulp fiber commonly used in the art as an absorbent member of an absorbent article is not included under the term "staple fiber". In other words, the term "staple fiber" as used in the invention denotes fibers other than pulp fiber.

It is preferred that the continuous fibers and the staple fibers of the web 413 be not bonded to each other, i.e., between staple fibers, between continuous fibers, and between a continuous fiber and a staple fiber. As used herein, the term "bonded" refers to a state in which fibers are bonded to one another through fusion or with an adhesive substantially throughout the web such that the bonds are maintained even when the absorbent polymer absorbs a fluid and swells. The term does not include a state in which fibers are bonded to one another via a water-soluble binder while dry but become able to move relative to one another as a result of dissolving the binder when wetted. Neither does the term include a state in which fibers in a small part of the web are bonded to one another via an adhesive applied to an interface between the web and other member to be combined with. The staple fibers and the continuous fibers present in the web 413 may or may not be entangled with one another, i.e., between staple fibers, between continuous fibers, or between a staple fiber and a continuous fiber. Entanglement of the fibers can be effected by, for example, hydroentanglement or needle punching.

The fineness of the continuous fibers 411 and the staple fibers 412 used in the present embodiment is not particularly limited. The continuous fibers 411 and the staple fibers 412 both preferably have a fineness of 1.0 to 10 dtex, more preferably 1.5 to 8 dtex. The continuous fibers 411 and the staple fibers 412 may have the same or different fineness.

The particles 414 are then described in detail. The particles 414 used in the present embodiment are preferably particles of an absorbent polymer, more preferably lumpy particles of a superabsorbent polymer. Since the web of the invention is highly oriented, the superabsorbent polymer particles are less liable to be caught between the fibers and to achieve a high ratio of the superabsorbent polymer to the fiber. By using superabsorbent polymer particles of lumpy shape (or angular shape, inclusive of agglomerates, preferably having a bulk density of 0.5 to 0.8 $g/cm^3$, more preferably 0.6 to 0.8 $g/cm^3$), entanglement with the fibers increases so that the web is able to hold the superabsorbent polymer in a high concentration. The lumpy absorbent polymer particles are obtained by casting a water-containing gel of an absorbent polymer synthesized by solution polymerization into a sheet, drying the cast sheet, and grinding the dried sheet, or the lumpy absorbent polymer particles are agglomerates of irregular particles formed by reverse phase suspension polymerization using a selected surface active agent under a controlled stirring force. The lumpy absorbent polymer particles preferably have an average particle size of 150 to 600 μm, more preferably 200 to 500 μm.

In an embodiment where porous particles such as activated carbon or silica gel are used as the particles 414, such lumpy particles preferably have an average particle size of 20 to 300 μm, more preferably 50 to 150 μm.

Examples of the absorbent polymer include those conventionally used in absorbent members of disposable diapers, sanitary napkins, and the like, such as sodium polyacrylate, acrylic acid-vinyl alcohol copolymers, crosslinked sodium polyacrylate, starch-acrylic acid graft polymers, isobutylene-maleic anhydride copolymers and saponification products thereof, potassium polyacrylate, and cesium polyacrylate.

In view of reduction of the amount of the absorbent polymer to be used and prevention of reduction in gel feel after fluid acquisition, it is preferred that the absorbent polymer have a physiological saline absorption of 30 g/g or more, more preferably 30 to 50 g/g, measured by a centrifugal dewatering method. The physiological saline absorption measurement by a centrifugal dewatering method is carried out as previously described.

The absorbent member having a web of highly oriented fibers as in the third aspect of the invention is excellent in liquid spreading properties. To ensure the effect, it is preferred to use a superabsorbent polymer having high liquid permeability. To effectively prevent gel blocking of the absorbent polymer from occurring, it is more preferred to use an absorbent polymer having high liquid permeability under load. Specifically, the absorbent polymer preferably has a liquid permeation rate of 30 to 300 ml/min, more preferably 32 to 200 ml/min, even more preferably 35 to 100 ml/min. Using an absorbent polymer the liquid permeation rate of which is within the recited range is effective to reduce occurrence of the gel blocking problem that the absorbent polymer particles swollen with a fluid to saturation are liable to stick to one another under load and obstruct passage of liquid. With the liquid permeation rate being in that range, fluid fixation can be achieved sufficiently to prevent leakage from occurring even when a large amount of excrement is discharged at a time, or when excrement is released very fast as by older babies or by adults, or when the absorbent member is designed to have a reduced thickness. The measurement of the liquid permeation rate is conducted under a load of 2.0 kPa. The load of 2.0 kPa practically corresponds to the body pressure imposed to an absorbent member while an absorbent article is worn. The method of measurement is specifically described, e.g., in JP 2003-235889, para. [0005]. In the present invention, the liquid permeation rate measurement is carried out by changing the sample weight from 0.200 g as specified in the above publication to 0.32 g. More specifically, the liquid permeation rate is measured according to the following procedures.

Method of Measuring Liquid Permeation Rate:

A filtration cylinder (inner diameter: 25.4 mm) equipped at the lower open end thereof with a metal mesh (mesh size: 150 μm) and a narrow tube (inner diameter: 4 mm; length: 8 cm) with cock (inner diameter: 2 mm) is prepared. The cylinder with the tube closed with the cock is vertically held, and 0.32 g of a sample having a particle size adjusted to 150 to 850 μm is put therein. Then, 50 ml of 0.9 wt % physiological saline is poured in the cylinder. After allowing the cylinder to stand for 30 minutes from the start of pouring the physiological saline, a circular rod weighing 21.2 g and having attached to one end thereof a metal mesh having a mesh size of 150 μm and a diameter of 25 mm is inserted in the filtration cylinder until the metal mesh comes into contact with the sample. One minute later, a 77.0 g weight is attached to the circular rod to apply an appointed load to the sample. After the cylinder is left to stand for an additional 1 minute period, the cock is opened, and the time T1 (sec) required for the liquid level of the saline to drop from the 40 ml mark to the 20 ml mark is measured. The liquid transit time is calculated according to formula below using the thus measured time T1 (sec). In the formula T0 is the time measured with no sample in the filtration cylinder.

Liquid permeation rate (ml/min)=20×60/(T1−T0)

A more specific description about the method of liquid permeation rate measurement is given in JP 2003-235889, paras. 0008 and 0009. Equipment used therefor is illustrated in FIGS. 1 and 2 of the same publication.

In order for the absorbent member 10H having so increased liquid spreading properties due to the highly oriented fibers to retain a fluid without fail, it is desirable for the absorbent polymer to have a sufficiently high absorption rate. The absorption rate of the absorbent polymer is represented by the vortex method, which is known to represent a liquid fixing ability of a superabsorbent polymer when the superabsorbent polymer is forcedly exposed to a liquid. The demand wettability (DW) method is also known as a test method for representing the absorption rate of a superabsorbent polymer. However, the DW method is a test for evaluating all together both the ability of a superabsorbent polymer to vertically wick liquid and the ability of a superabsorbent polymer gel to acquire liquid. Because a web having highly oriented fibers as in the present invention exhibits sufficient liquid spreading properties, it is recommended to represent the absorption rate in terms of vortex time measured by the vortex text method in which an absorbing ability in forced exposure to liquid is evaluated rather than the ability of wicking liquid. The absorbent polymer has a vortex time of 5 to 60 seconds, preferably 10 to 50 seconds, more preferably 15 to 40 seconds, as measured by the vortex method. A superabsorbent polymer showing a vortex time shorter than 5 seconds absorbs a fluid too fast to exhibit the liquid spreading properties, one of the features of the present invention. A superabsorbent polymer having a vortex time longer than 60 seconds is liable to fail to hold a fluid in the absorbent member, tending to cause leakage.

The vortex test was carried out in accordance with JIS K7224-1996. Specifically, 50 g of a 0.9 wt % sodium chloride aqueous solution (physiological saline, from Otsuka Pharmaceutical Co., Ltd.) is measured into a beaker and stirred on a magnetic stirrer at 600±60 rpm to create a vortex. A superabsorbent polymer weighing 2.0 g is poured into the vortex, and the time required for the stir bar to be covered by the saline is recorded. In this way, the absorption rate as measured by the vortex test being represented in terms of "time" in the present embodiment, a shorter vortex time indicates a higher absorption rate. In the description of the present invention both the terms "absorption rate" and "vortex time" are measures for the rate of absorption. The rate of absorption can be designed by the shape, size, bulk density, and degree of crosslinking of the superabsorbent polymer.

In order for the absorbent polymer to satisfy the above-mentioned characteristics, a crosslinking density gradient is provided on the surface of the absorbent polymer particles, or aspherical, irregularly shaped absorbent polymer particles are used. Specifically, the methods disclosed in JP 7-184956A, col. 7, line 28 to col. 9, line 6 can be used.

A superabsorbent polymer having a high liquid permeation rate and a high absorption rate as described may be used alone or may be used as a mixture with or in combination with another absorbent polymer whose liquid permeation rate or absorption rate falls in the above-specified preferred range. For example, an absorbent polymer S1 having a relatively high liquid permeation rate and an absorbent polymer S2 having a relatively high absorption rate can be used as a mixture. Comparing the absorbent polymers S1 and S2, the absorbent polymer S2 has a higher absorption capacity and a higher absorption rate but is less resistant to gel blocking. In the system containing both the absorbent polymers S1 and S2, the absorbent polymer S1, which is harder and less likely to induce gel blocking, enters between the particles of the absorbent polymer S2 having higher absorbency. As a result, the absorbent member can be made more effective use of.

In another example, an absorbent polymer S3 having a relatively high liquid permeation rate and an absorbent polymer S4 having a relatively high absorption rate may be used in combination. In this example, the absorbent polymer S3 having a high liquid permeation rate is distributed in and in the vicinity of the target zone of an absorbent article (corresponding to about second to fourth sections from the frontal end of an absorbent member divided into five equal sections in its longitudinal direction), and the superabsorbent polymer S4 is disposed near the frontal and rear ends of the absorbent member, thereby increasing the fluid acquisition speed of the absorbent member and enhancing fluid fixing performance. In still another example, the superabsorbent polymer S3 having a high liquid permeation rate may be disposed in the central portion of the absorbent member (with the absorbent member being divided into five equal sections in both the longitudinal and lateral directions, the central portion corresponds to the second to fourth sections from the front and to the second to fourth sections from either lateral side), while the superabsorbent polymer S4 having a high absorption rate is disposed to surround the superabsorbent polymer S3 with a high liquid permeation rate. In yet another example, the same effect is obtained by distributing the superabsorbent polymer S3 having a high liquid permeation rate and the superabsorbent polymer S4 having a high absorption rate on the topsheet side and the backsheet side, respectively.

The absorbent member 10H of the present embodiment may contain a buffering agent of various kinds, either organic or inorganic, so that a buffer system may be provided when the absorbent member 10H absorbs a bodily waste. Examples of useful buffers include acetic acid, phosphoric acid, citric acid, succinic acid, adipic acid, malic acid, lactic acid, and their salts, used either alone or in combination thereof, and various amino acids. Additionally, the organic or inorganic buffers neutralize ammonia resulting from decomposition of body wastes, e.g., urine, thereby serving to maintain a diaper neutral to weakly acidic. This will lessen the adverse influences of body wastes on the skin if a body waste should rewet the skin. In the case when fibers having an ester bond in the molecule thereof such as cellulose acetate fibers are used as the continuous fibers 411, the alkali (e.g., ammonia) neutralizing function of the organic or inorganic buffer is expected to prevent the fibers from being damaged due to alkali-decomposition of the ester bonds.

Other organic or inorganic particles serving as a deodorant or an antimicrobial agent may be used as the particles 414 in place of, or in combination with, the absorbent polymer particles. Examples of such organic or inorganic particles include cellulose powder, activated carbon, silica, alumina, and various minerals (e.g., zeolite, sepiolite, bentonite, and cancrinite). The inorganic particles may have part of their metal sites replaced. The particles may be used as agglomerates thereof or as a composite with a carrier. These particles may be used in combination of two or more thereof. The agglomerates or composites with a carrier preferably have an average particle size of 150 to 600 µm, more preferably 200 to 500 µm. The action of these components is to subdue the odors of bodily wastes absorbed by the absorbent member 10H or the odors originated in the material of the absorbent member.

The web 413 may further contain hydrophilic powder for the purpose of enhancing the increase of absorption rate and of improving the liquid retentivity and a dry feel. Examples of the hydrophilic powder include fibrillated or non-fibrillated cellulose powder, carboxymethyl cellulose and its metal salts, carboxyethyl cellulose and its metal salts, hydroxyethyl cellulose and its derivatives, silk powder, and nylon powder. Preferred of them is cellulose powder; for it achieves the highest degrees of the above-mentioned effects. The hydrophilic powder may be spread either before spreading the absorbent polymer or simultaneously with the absorbent polymer in the form of a blend with the absorbent polymer.

When the absorbent member 10H is embossed, a large number of debossed portions where the web 413 is densified are formed. That is, the embossed web 413 has high fiber density portions and low fiber density portions. As a result, a difference of capillarity is created between the high density portions and low density portions, which brings about improved wicking properties of the absorbent member. It is preferred to form a number of the densified portions in the region where the staple fibers exist to bring about improved liquid drawing properties in that region to ensure downward wicking properties (with minimized planar spread). The region having the staple fibers with improved wicking properties allows little liquid to remain on the surface and keeps the skin dry. The shape of the embossed (debossed) portions is chosen from circles, oblong rectangles, squares, lines, etc., taking wicking properties, aesthetics, and the like into consideration. The region having the continuous fibers, on the other hand, is preferably not subjected to such an embossing treatment that works to hinder liquid diffusion, for example, an embossing treatment of a line pattern perpendicular to the fiber orientation direction.

In order to enhance the downward wicking properties and to improve the shape retention of the web 413, a sheet or a plurality of sheets made of paper, nonwoven fabric, etc. may be superposed on or wrapped around the upper and/or lower side of the web 413 and/or the side portions of the web 413 and joined to the web 413 with an adhesive or by heat fusion. By so doing, an absorbent member of sheet form is obtained, in which the web 413 is held in between a pair of sheets. Such an absorbent member of sheet form has increased stiffness due to the joint with the sheets and the stiffness of the sheets per se and therefore exhibits improved handling properties and can easily be transported alone. Furthermore, the absorbent member of sheet form can easily be trimmed or punched into any desired contour in conformity to the contour of an absorbent article.

When the sheet and the web are joined with an adhesive to increase the shape retention of the web 413, the adhesive is preferably applied so as not to impair water permeability, softness, and breathability of the web 413. It is advantageous for this that the adhesive be applied in as fine a line as possible in a discontinuous pattern such as an array of spirals, separate lines, or "omega" shaped lines. Fibers can thus be bonded at a number of joints without ruining the characteristics of the web 413. This can be achieved by using, for example, UFD Fiber (trade name), a kind of hot melt adhesive applicator. Any type of adhesives, either hydrophilic or hydrophobic, may be used with no limitation. A hydrophilic adhesive is preferred. A useful hydrophilic adhesive is exemplified by Cycloflex (registered trade name of a hydrophilic hot melt adhesive from National Starch & Chemical Corp., Delaware, U.S.A.). Although the adhesion between the sheet and the web 413 is between the surfaces of the two adherents, the term "adhesion" as used here includes incidental adhesion between fibers in the thickness direction of the web 413 because the adhesive may penetrate into the web 413.

To superpose the sheet on the upper side and/or the lower side of the web 413 is advantageous to enhance the absorbing performance of the absorbent member 10H. To increase the absorbing performance of the absorbent member 10H, it is preferred to use a fiber sheet or a fiber web as the sheet. Examples of such a sheet material include air-through nonwovens, air-laid nonwovens, dry processed pulp nonwovens, crosslinked pulp, paper containing crosslinked pulp, and composites of the sheet materials recited. These sheets may be used singly, or a plurality of the sheets may be used as a stack.

The fibers making up the sheet preferably have a fineness of 1.7 to 12 dtex, more preferably 2.2 to 7.8 dtex, even more preferably 3.3 to 5.6 dtex. The sheet preferably has a basis weight of 15 to 200 g/m$^2$, more preferably 20 to 150 g/m2, even more preferably 25 to 120 g/m$^2$. When it is demanded to improve the rate of fluid acquisition, to prevent rewet, or to facilitate fluid diffusion in the sheet, it is preferred to use a sheet having a basis weight of 15 to 100 g/m$^2$, more preferably 20 to 80 g/m$^2$, even more preferably 25 to 50 g/m$^2$. When it is demanded to improve the cushioning properties of the absorbent member 10H, to prevent the absorbent member 10H from bunching up, to impart recovery from compression to the absorbent member 10H, or to suppress dissipation of water vapor from the absorbent member 10H, it is preferred to use a sheet having a basis weight of 25 to 200 g/m$^2$, more preferably 30 to 150 g/m$^2$, even more preferably 40 to 120 g/m$^2$.

The wrap sheet 416 is preferably a water permeable sheet material such as a pulp sheet (e.g., tissue paper) or a water permeable nonwoven fabric.

Figure 33:
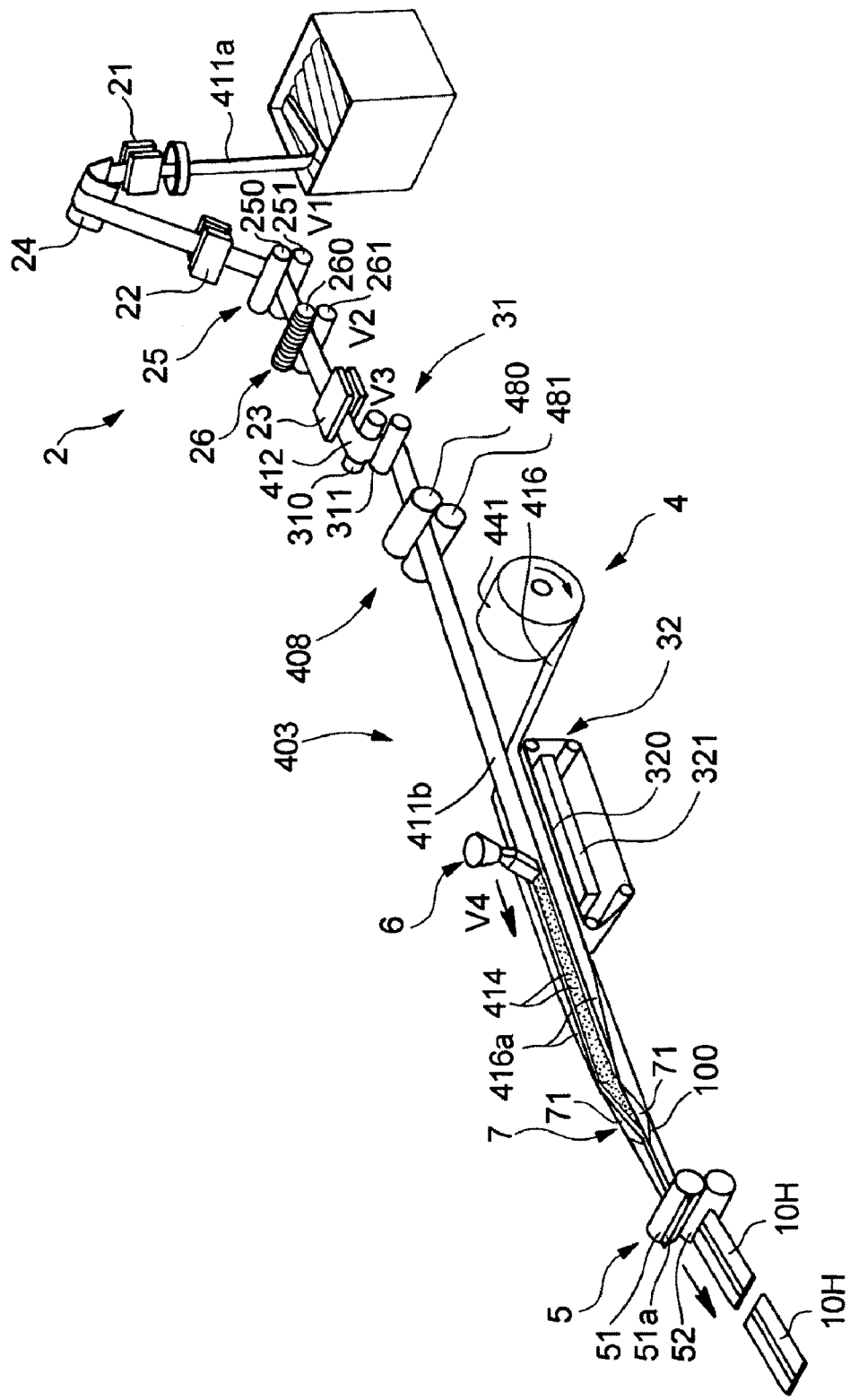
FIG. 33 is a perspective illustrating the steps of one embodiment of the method of producing the absorbent member according to the invention with the apparatus for carrying out it.

A preferred method of preparing the absorbent member 10H will then be described by way of FIG. 33. The apparatus of producing an absorbent member shown in FIG. 33 includes a tow opening mechanism 2 in which a continuous filament tow 411a is opened while being conveyed under tension in the machine direction to form an opened tow 411b; a tension relaxing mechanism 403 in which the opened tow 411b is relieved from the tension and conveyed to the position where a polymer 414 is fed; a fiber cutting mechanism 408 in which the continuous filaments in part of the opened tow 411b are cut; a wrap sheet feeding mechanism 404 for feeding a wrap sheet 416 on one side of the opened tow 411b; an absorbent polymer feeding mechanism 6 for feeding an absorbent polymer 414 on the side of the opened tow 411b opposite to the side of the wrap sheet 416; and a folding mechanism 7 in which both lateral side portions 416a of the wrap sheet 416 extending from both edges of the opened tow 411b are folded over the other side to cover both sides of the opened tow 411b.

The tow opening mechanism 402 has the same structure as in the apparatus of producing an absorbent member illustrated in FIGS. 4 and 23 and opens a tow 411a in the same manner.

The continuous fibers forming the opened tow 411b are in a mutually intertwined and highly oriented state. The continuous fiber cutting mechanism 408 includes a pair of rollers 480 and 481, between which the opened tow 411b is compressed under pressure in its thickness direction. The rollers 480 and 481 have gears meshing with each other on their respective laterally middle portions. While the web is passing therebetween, part of the fibers of the web are cut at the nip of the meshing gears to create staple fibers. The width of the nip between the rollers 480 and 481 (in the direction perpendicular to the continuous-form absorbent member 100) is substantially the same as the width of the polymer feed port in the same direction. In the mean time, the continuous fibers remaining non-cut in both lateral side portions of the web provides the whole web with tension. The tension relaxing mechanism 403 described below is adjusted, taking into account the influences of the continuous fiber cutting mechanism 408.

The continuous filaments can be cut by a known method, for example, introducing the opened tow into the bite between rollers having a number of slits as described above, or cutting the continuous filaments with a cutter blade, a water jet, a laser beam, etc. Because the continuous filaments F have crimps and get entangled with each other upon being cut, the web with part of the continuous filaments cut can be transported on a conveyor, etc. as such.

The tension relaxing mechanism 403 includes a feed unit 31 downstream the banding jet 23 and a vacuum conveyor 32. The feed unit 31 has a pair of rollers 310 and 311 rotatably driven at a speed lower than the peripheral speed V2 of the blooming unit 26. The feed unit 31 is configured to superpose the opened tow 411b, which is obtained by opening the tow 411a in the tow opening mechanism 2, on the upper side of a wrap sheet 416 fed on the vacuum conveyor 32 while giving the opened tow 411b a tension lower than the tension applied between the pre-tensioning unit 25 and the blooming unit 26. The vacuum conveyor 32 has an air-permeable endless belt 320 driven at a running speed V4 that is still lower than the feeding speed V3 of the feed unit 31 (i.e., the peripheral speed of the pair of rollers 310 and 311) and a suction box 321. The opened tow 411b superposed on the wrap sheet 416 running on the vacuum conveyor 32 is further conveyed by the endless belt 320 to the polymer feed position while being relaxed from the tension.

The wrap sheet feeding mechanism 4 is configured to feed the wrap sheet 416 to one side of the opened tow 411b. The wrap sheet feeding mechanism 4 includes means for unrolling the wrap sheet 416 and a guide roller (not shown) for guiding the unrolled wrap sheet 416 to the vacuum conveyor 32. The unrolling means has a roll 441 of the wrap sheet 416 and a drive unit (not shown) for unrolling the roll 441.

The absorbent polymer feeding mechanism 6 is configured to spread absorbent polymer particles 414 from a polymer feed port placed above the upper side (opposite to the side of the wrap sheet 416) of the opened tow 411b. The suction box 321 is provided on the opposite side of the upper run of the endless belt 320 to the polymer feed port. The absorbent polymer 414 is spread while being sucked from the opposite side of the opened tow 411b by the suction box 321. The width of the polymer feed port in the direction perpendicular to the running direction (longitudinal direction) of the opened tow 411b is smaller than the width of the opened tow 411b so that the polymer 414 may be distributed in only the middle portion having a predetermined width of the opened tow 411b.

The folding mechanism 7 has a folding guide 71 on both sides of the machine direction. While the wrap sheet 416 is continuously transported under tension by the pair of rollers 480 and 481 of the continuous fiber cutting mechanism 408, the side portions 416a thereof laterally extending from both edges of the opened tow 411b are folded over the upper side of the opened tow 411b as guided by the guides 71 to cover the upper side of the opened tow 411b. Thus, the opened tow 411b has its both upper and lower sides covered by the wrap sheet 416.

Downstream the folding mechanism 7 is provided a cutting mechanism 5 which cuts the continuous-form absorbent member 100. The continuous-form absorbent member cutting mechanism 5 includes a cutter roller 51 having a cutting blade 51a extending in the axial direction and an anvil roller 52 and is configured to cut the continuous-form absorbent member 100 into the length of individual absorbent members, each of which is to be assembled into an absorbent article.

The absorbent member 10H is produced by use of the above-described apparatus as follows. As illustrated in FIG. 33, in the tow opening mechanism 2, a tow 411a of crimped continuous filaments is continuously drawn and spread by applying compressed air in the banding jets 21 to 23 and by stretching taking advantage of the peripheral speed difference between the pre-tensioning unit 25 and the blooming unit 26. The resulting opened tow 411b is transported through the feed unit 31 and superposed on the wrap sheet 416 supplied on the vacuum conveyor 32.

The continuous filaments are cut into staple fibers by the continuous fiber cutting mechanism 408 between the feed unit 31 and the vacuum conveyor 32. The continuous filament cutting is done in a region which includes at least a region where the absorbent polymer 414 is to be spread and which is pressed in the nip between the rollers 480 and 481. The continuous filaments F are cut into staple fibers 412 on being pressed against the edge of the gear teeth. The orientation direction of the thus produced staple fibers 412 is substantially the same as that of the continuous filaments F before being cut. That is, the orientation direction of the continuous filaments before being cut is maintained after the cutting step. In this manner, a web 413 composed of continuous fibers 411, which are continuous filaments F remaining non-cut, and the staple fibers 412 produced by cutting the continuous filaments F is formed from the opened tow 411b.

While the opened tow 411b and the wrap sheet 416 are transported by the vacuum conveyor 32, the absorbent polymer 414 is spread on the opened tow 411b by the absorbent polymer feeding mechanism 6. The absorbent polymer 414 is spread in only a prescribed width in the laterally middle portion of the opened tow 411b. The spreading is continuous in the longitudinal direction of the opened tow 411b. The amount of the absorbent polymer 414 to be spread is preferably equal to or greater than, more preferably twice or more times, even more preferably three or more times, the basis weight of the opened tow 411b. When, for example, the opened tow 411b has a basis weight of 30 g/m$^2$, the amount of the absorbent polymer 414 to be spread is preferably 30 to 400 g/m$^2$, more preferably 60 to 300 g/m$^2$.

In the present embodiment, the opened tow 411b obtained by opening the tow 411a is superposed on the wrap sheet 416 in a state contracted as compared with the most stretched state while being opened. More specifically, the opening of the tow 411a is effected by driving the blooming unit 26 at a peripheral speed V2 that is higher than the peripheral speed V1 of the pre-tensioning unit 25. On the other hand, the running speed V4 of the wrap sheet 416 (equal to the running speed of the endless belt 320 of the vacuum conveyor 32) is lower than the peripheral speed V2 of the blooming unit 26. That is, the tension imposed to the opened tow 411b is relaxed on the vacuum conveyor 32 to cause the continuous filaments to develop crimps. In that way, the preferred crimp percentages of the continuous fibers 411 and the staple fibers 412 recited previously can be achieved efficiently. In the present embodiment, the most stretched state of the tow 411a while being opened is the stretched state between the pre-tensioning unit 25 and the blooming unit 26.

The wrap sheet 416 used in the present embodiment has a width enough to cover both the upper and lower sides of the opened tow 411b. After the absorbent polymer 414 is supplied to the opened tow 411b, both side portions 416a of the wrap sheet 416 extending from both edges of the opened tow 411b are folded to cover the upper side of the opened tow 411b by the folding mechanism 7 as illustrated in FIG. 33.

The continuous-form absorbent member 100 is then cut by the continuous-form absorbent member cutting mechanism 5 into individual absorbent members 10H of a size appropriate to the type and size of an absorbent article in which the resulting absorbent member is assembled. According to the method of the present embodiment, the absorbent member 10H having the aforementioned structure can be produced efficiently and continuously.

While in the above method the continuous filaments F are cut under a compressing roller while the opened tow 411b has orientation under a controlled tension given thereto, controlled orientation of staple fibers may also be obtained by another method, in which a web having controlled orientation is made from staple fibers 412, and the absorbent polymer 414 is spread on the resulting web. This method produces the same effects as by the above described method.

In some detail, the method starts with the provision of a web with controlled fiber orientation. Previously prepared staple fibers are carded to form a web, which is heat treated.

At this stage, the degree of orientation of the web is less than 1.2. Then, a tension is applied to the web by, for example, stretching the web between sets of rollers rotating at different speeds, and the web stretched under tension is heat embossed to acquire higher fiber orientation. Heat embossing is not always needed because the stress is gradually relaxed to set the structure of the nonwoven fabric by taking up the web with the tension applied. The stretch ratio is adjusted appropriately by the processing conditions so as to result in a degree of orientation of 1.2 or higher. The staple fiber web prepared above is capable of laterally stretching.

FIGS. 34(a) through 34(e) are each a schematic representing another embodiment of the absorbent member according to the third aspect of the invention. In FIG. 34, a region RA hatched with solid lines from top left to bottom right is the area where the absorbent polymer is spread (equal to the distribution range of the absorbent polymer), and a region RB hatched with dotted lines from top right to bottom left is the area of the opened tow 411b that is compressed to produce staple fibers 412 of continuous filament origin.

In the absorbent member shown in FIG. 34(a), the region RB having distributed therein staple fibers oriented in the longitudinal direction of the absorbent member is included in the region RA having the absorbent polymer distributed. More specifically, the region RB having staple fibers is narrower than the region RA having the absorbent polymer distributed in both the longitudinal and lateral directions of the absorbent member. The absorbent member of FIG. 34(a) is produced by the above-described method of producing an absorbent member in which the roller 480 is a roller having a cutting section made of an elastic material and a non-cutting section made of a hard material such as a metal (inelastic material) alternating with each other in the circumferential direction on the peripheral surface thereof. The width of the cutting section in the direction perpendicular to the opened tow 411b is smaller than the width of the polymer feed port in the same direction. The part of the continuous filaments bitten between the roller 480 and roller 481 are cut.

In the absorbent member shown in FIG. 34(b), too, the region RB having distributed therein staple fibers oriented in the longitudinal direction of the absorbent member is included in the region RA having the absorbent polymer distributed. More specifically, the width of the region RB having staple fibers is smaller than that of the region RA having the absorbent polymer distributed in the lateral direction of the absorbent member, while the region RA having the absorbent polymer distributed and the region RB having the staple fibers have the same length in the longitudinal direction of the absorbent member. The absorbent member of FIG. 34(b) is obtained by the above-described method of producing an absorbent member in which the meshing nip of the rollers 480 and 481 has a smaller width than the polymer feed port in the direction perpendicular to the opened tow 411b.

In the absorbent member shown in FIG. 34(c), the region RA having the absorbent polymer distributed and the region RB having distributed therein the staple fibers oriented in the longitudinal direction of the absorbent member coincide with each other. The absorbent member of FIG. 34(c) is prepared by the above-described method of producing an absorbent member in which the absorbent polymer is spread intermittently and in which the rollers 480 and 481 have a biting cutting section, where the two rollers mesh with each other, and a non-cutting section (a non-biting section or a recess) alternating with each other. The width of the cutting section in the direction perpendicular to the opened tow 411b is equal to the width of the polymer feed port in the same direction.

In the absorbent members illustrated in FIGS. 34(d) and 34(e), the region RB having the staple fibers is narrower than the region RA having the absorbent polymer distributed. The absorbent member of FIGS. 34(d) and 34(e) are obtained by the above-described method of producing an absorbent member in which the rollers 480 and 481 have a biting cutting section, where the two rollers mesh with each other, and a non-cutting section (a non-biting section or a recess) alternating with each other. The width of the cutting sections in the direction perpendicular to the opened tow 411b is equal to the width of the polymer feed port in the same direction. The absorbent polymer is spread over the entire area of the web. In FIGS. 34(d) and 34(e), the continuous fibers are present in the area other than the region RB.

The absorbent member of the present invention may be designed to have a front and a rear end portion thereof composed of the continuous fibers 411 and have a portion composed of staple fibers 412 disposed between the front and the rear end portions as in the examples illustrated in FIGS. 34(a), 34(c), and 34(d). In such cases, it is preferred that the absorbent member have the continuous fibers 411 disposed in both the lateral side portions thereof such that the portion having the staple fibers 412 is surrounded by the portion having the continuous fibers 411 as shown in FIGS. 34(a), 34(c), and 34(d). It is not essential, nevertheless, for the absorbent member to have continuous fibers 411 on both lateral side portions thereof.

The absorbent member having any of the configurations of FIGS. 34(a) through 34(d) also exhibits excellent downward wicking properties in the region RB where staple fibers exist as oriented in the longitudinal direction. When assembled into an absorbent article such as a disposable diaper or a sanitary napkin with the region RB located in the target zone that is adapted to face a point of body fluid discharge of a wearer, the absorbent member 10H smoothly absorbs a body fluid discharged from the point of discharge (e.g., urine or menstrual blood) through a small planar area and stably retains the fluid in the absorbent polymer localized in that area. When a considerable quantity of a fluid is supplied to or absorbed by the absorbent member to reach the lateral side portions of the absorbent member, the fluid well spreads in the longitudinal direction of the absorbent member (the front-to-rear direction of a wearer) along the continuous fibers oriented in the longitudinal direction of the absorbent member. As a result, a large area of the absorbent member can be made effective use of, while diffusion of the fluid across the absorbent member is suppressed.

The absorbent member 10I illustrated in FIG. 35 is composed of an absorbent core 9 and a wrap sheet (not shown) wrapping the absorbent core 9. The absorbent core 9 is a dual layered web composed of an upper subweb 91 made mainly of staple fibers and a lower subweb 92 made mainly of continuous fibers. The wrap sheet covers the upper and lower sides and both side edge faces of the absorbent core 9 in the same manner as in the absorbent member 10H shown in FIGS. 30 and 31. The staple fibers in the absorbent member 10I are localized in the upper subweb 91 that is adapted to face the skin of a wearer as assembled into an absorbent article, while the continuous fibers are localized in the lower subweb 92 that is adapted to face the opposite side to the skin facing side. To put it another way, the continuous fibers and the staple fibers are localized in different positions in the thickness direction of the absorbent member 10I. The staple fibers are oriented in the longitudinal direction of the absorbent member 10I. The continuous fibers are also oriented in the longitudinal direction of the absorbent member 10I.

The upper subweb 91 preferably contains staple fibers in a proportion of 50% to 100%, more preferably 60% to 100%, even more preferably 80% to 100%, by weight based on the total fibers constituting the upper subweb 91. The lower subweb 92 preferably contains continuous fibers in a proportion of 50% to 100%, more preferably 60% to 100%, even more preferably 80% to 100%, by weight based on the total fibers making up the lower subweb 92.

The absorbent member 10I contains an absorbent polymer (not shown) as particles. The absorbent polymer particles may be distributed throughout the upper subweb 91 and the lower subweb 92, or the absorbent polymer particles may be distributed in only the upper subweb 91 or the lower subweb 92. That is, the absorbent polymer particles may be localized in a specific part in the thickness direction of the absorbent member 10I.

The absorbent member 10I shown in FIG. 35 exhibits excellent downward wicking properties in its upper subweb 91 containing the staple fibers. Therefore, an absorbent article such as a disposable diaper or a sanitary napkin having the absorbent member 10I incorporated therein with the upper subweb 91 facing a point of discharge of a wearer is able to smoothly wick a body fluid (e.g., urine or menstrual blood) discharged from a point of discharge through a small area of the absorbent member. When a considerable quantity of a fluid is supplied to or absorbed by the absorbent member to reach the lateral side portions of the absorbent member or the garment-facing surface of the upper subweb 91, the fluid well spreads in the longitudinal direction of the absorbent member (the front-to-rear direction of a wearer) along the continuous fibers oriented in the longitudinal direction of the absorbent member. As a result, a large area of the absorbent member can be made effective use of, while diffusion of the fluid in lateral direction of the absorbent member is suppressed to provide excellent protection against side leakage. While in the absorbent member 10I the upper subweb 91 is narrower than the lower subweb 92, the upper subweb 91 and the lower subweb 92 may have substantially the same width, or the upper subweb 91 may be made wider than the lower subweb 92.

The absorbent member 10I shown in FIG. 35 can be produced in accordance with the method of producing the absorbent member shown in FIGS. 30 and 31. For example, the absorbent member 10I which contains the absorbent polymer only in the upper subweb 91 is obtained using the apparatus illustrated in FIG. 33 as follows. The continuous filaments of the opened tow are cut into staple fibers over the whole width of the opened tow by a set of gears, and the absorbent polymer is spread on the staple fiber web over the whole width thereof to prepare an upper subweb 91. Separately, a tow of continuous filaments is opened to make an opened tow as a lower subweb 92. The upper subweb 91 is superposed on the lower subweb 92, and the laminate is wrapped in the wrap sheet to obtain the absorbent member 10I as designed.

Figure 36:
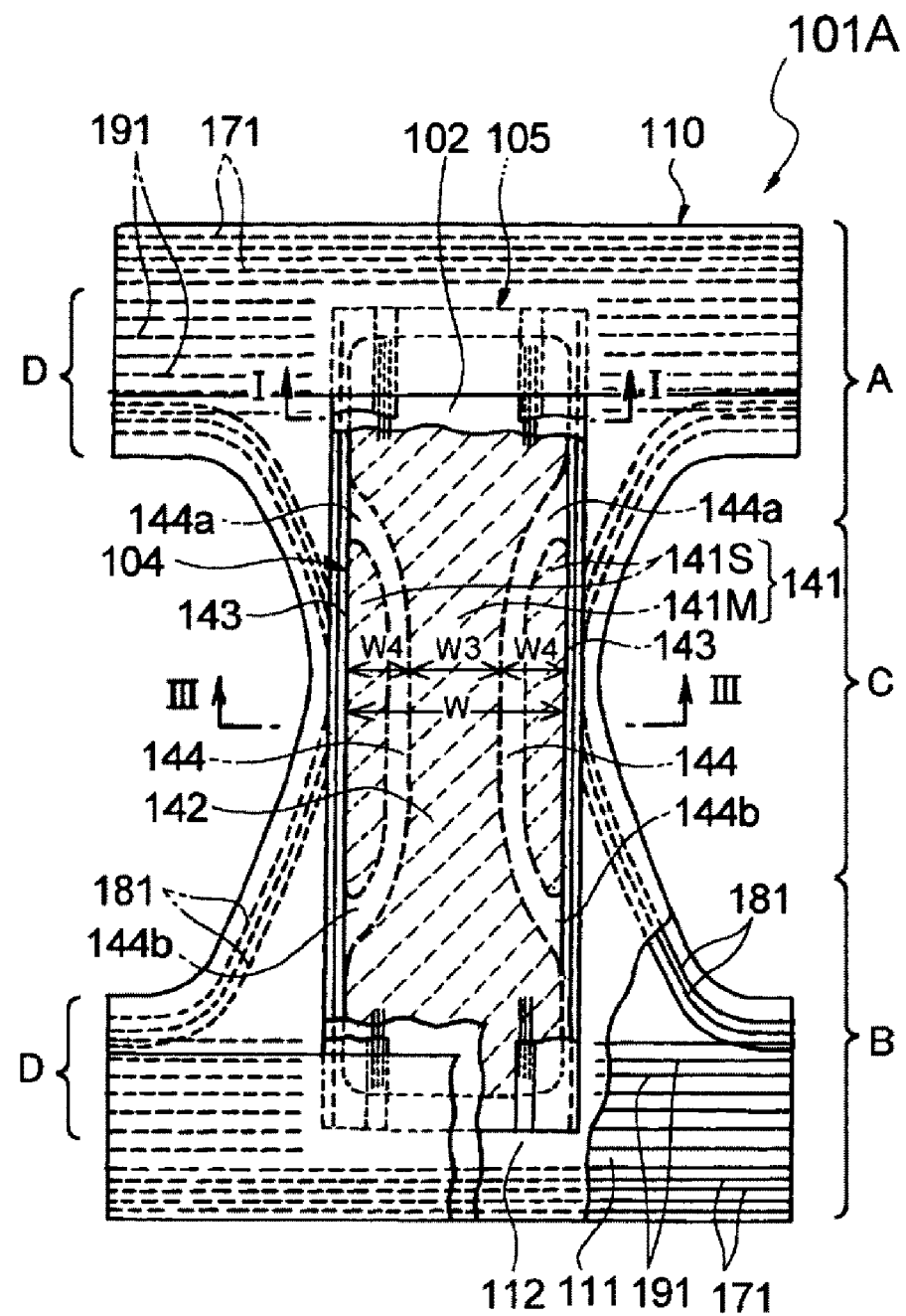
FIG. 36 is a developed plan of a disposable diaper (an embodiment of the absorbent article of the invention) in which a still another embodiment of the absorbent member according to the invention is used.

FIG. 36 illustrates an absorbent member 104 as still another embodiment of the third aspect of the invention, being assembled in a disposable pull-on diaper 101A as an absorbent article. Unless specifically described, the diaper 101A is equal to the diaper 101 previously described, so that the description on the diaper 101, inclusive of the preferred structure and configuration, appropriately applies to the diaper 101A. A cross-section of the diaper 101A taken along line I-I of FIG. 36 is equal to the cross-section of FIG. 9, and a cross-section of the diaper 101A during use taken along line III-III of FIG. 36 is equal to the cross-section of FIG. 10.

The second absorbent core 142 in the absorbent member 104 of the present embodiment is formed of the absorbent core 415 used in the absorbent member 10H illustrated in FIGS. 30 and 31. That is, the second absorbent core 142 contains continuous fibers and staple fibers both oriented in the longitudinal direction of the absorbent member 104 and an absorbent polymer. The second absorbent core 142 is a rectangle in a plan view extending over substantially the whole length of the absorbent assembly 105 inclusive of the absorbent member 104 and being slightly narrower than the width of the absorbent assembly 105. The first absorbent core 141 is composed of continuous fibers oriented in the longitudinal direction of the absorbent member 104. The absorbent polymer may be present or absence in the first absorbent core 141.

The absorbent member 104 of the present embodiment is rectangular as a whole in a plan view, with its length coincident with the front-to-rear direction of the diaper. The absorbent member 104 is wrapped in a water permeable wrap sheet (not shown), such as tissue paper or water permeable nonwoven fabric, and fixed between the topsheet 102 and the backsheet 103. The first absorbent core 141 and the second absorbent core 142 may separately be wrapped in the respective wrap sheets. The first absorbent core 141 and the second absorbent core 142 may or may not be joined together in parts with an adhesive.

In a modified embodiment, the second absorbent core 142 may contain the staple fibers in both the portion overlying the middle piece 141M of the first absorbent core 141 (the portion located between the opposite missing parts 144) and the portions overlying the side pieces 141S of the first absorbent core 141, while containing the continuous fibers in the portions overlying the missing parts 144 of the first absorbent core 141. In this case, too, the same effects as by the above mentioned diaper can be obtained.

In the diaper 101A of the present embodiment, the topsheet 102 extends from both side edges of the absorbent member 104, and the extensions are folded to the garment facing side of the absorbent member 104 and fixed to the backsheet 103 via an adhesive (not shown), etc. on the garment facing side of the absorbent member.

The disposable diaper 101A according to the present embodiment provides markedly improved protection against side leakage. This allows for reducing the width of the absorbent assembly or the width of the crotch section to provide a better fit while retaining the improvement of anti-leakage performance or minimizing reduction of anti-leakage performance. In this case, the pair of anti-leakage cuffs 106 rise upright to the wearer's skin to secure a sufficient height and is, if collapsed, less likely to narrow the effective area of absorption, so that the above effect is further ensured.

As compared with an absorbent member having continuous fibers, the absorbent member having staple fibers in the second absorbent core raises its side portions more easily with no tightening of fibers as well as exhibiting downward wicking properties in its middle region. The protection against side leakage is thus further enhanced. It is therefore preferred that the staple fibers or the particles used to produce the staple fibers be localized in the laterally middle region of the second absorbent core.

Although the third aspect of the present invention have been described with reference to its preferred embodiments, it is not limited to the foregoing embodiments. For instance, while in the foregoing embodiments the continuous fibers and the staple fibers are localized in different sites in the planar or thickness direction of the absorbent member, they may be present in a mixed state in a single web.

While in the foregoing embodiments the orientation direction of the continuous fibers and the staple fibers is coincident with the longitudinal direction of the absorbent member, the orientation direction of these fibers is not limited thereto and may be, for example, intersecting with the longitudinal direction of the absorbent member. Specifically, the continuous and the staple fibers may be oriented in the direction perpendicular to the longitudinal direction of the absorbent member.

While in the foregoing embodiments the orientation direction of the continuous fibers and that of the staple fibers are the same, these two kinds of the fibers may have different orientation directions. For example, the staple fibers may be oriented in the longitudinal direction of the absorbent member, whereas the orientation direction of the continuous fibers may be perpendicular to that direction. Conversely, the continuous fibers may be oriented in the longitudinal direction of the absorbent member, whereas the staple fibers may be oriented in the direction perpendicular to the longitudinal direction of the absorbent member.

The absorbent article of the present invention may have the above-described absorbent member 104 replaced with any of the aforementioned other absorbent members. The absorbent article of the invention may be an open type diaper with fasteners as well as a pull-on diaper. The absorbent member according to the invention may be used as a sublayer to be interposed between an absorbent pad and a topsheet of a conventional common disposable diaper.

The absorbent article of the invention having the absorbent member according to any of the foregoing preferred embodiments may have two or more pairs of opposing gathers. Examples of the absorbent article having such a configuration and the effects produced thereby as well as preferred configurations thereof are as described above with reference to FIGS. 10 and 11.

Still another preferred embodiment of the present invention will be described.

Figure 37:
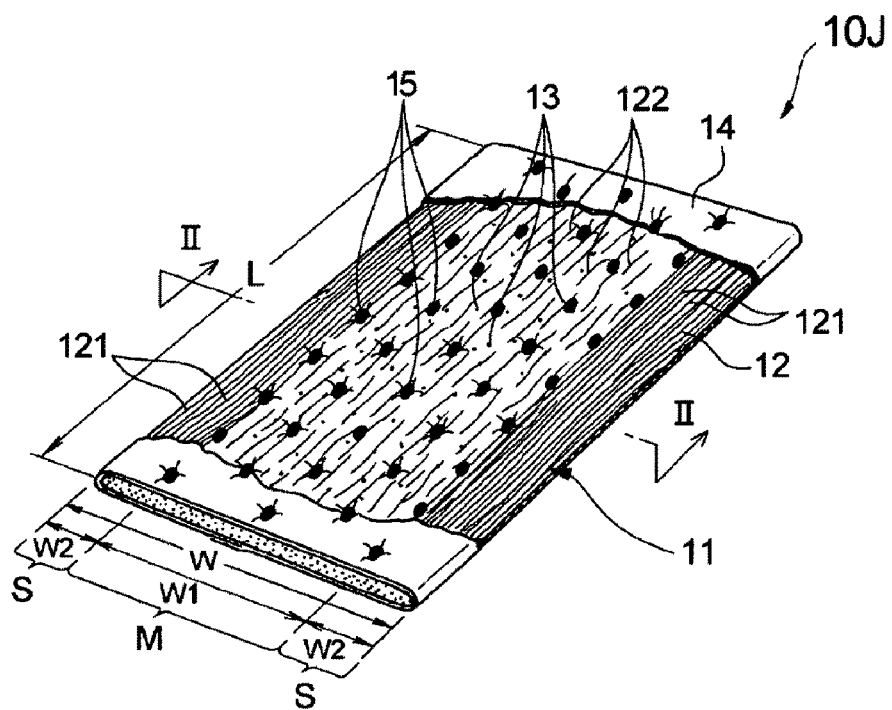
FIG. 37 is a perspective of one embodiment of the absorbent member according to the invention, with part cut away.
Figure 38:
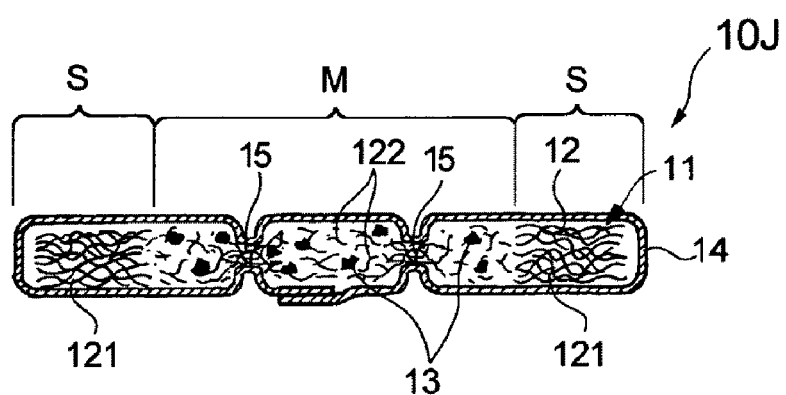
FIG. 38 is a schematic cross-section of the absorbent member of FIG. 37, taken along line II-II.

As illustrated in FIGS. 37 and 38, an absorbent member 10J according to a preferred embodiment of the invention includes an absorbent core 11 and a wrap sheet 14 wrapping the absorbent core 11. The absorbent core 11 is composed of a fiber aggregate 12 and lumpy particles of an absorbent polymer 13 held in the fiber aggregate 12. The fiber aggregate 12 contains staple fibers 122 bonded to one another and continuous fibers 121. The fiber aggregate 12 may be a nonwoven fabric. A nonwoven fabric is a fiber aggregate with strength as a whole. A nonwoven fabric may be folded to give a largely varied structure as an absorbent member.

As illustrated in FIGS. 37 and 38, the absorbent member 10J has the staple fibers 122 bonded to one another by heat embossing and therefore has a great number of bonds 15.

An absorbent member particularly of a thin type and a product containing the same are liable to bunch with the wearer's motion. In some cases, depending on the wearer's motion, an absorbent member can be destroyed, resulting in extremely reduced absorption capacity in part. Destruction of an absorbent member tends to cause leakage because it mostly takes place in a portion around the wearer's crotch where a body waste gathers easily and an outer force is imposed easily. In order to increase the absorbent member strength and to prevent reduction of leakage resistance and bunching, it is preferred that the staple fibers be bonded to one another as in the absorbent member 10J of the present embodiment and absorbent members 10B' to 10F' described later. It is more preferred that the staple fibers bonded to one another are present in a region that is to face a wearer's point of discharge (target region).

Bonds of the staple fibers can be formed, e.g., by heat embossing, ultrasonic embossing, or high frequency embossing. In the case of heat embossing, ultrasonic embossing, or high frequency embossing, the fibers at the bonds are fused to one another. The embossing processing may be used in combination with a hot-melt or low-melting thermoplastic resin, a binder such as an acrylic emulsion or a vinyl acetate emulsion, or a water soluble binder such as sodium carboxymethyl cellulose or polyvinyl alcohol.

The bonds 15 are discretely distributed in planar directions, i.e., the longitudinal and the lateral directions, of the absorbent member 10J (2 portions). Specifically, the bonds 15 are equally spaced in the longitudinal direction of the absorbent member 10J (2 portions) to form a number of lines of bonds extending along the longitudinal direction, and the lines of bonds are equally spaced in the lateral direction of the absorbent member. The positions of the bonds in one of the lines and those in adjacent lines are out of alignment by half the pitch of the bonds in one line. In short, the bonds 15 are arranged in a staggered pattern.

Each of the bonds 15 is a result of pressing the fiber aggregate 12 in the thickness direction under heat to fuse a plurality of the staple fibers 122.

When the bonds 15 are regular patterns such as dots or lines, the area of the individual bonds 15 is preferably 0.1 to 1.2 cm$^2$, more preferably 0.07 to 0.8 cm$^2$, in view of maintaining the downward wicking properties and improving the strength. The number of bonds 15 per 2 cm$^2$ is preferably 1 to 9, more preferably 1 to 4. The bonds may be arranged to provide an aesthetic pattern such as animals or flowers.

The area of the individual bonds 15 does not need to be constant all over the absorbent article. In the case of providing an aesthetic design, the area can be varied as appropriate to the absorbency and other purposes.

The continuous fibers 121 and the staple fibers 122 are localized in different sites in the plane of the absorbent member 10J. Specifically, the staple fibers 122 are localized in a region M of the absorbent member 10J. The region M has a prescribed width and is located in the laterally middle portion of the absorbent member 10J (hereinafter also referred to as a middle region M). The staple fibers 122 are distributed substantially evenly in the middle region M and is substantially absent in the parts located in side regions S outboard of the middle region M. The continuous fibers 121 are localized in the side regions S, being distributed there substantially evenly. In the middle region M are there only a small amount of continuous fibers compared with the side regions S.

In the middle region M of the absorbent member 10J, there are not only staple fibers of continuous fiber origin but continuous fibers remaining non-cut. That is, continuous fibers and staple fibers are present in a mixed state in the middle region M. The phrase "in a mixed state" as used herein does not include a state in which a layer made of staple fibers and a layer made of continuous fibers are superposed on each other such that several staple fibers of the former layer have part thereof in their longitudinal direction enter the latter layer. The mixed state of the continuous fibers and the staple fibers is preferably such that the staple fibers have part thereof in their longitudinal direction entangled with the continuous fibers.

In the absorbent member 10J of the present embodiment, the staple fibers in the bonds 15 are fused not only to one another but also to the continuous fibers.

While the bonds 15 in the present embodiment are formed in only the middle region M of the absorbent member 10J, the side regions S may also be processed in the same manner to form bonds in which the continuous fibers are fusion bonded to one another. For example, the side regions S may be heat embossed to form bonds in the same pattern as in the middle region M.

Other methods of enhancing the downward wicking properties and improving web shape retention include a method in which a sheet or a plurality of sheets made of paper, nonwoven fabric, etc. may be superposed or wrapped around the upper and/or lower side of the web and/or the side portions of the web and joined to the web with an adhesive that has previously been applied to the sheet side or by heat fusion. By this method, an absorbent member of sheet form is obtained, in which the web is held in between a pair of sheets. Such an absorbent member of sheet form has increased stiffness due to the joint with the sheets and the stiffness of the sheets per se and therefore exhibits improved handling properties and can easily be transported alone. Furthermore, the absorbent member of sheet form can easily be trimmed or punched into any desired contour in conformity to the contour of an absorbent article.

When the sheet and the web are joined with an adhesive to increase the web shape retention, the adhesive is preferably applied so as not to impair water permeability, softness, and breathability of the web. It is advantageous for this that the adhesive be applied in as fine a line as possible in a discontinuous pattern such as an array of spirals, separate lines, or "omega" shaped lines. Fibers can thus be bonded at a number of joints without ruining the characteristics of the web. This can be achieved by using, for example, UFD Fiber (trade name), a kind of hot melt adhesive applicator. Any type of adhesives, either hydrophilic or hydrophobic, may be used with no limitation. A hydrophilic adhesive is preferred. A useful hydrophilic adhesive is exemplified by Cycloflex (registered trade name of a hydrophilic hot melt adhesive from National Starch & Chemical Corp., Delaware, U.S.A.).

Although the adhesion between the sheet and the web is between the surfaces of the two adherents, the term "adhesion" as used here includes incidental adhesion between fibers in the thickness direction of the web because the adhesive may penetrate into the web.

To superpose the sheet on the upper side and/or the lower side of the web is advantageous to enhance the absorbing performance of the absorbent member. To increase the absorbing performance of the absorbent member, it is preferred to use a fiber sheet or a fiber web as the sheet. Examples of such a sheet material include air-through nonwovens, airlaid nonwovens, dry processed pulp nonwovens, crosslinked pulp, paper containing crosslinked pulp, and composites of the sheet materials recited. These sheets may be used singly, or a plurality of the sheets may be used as a stack. The fibers making up the sheet preferably have a fineness of 1.7 to 12 dtex, more preferably 2.2 to 7.8 dtex, even more preferably 3.3 to 5.6 dtex. The sheet preferably has a basis weight of 15 to 200 g/m$^2$, more preferably 20 to 150 g/m$^2$, even more preferably 25 to 120 g/m$^2$. When it is demanded to improve the rate of fluid acquisition, to prevent rewet, or to facilitate fluid diffusion in the sheet, it is preferred to use a sheet having a basis weight of 15 to 100 g/m$^2$, more preferably 20 to 80 g/m$^2$, even more preferably 25 to 50 g/m$^2$. When it is demanded to improve the cushioning properties of the absorbent member, to prevent the absorbent member from bunching up, to impart recovery from compression to the absorbent member, or to suppress dissipation of water vapor from the absorbent member, it is preferred to use a sheet having a basis weight of 25 to 200 g/m$^2$, more preferably 30 to 150 g/m$^2$, even more preferably 40 to 120 g/m$^2$.

The absorbent member 10J of the present embodiment is assembled into an absorbent article such as a disposable diaper or a sanitary napkin with its middle region M (where the staple fibers have been created) located in the target zone P that is adapted to face a point of body fluid discharge of a wearer as illustrated in FIG. 3. In this mode of application, a body fluid discharged from the point of discharge (e.g., urine or menstrual blood) is smoothly drawn into the inside of the absorbent member 10J within a small planar area owing to the excellent downward wicking properties of the staple fibers. The fluid acquired into the absorbent member 10J is absorbed by the absorbent polymer 13 localized in the zone and thus stably retained in the absorbent member 10J.

When the absorbent member 10J receives a considerable quantity of a fluid in a short time or acquires large quantities of a fluid after long time use, the fluid can spread to the side regions S. Since there are continuous fibers in the side regions S, remaining non-cut and oriented in the longitudinal direction of the absorbent member, the fluid having reached the side regions S well diffuses in the longitudinal direction of the absorbent member 10J (the front-to-rear direction of a wearer), while being suppressed from diffusing across the side regions S. As a result, leakage from both side edges of the absorbent member 10J is prevented effectively, and a large area of the absorbent member can be made effective use of.

Furthermore, since the absorbent member 10J has the bonds 15 formed by bonding the staple fibers 122 to one another, the fiber aggregate 12 itself and the absorbent member 10J containing the same exhibit superior strength in the middle region M where the staple fibers are localized and are less liable to reduce the anti-leakage properties and to bunch up. That is, even with a force such as compressive force or a bending force is imposed to the absorbent member 10J by the wearer's motion, the force is dispersed by the staple fibers 122 via the bonds 15 so that the fiber aggregate 12 and the absorbent member 10J containing the same are less liable to break or move to either side. As a result, the lumpy absorbent polymer particles 13 are less likely to be moved to either side and to reduce the anti-leakage properties.

Since the bonds 15 are formed of heat fusion of not only staple fibers but continuous fibers in the present embodiment, the force imposed to the absorbent member 10J is dispersed over a wider area to bring about enhancement of the effects described.

Since the bonds 15 provide depressions on the surface of the absorbent member 10J, a fluid is made to flow easily into the depressions, which further improves the downward wicking properties.

Both the absorbent polymer 13 and the staple fibers 122 of continuous fiber origin are present in the middle region M of the absorbent member 10J of the present embodiment. The area where the absorbent polymer particles 13 are present and the area where the staple fibers 122 are created coincide with each other.

To prevent side leakage from the absorbent member incorporated in an absorbent article, the width W1 (see FIG. 37) of the region in which the staple fiber 122 have been created (equal to the width of the middle region M) along the width direction of the absorbent member 10J is preferably 20% to 95%, more preferably 50% to 85%, of the total width W (see FIG. 37) of the absorbent member 10J, and the total of widths W2 (see FIG. 37) of the regions in which the staple fibers are substantially absent (equal to the total width of the side regions S) is preferably 5% to 80%, more preferably 15% to 50%, of the total width W of the absorbent member 10J.

FIGS. 39 through 43 illustrate the absorbent members according to yet other embodiments of the present invention. The absorbent members 10B' to 10F' illustrated in FIGS. 39 through 43 each contain staple fibers in the hatched area.

Figure 39A:
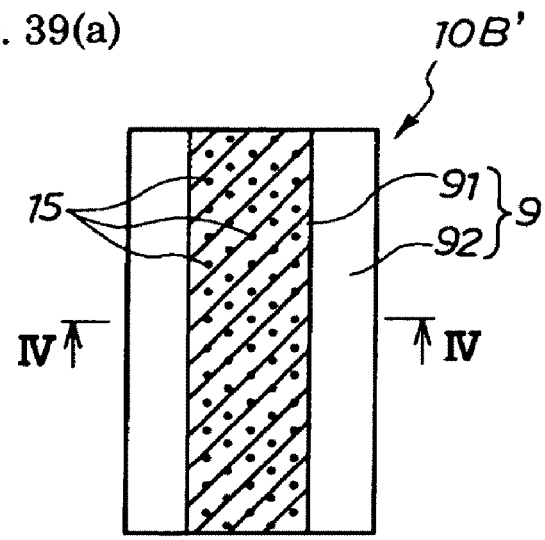
Figure 39B:
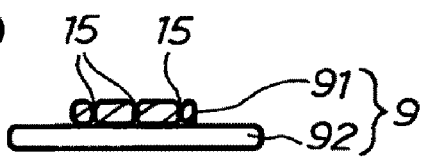

The absorbent member 10B' illustrated in FIGS. 39(a) and 39(b) is composed of an absorbent core 9 and a wrap sheet (not shown) wrapping the absorbent core 9. The absorbent core 9 is a dual layered fiber aggregate composed of an upper fiber layer 91 made mainly of staple fibers and a lower fiber layer 92 made mainly of continuous fibers. The wrap sheet covers the upper and lower sides and both side edge faces of the absorbent core 9 in the same manner as in the absorbent member 10J shown in FIGS. 37 and 38.

The staple fibers in the absorbent member 10B' are localized in the upper fiber layer 91 that is adapted to face the skin of a wearer as assembled into an absorbent article, while the continuous fibers are localized in the lower fiber layer 92 that is adapted to face the opposite side to the skin facing side. The continuous fibers and the staple fibers are localized in different positions in the thickness direction of the absorbent member.

In the present embodiment, the upper fiber layer 91 of the absorbent member 10B' has bonds 15 resulting from heat embossing, in each of which the staple fibers are fusion bonded to one another.

The absorbent member 10B' exhibits excellent downward wicking properties in its upper fiber layer 91 containing the staple fibers. Therefore, an absorbent article such as a disposable diaper or a sanitary napkin having the absorbent member 10B' incorporated therein with the upper fiber layer 91 facing a point of discharge of a wearer is able to smoothly wick a body fluid (e.g., urine or menstrual blood) discharged from a point of discharge through a small area of the absorbent member. When a considerable quantity of a fluid supplied to or acquired by the absorbent member reaches the lateral side portions of the absorbent member or the garment-facing surface of the upper fiber layer 91, the fluid well spreads in the longitudinal direction of the absorbent member (the front-to-rear direction of a wearer) along the continuous fibers oriented in the longitudinal direction of the absorbent member. As a result, a large area of the absorbent member can be made effective use of, while diffusion of the fluid in the lateral direction of the absorbent member is suppressed to provide excellent protection against side leakage.

While in the absorbent member 10B' the upper fiber layer 91 is narrower than the lower fiber layer 92, the upper fiber layer 91 and the lower fiber layer 92 may have substantially the same width. The length of the upper fiber layer 91 in the longitudinal direction, which is depicted as being equal to that of the lower fiber layer 92, may be smaller than that of the lower fiber layer 92.

Each of the absorbent members 10C' to 10F' shown in FIGS. 40 through 43 includes an absorbent core 9 formed of a single layered fiber aggregate 93 and a wrap sheet (not shown) wrapping the absorbent core 9. The wrap sheet covers the upper and lower sides of the absorbent core 9. The wrap sheet preferably covers the upper and lower sides of at least a region 9S of the absorbent core 9 where staple fibers are localized.

Each of the absorbent members 10C' to 10F' has staple fibers localized in the hatched region and continuous fibers localized in the non-hatched region. In other words, the continuous fibers and the staple fibers are localized in different sites in the plane of these absorbent members. All the absorbent members 10C' to 10F' have bonds 15 and 15A in which fibers are bonded to one another as a result of heat embossing the fiber aggregate 93 as wrapped in the wrap sheet. The bonds 15 and 15A are discretely dispersed over substantially the entire area of the respective absorbent members. In the bonds 15 located in the hatched region, the staple fibers are fusion bonded to one another. In the bonds 15A located in the non-hatched region, the continuous fibers are fusion bonded to one another.

Figure 40A:
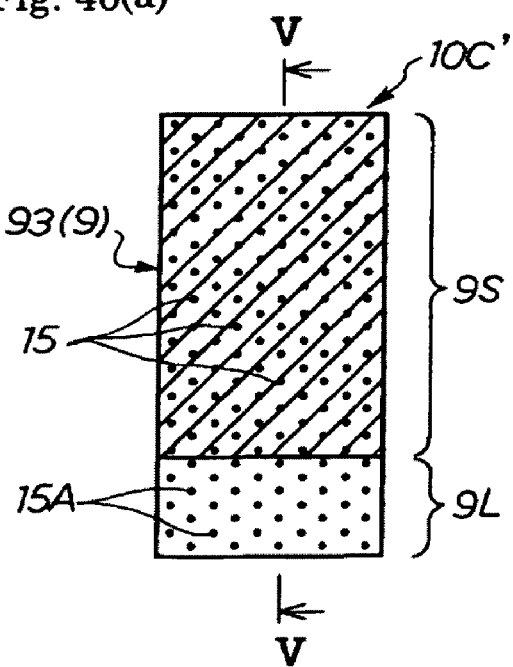
FIG. 40(*a*) and FIG. 40(*b*) are each a view of still another embodiment of the absorbent member according to the invention, of which FIG. 40(*a*) is a plan, and FIG. 40(*b*) is a cross-section along line V-V in FIG. 40(*a*).
Figure 40B:
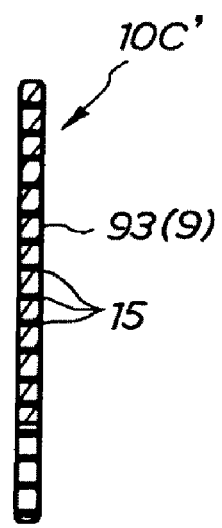

The absorbent member 10C' illustrated in FIGS. 40(a) and 40(b) has an absorbent core 9 formed of a fiber aggregate 93. The absorbent core 9 (fiber aggregate 93) has a region 9S where staple fibers are localized as one of opposite longitudinal end portions and a region 9L where continuous fibers are localized as the other end portion. When the absorbent member 10C' is assembled in a diaper with its region 9S having the staple fibers straddling the crotch section and the stomach section of the diaper and its region 9L having the continuous fibers disposed in the back section of the diaper, the diaper exhibits excellent downward wicking properties in its crotch section and provides effective protection against leakage from the front end. In contrast, when the absorbent member 10C' is assembled the other way around, leakage from the rear end is prevented effectively.

Figure 41A:
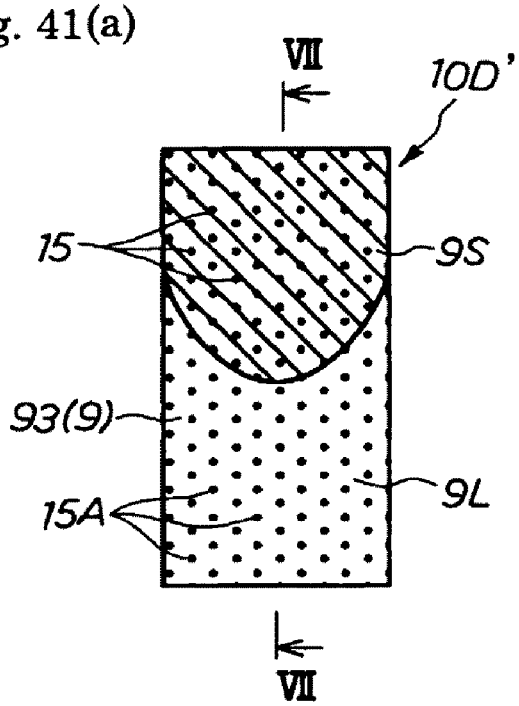
FIG. 41(*a*) and FIG. 41(*b*) are each a view of still another embodiment of the absorbent member according to the invention, of which FIG. 41(*a*) is a plan, and FIG. 41(*b*) is a cross-section along line VII-VII in FIG. 41(*a*).
Figure 41B:
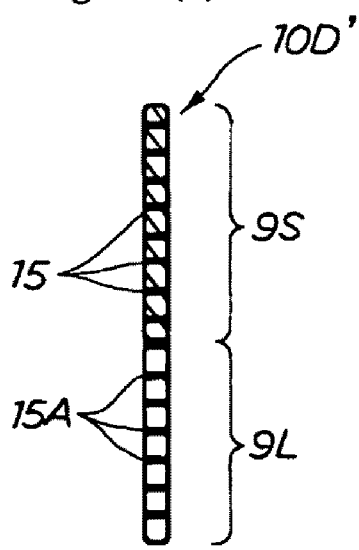

The absorbent member 10D' illustrated in FIGS. 41(a) and 41(b) has an absorbent core 9 formed of a fiber aggregate 93. The absorbent core 9 has a horseshoe-shaped region 9S where staple fibers are localized in one of the opposite longitudinal end portions and a region 9L where continuous fibers are localized in the other end portion. An absorbent polymer is localized in the region 9L. When the absorbent member 10D' is incorporated in a diaper with its region 9L located to face the back of a wearer, the diaper exhibits excellent downward wicking properties in its stomach side, and makes urine spread effectively and makes as much absorbent polymer as possible retain urine thereby to prevent leakage effectively even when a wearer lying on its back discharges a large amount of urine during sleep. The stomach side of the absorbent member swells preferentially to make a thickness difference, which serves to prevent a body waste (e.g., loose stool) from flowing from the back to the front of the wearer.

Figure 42A:
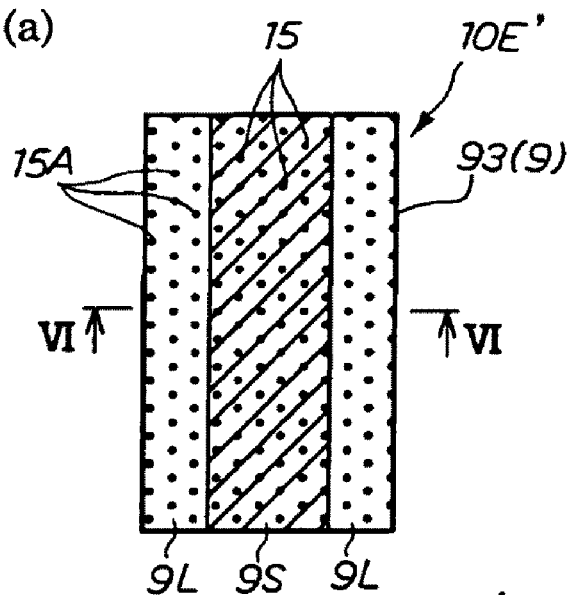
FIG. 42(*a*) and FIG. 42(*b*) are each a view of still another embodiment of the absorbent member according to the invention, of which FIG. 42(*a*) is a plan, and FIG. 42(*b*) is a cross-section along line VI-VI in FIG. 42(*a*).
Figure 42B:
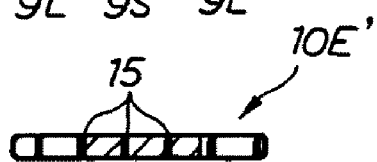

The absorbent member 10E' illustrated in FIGS. 42(a) and 42(b) has an absorbent core 9 formed of a fiber aggregate 93. The absorbent core 9 has a region 9S where staple fibers are localized in its laterally middle portion and a region 9L where continuous fibers are localized on each lateral side of the region 9S.

The configuration of the absorbent member 10E' produces the same effects as by the absorbent member 10J of FIGS. 37 and 38. When incorporated into a diaper with its longitudinal direction coinciding with the front-to-rear direction of the diaper, the absorbent member 10E' easily raises both of its side portions toward the skin of a wearer with the aid of elastic members disposed in or in the vicinity of the side portions thereby to form barriers against side leakage. The elastic member for raising the side portions of the absorbent member 10E' may be disposed, e.g., on the skin-facing side or the garment-facing side of the absorbent member 10E', near both the side edges of the absorbent member 10E', or inside the absorbent member 10E'.

Figure 43A:
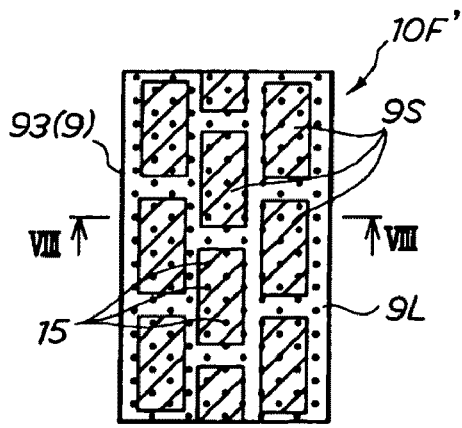
FIG. 43(*a*) and FIG. 43(*b*) are each a view of still another embodiment of the absorbent member according to the invention, of which FIG. 43(*a*) is a plan, and FIG. 43(*b*) is a cross-section along line VIII-VIII in FIG. 43(*a*).
Figure 43B:
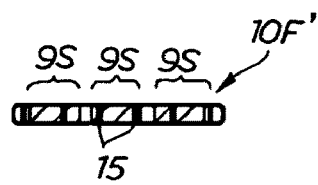

The absorbent member 10F' in FIGS. 43(a) and 43(b) has an absorbent core 9 formed of a fiber aggregate 93. The absorbent core 9 has regions 9S containing staple fibers discretely arranged therein. A plurality of the staple-containing regions 9S, being discretely arranged in either a random or a regular pattern, quickly absorb a fluid, swell, and bulge out. The bulges thus formed serve to maintain ventilation between the skin and the diaper even after the swelling. In addition, the bulges reduce the contact area between the skin and the diaper, which reduces burden to the skin, e.g., scratching.

The staple fibers used in all the absorbent members 10B' to 10F' are preferably synthetic or semisynthetic fibers. Although conventional absorbent members commonly use pulp fiber, an absorbent member using staple fibers that are not of pulp origin maintains its bulkiness to continue providing an environment allowing for the absorbent polymer to swell because such staple fibers are less absorptive per se and therefore resistant to collapse.

Examples of the synthetic fibers that can be used as staple fibers include polyolefins typified by polyethylene and polypropylene, polyesters typified by polyethylene terephthalate, polyacrylonitrile fibers typified by acrylic fiber, polyamides typified by nylon, polyvinyl alcohol typified by vinylon, and polyurethane. Examples of semisynthetic fibers that can be used as staple fibers include rayon, cuprammonium, and cellulose acetates. The synthetic or semisynthetic fibers recited above can be used either individually or as a combination of two or more thereof. The term "synthetic or semisynthetic" as used herein is intended to include a combination of synthetic fibers and semisynthetic fibers.

The staple fibers used in the invention may be pulp fibers. Where the staple fibers are pulp fibers, pulp fibers having a low degree of beating are used, and the bonds in which pulp fibers are bonded to one another may be formed by embossing, hydroentanglement, or chemical reaction.

The staple fibers contained in the absorbent members 10B' to 10F' are not those created by cutting continuous fibers using lumpy particles.

The upper fiber layer 91 of the absorbent member 10B' shown in FIGS. 39(a) and 39(b) can be formed of a carded web (a web prepared using a carding machine), a granted web (a web prepared using a garnet machine), an air-laid web (a web formed by using an air stream), or the like. The fibers constituting a carded web have the form of staple before being carded.

The lower fiber layer 92 of the absorbent member 10B' can be formed of a web prepared by opening a tow in the same manner as for the aforementioned absorbent members. The lower fiber layer 92 may also be formed of a web prepared by spun bonding (a molten resin is directly spun into filaments). The web may be subjected to a hydrophilization treatment or a processing for crimping.

Figure 44A:
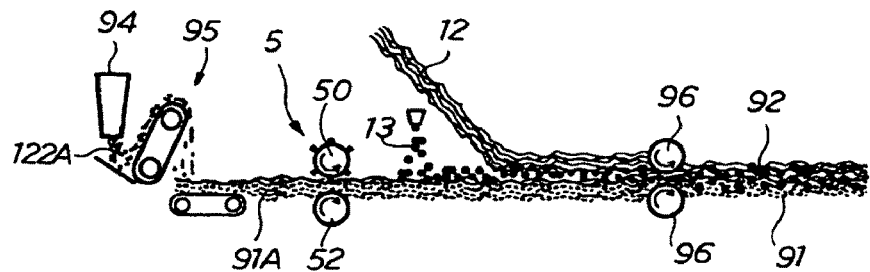
FIG. 44(*a*) illustrates still another example of the method of producing the absorbent member according to the invention, and FIG. 44(*b*) illustrates yet another example of the method of producing the absorbent member according to the invention.

FIG. 44(a) illustrates an example of a method of making the absorbent member 10B'.

In the method illustrated in FIG. 44(a), staple fibers 122A metered from hopper 94 are fed to carding machine 95, where the staple fibers 122A are carded into a continuous-form web 91A. The web 91A is introduced into the nip of an embossing roller 50 and an anvil roller 51 to be heat embossed to form bonds 15 in which the staple fibers 122A are bonded to one another. Non-lumpy absorbent polymer particles 13 are spread on the web 91A having the bonds 15, and a tow-opened, continuous fiber web 12 is superposed on the polymer-spread side of the web 91A. The resulting laminate is passed between a pair of rollers 96 and pressed in its thickness direction. The pressing between the rollers 96 should be conducted under such conditions as to reduce the thickness of the laminate to impart shape retention without causing substantial cutting of the continuous fibers. After being pressed between the rollers 96, the laminate is wrapped in a wrap sheet fed from a wrap sheet feeding mechanism (not shown). The wrapped laminate of continuous form is then cut to length to obtain individual absorbent members 10B' in a continuous manner.

In the method described, the absorbent polymer 13 is distributed between the carded web 91A and the continuous fiber web 12. The resulting absorbent member 10B' has the absorbent polymer localized on and near the interface between the upper fiber layer 91 and the lower fiber layer 92 in the thickness direction.

Figure 44B:
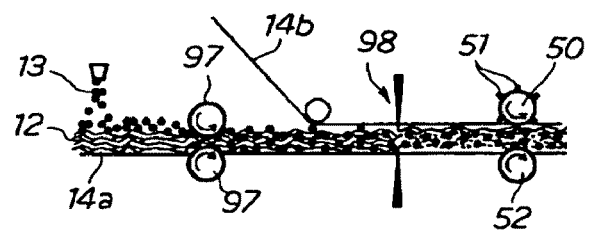

FIG. 44(b) represents an example of a method of producing the absorbent member 10C' to 10F'. In the method illustrated in FIG. 44(b), a tow-opened, continuous fiber web 12 is continuously transported as supported by an extensible sheet 14a. Non-lumpy particles of an absorbent polymer 13 are spread on the web 12. The web 12 having the absorbent polymer 13 spread thereon is passed between a pair of rollers 97 to press the polymer particles 13 into the web 12. An extensible sheet 14b is superposed on the opposite side of the web 12 to the polymer-spread side (on the side opposite to the sheet 14a), and the web 12 as sandwiched in between the sheets 14a and 14b is passed through a continuous fiber cutting unit 98 to cut the continuous fibers in part of the web 12. The web is then heat embossed between an embossing roller 50 and an anvil roller 52 to form bonds 15 in which the staple fibers are bonded to one another. The web is then cut to the length of individual absorbent members by means of a cutting mechanism (not shown).

The continuous fiber cutting unit 98 is designed to cut continuous fibers regardless of the presence or absence of lumpy particles. Such a cutting unit is exemplified by a unit including a pressing member with cutting projections on its peripheral surface or on one side thereof. The pressing member is configured to press the web 12 sandwiched between the sheets 14a and 14b to cut the continuous fibers by the cutting projections thereof. The continuous fiber cutting unit 98 is preferably designed not to cause the cutting projections to make a hole through the extensible sheets 14a and 14b.

Figure 45:
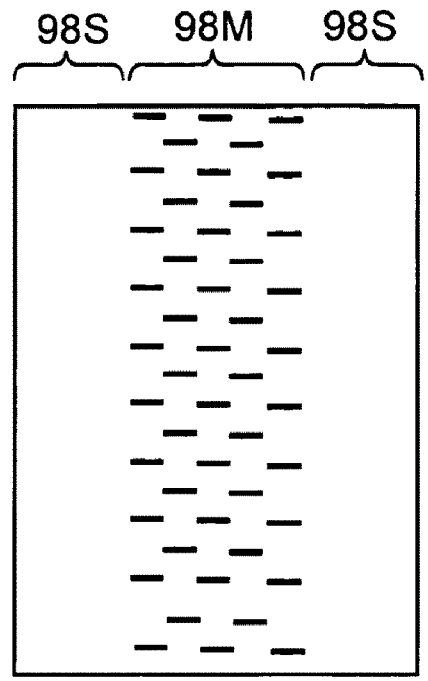
FIG. 45 is a developed plan of the pressing roller used in the method illustrated in FIG. 44(*b*), representing an example of arrangement of cutting projections.

In FIG. 45 is illustrated an example of arrangement of the cutting projections of the cutting unit 98 that can be used to make the absorbent member 10E'. FIG. 45 is a development view of a pressing roller, showing the pattern of arrangement of the cutting projections on the peripheral surface (the surface of a pressing member). As illustrated in FIG. 45, the pressing roller has cutting projections arranged in a staggered pattern in a portion 98M that corresponds to the laterally middle portion of the web 12. Pressing the web 12 against the portion 98M results in formation of a great number of staple fibers in the middle region of the web 12. Because the cutting projections are not provided in portions 98S that correspond to both the side portions of the web 12, substantially no staple fibers are created in the side portions of the web 12. The absorbent members 10C', 10D', and 10F' can be produced in the same manner except for altering the pattern of arranging the cutting projections on the surface of the pressing member.

In still other embodiments of the absorbent member according to the present invention, there are provided absorbent members having any of the configurations shown in FIGS. 40 through 43 in which the staple fibers in the respective hatched regions are of continuous fiber origin. These absorbent members are produced by altering the pattern for spreading lumpy particles that are able to cut the continuous fibers.

Figure 46:
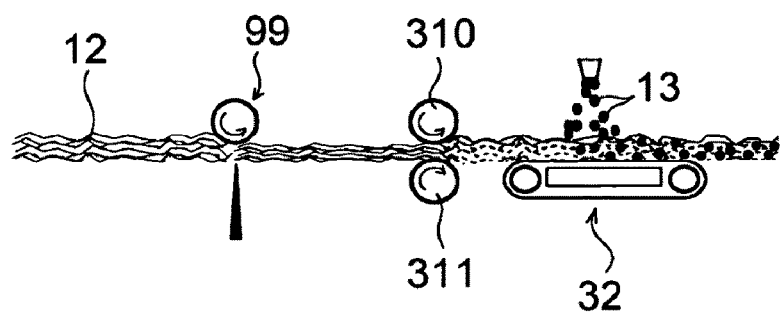
FIG. 46 illustrates a method of producing another embodiment of the absorbent member according to the invention.

FIG. 46 illustrates a method of producing still another embodiment of the absorbent member according to the present invention. In the method of FIG. 46, a tow-opened continuous fiber web 12 is fed to a continuous fiber cutting unit 99, where the continuous fibers are cut in part to create stable fibers of continuous fiber origin in part. The web 12 containing the staple fibers and the continuous fibers remaining non-cut is then stretched by drawing it by a pair of rollers 310 and 311. The stretched state of the web is relaxed between the pair of rollers 310 and 311 and a vacuum conveyor 32, and an absorbent polymer 13 is fed to the web in the relaxed state while being sucked by the vacuum conveyor 32 from the opposite side of the web. The web having the absorbent polymer is wrapped in a wrap sheet fed from a wrap sheet feeding mechanism (not shown), passed through a heat embossing unit (not shown) to form bonds, and cut to the length of individual absorbent members.

The above-described method produces an absorbent member formed of a fiber aggregate containing both the continuous fibers and the staple fibers of continuous fiber origin in a mixed state. In the bonds, the staple fibers are bonded not only to one another but to the continuous fibers.

In the case where nonwoven fabric is used to form a fiber aggregate in the present invention, the fiber aggregate may be totally formed of nonwoven fabric or may be formed of a combination of nonwoven fabric and a fiber layer that is not nonwoven fabric. It is preferred to use a combination of a nonwoven fabric made mainly of staple fibers and a fiber layer that is not nonwoven fabric and is made mainly of continuous fibers in view of polymer supporting properties (i.e., possibility of reducing the absorbent member thickness), absorbent member strength, liquid spreading properties, and the like.

Figure 47:
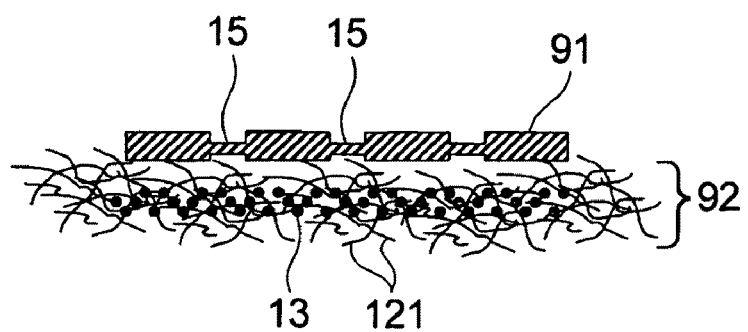
FIG. 47 is a cross-section showing still another embodiment of the absorbent member according to the invention.

FIG. 47 represents an example in which a nonwoven fabric made of staple fibers (upper fiber layer) 91 is superposed on the skin facing side of the lower fiber layer 92 made of continuous fibers 121. The staple fibers are consolidated by fusion bonding and embossed to form debosses 15 where the fibers are densified to exhibit improved wicking properties.

Figure 48:
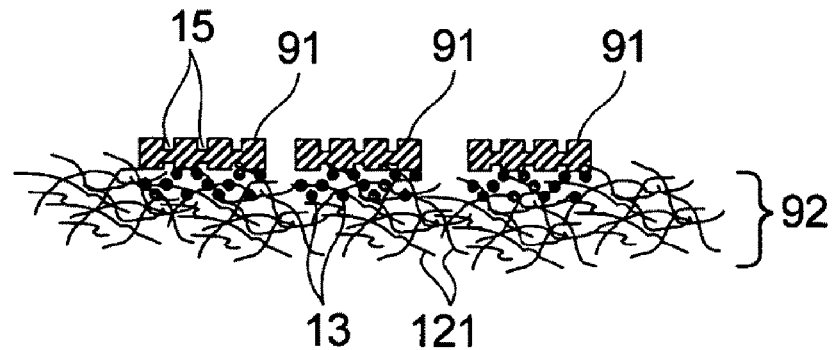
FIG. 48 is a cross-section of still another embodiment of the absorbent member according to the invention.

FIG. 48 is another example in which the nonwoven fabric (upper fiber layer) 91 in FIG. 47 is replaced with nonwoven fabric strips 91. An absorbent polymer 13 in the lower fiber layer 92 made of continuous fibers 121 is mostly distributed in the regions on which the nonwoven fabric strips 91 are superposed.

The lower fiber layer 92 in each of FIGS. 47 and 48 is a fiber web that is not consolidated into nonwoven fabric. The horizontal direction in FIGS. 47 and 48 is perpendicular to the continuous fiber orientation direction, i.e., the longitudinal direction of the fiber aggregate. Both the embodiments shown in FIGS. 47 and 48 are expected to exhibit downward wicking properties in the region(s) having the staple fibers and liquid spreading properties in the part having the continuous fibers. As a result, the whole absorbent member can be made efficient use of, and the staple fibers are effective in keeping a fluid away from the skin of a wearer. The staple fibers, being in a consolidated form, provides the absorbent member with increased strength resistant to bunching or destruction.

In the present invention, bonding between staple fibers can be carried out by other means than by heat embossing, ultrasonic embossing or high frequency embossing described. Such other means include a through-air bonding process in which hot air is blown through a fiber aggregate containing staple fibers to bond the staple fibers to one another by fusion. Specifically, the embossing unit 5 used in the method illustrated in FIG. 44 may be displaced with a through-air bonding unit where the staple fibers are fusion bonded to one another by hot air. The staple fibers may also be bonded to one another using a hot-melt or low-melting thermoplastic resin or a binder of various kinds.

The absorbent member according to the invention is preferably used as an absorbent member of an absorbent article such as a disposable diaper, as disposed between a liquid impermeable topsheet and a leakproof (liquid permeable or water repellent) backsheet and. The absorbent member of the invention may also be used as a sublayer interposed between an absorbent member having a common structure used in conventional disposable diapers, etc, and a topsheet.

Figure 49:
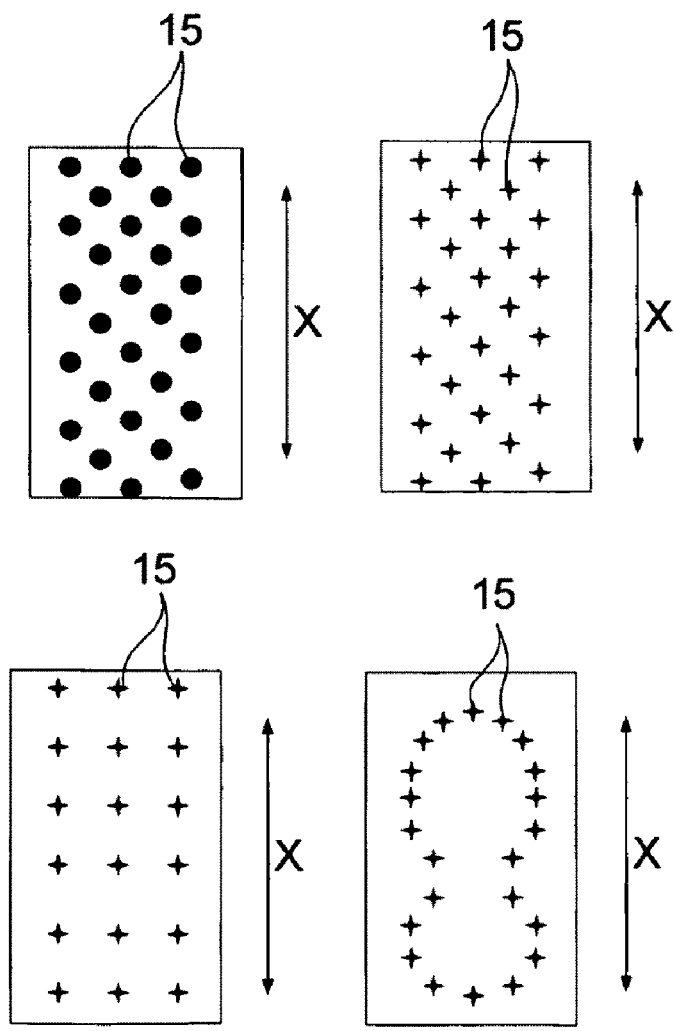
FIG. 49 presents plans of absorbent members showing examples of arrangement of bonds.

The planar shape of the individual bonds formed by embossing can be of arbitrary design, such as circle, elongated circle, square, rectangle, triangle, and star. The arrangement of the bonds is not limited to the staggered pattern as described and may be those illustrated in FIG. 49, in which examples of the planar shape of individual bonds and their arrangement are shown. Direction X in FIG. 49 is the continuous fiber orientation direction.

In the description given above, particulars of a certain embodiment that have been omitted to avoid redundancy can appropriately be complemented by the corresponding description of other embodiments. Particulars described as being characteristic of a certain embodiment can apply to other embodiments appropriately. Particulars of every embodiment are appropriately interchangeable between embodiments.

The present invention will now be illustrated in greater detail with reference to Examples, but it should be understood that the invention is not construed as being limited thereto.

Example 1

A tow of crimped, continuous cellulose acetate fibers was prepared. The individual continuous fibers had a thickness of 2.1 dtex, and the total linear density of the tow was 25,000 dtex. The tow was fed under tension and opened in an air opening unit. The tow-opened web was passed between a roller having a large number of discs arrayed around its periphery in an axial direction at a given interval and a smooth anvil roller, between which the web was combed. The width of the web was adjusted to 100 mm. The running speed of the web was slowed down, and the web was transferred onto a vacuum conveyor. The web on the vacuum conveyor was released from the tension to develop the crimp. The continuous fibers of the web had a crimp percentage of 30%, and the number of the crimps per centimeter was 15. The fiber interstices in the web were thus broadened to help an absorbent polymer enter and to make the web bulkier thereby to improve polymer supporting capability. In this state, an absorbent polymer was spread on the web over a width of 80 mm and embeddedly supported therein. The basis weight of the web was 25 g/m$^2$, and the amount of the absorbent polymer spread was 132 g/m$^2$.

Separately, 100 parts by weight of opened fluff pulp and 100 parts by weight of an absorbent polymer were uniformly mixed in an air stream and accumulated on a T-shaped frame to obtain an airlaid fiber layer having a basis weight of 300 g/m$^2$. The T-shaped frame was made up of a vertical portion with a width of 100 mm and a length of 100 mm and a horizontal portion with a width of 100 mm and a length of 125 mm. The airlaid fiber layer contained 150 g/m$^2$ of the fluff pulp and 150 g/m$^2$ of the absorbent polymer. The web was superposed on the fiber layer, and the resulting laminate was wrapped in tissue paper having a basis weight of 16 g/m$^2$ on which a hot-melt adhesive had been sprayed. The wrapped laminate was compressed between a metal roller and a rubber roller having a clearance of 0 mm therebetween, whereby the constituting fibers of the web were cut by the absorbent polymer particles, and the web and the tissue paper were united to provide an absorbent member.

The web (the fiber aggregate or the continuous fiber web) contained lumpy absorbent polymer particles and staple fibers in a region generally as illustrated in FIG. 6(d). The staple fibers were localized in the 80 mm-wide laterally middle region of the absorbent member where the absorbent polymer had been spread. The proportion of the staple fibers in the laterally middle region of the web was 86% (the proportion of the continuous fibers in that region was 14%), whereas that in the side regions of the web was 18%.

Method of Measuring Fiber Distribution:

A hundred fibers were randomly drawn from the skin facing side of the longitudinally middle portion of the absorbent member, and their lengths were measured in accordance with the mean fiber length measurement method (method C) specified in JIS L1015. The data were plotted into a histogram. The proportion of the fibers shorter than 70 mm was calculated from the histogram to give the proportion of the staple fibers.

Example 2

A tow-opened web having an absorbent polymer embedded therein was prepared in the same manner as in Example 1, except that the polymer was spread intermittently. Specifically, the polymer was spread on a laterally middle portion of the web having a width of 80 mm and extending from a position 100 mm away from the front edge to a position 350 mm away from the front edge (over an area of 80 mm in the web width direction by 250 mm in the web length direction). Opened fluff pulp was airlaid in a frame having the same shape as that used in Example 1 to make an airlaid fiber layer having a basis weight of 100 g/m$^2$. The web was superposed on the airlaid fiber layer, and the laminate was wrapped in a hydrophilized spunbonded-meltblown-meltblown-spunbonded (SMMS) nonwoven fabric having a basis weight of 16 g/m$^2$. The wrapped laminate was compressed between a metal roller and a rubber roller in the same manner as in Example 1 to cut the fibers constituting the web.

The web (the fiber aggregate or the continuous fiber web) contained lumpy absorbent polymer particles and staple fibers in a region generally as illustrated in FIG. 6(a). The proportion of the staple fibers in the absorbent member in the region where the absorbent polymer had been spread was 78% (the proportion of the continuous fibers in that region was 22%), whereas that in the region where the polymer had not been spread was 12%.

Example 3

A web (designated web P1) having an absorbent polymer embedded therein was prepared in the same manner as in Example 1.

Bicomponent conjugate fibers having a polyethylene sheath and a polypropylene core (3.3 dtex, 51 mm, having been surface treated with a surface active agent to have hydrophilic properties and antistatic properties) were carded to make a web (designated web P2) having a basis weight of 30 g/m$^2$. The resulting web P2 made of synthetic fibers was superposed on the web P1 having the absorbent polymer embedded therein.

Separately, 100 parts by weight of fluff pulp and 100 parts by weight of an absorbent polymer were uniformly mixed in an air stream and accumulated within a T-shaped frame to make an airlaid fiber layer weighing 300 g/m$^2$ (the same as the one used in Example 1). The airlaid fiber layer was superposed on tissue paper having a basis weight of 16 g/m$^2$ and having a hot-melt adhesive previously sprayed thereto. The above prepared laminate of P1 and P2 was superposed thereon. On the resulting stack of fiber layers, was superposed another tissue paper having a basis weight of 16 g/m$^2$ and having a hot-melt adhesive previously sprayed thereon and wrapped to make an absorbent member.

The proportion of staple fibers on the skin facing side of the absorbent member was 100%. The proportion of staple fibers on the opposite side was 4%, which seems ascribed to unintentional cutting of the continuous fibers during the processing steps involved.

Comparative Example 1

A hundred parts by weight of opened fluff pulp and 100 parts by weight of an absorbent polymer were uniformly mixed in an air stream and accumulated to make an airlaid fiber layer weighing 520 g/m$^2$ (having 260 g/m$^2$ of the fluff pulp and 260 g/m$^2$ of the absorbent polymer). The resulting airlaid fiber layer was wrapped in tissue paper having a basis weight of 16 g/m$^2$, with 5 g/m$^2$ of a hot-melt adhesive sprayed therebetween, to obtain an absorbent member otherwise in the same manner as in Example 1.

Comparative Example 2

An absorbent member was made in the same manner as in Comparative Example 1, except that 100 parts by weight of opened fluff pulp and 100 parts by weight of an absorbent polymer were uniformly mixed in an air stream and accumulated to make an airlaid fiber layer having a basis weight of 300 g/m$^2$ (having 150 g/m$^2$ of the fluff pulp and 150 g/m$^2$ of the absorbent polymer). An absorbent member was made otherwise in the same manner as in Example 1

Comparative Example 3

An absorbent member was made in the same manner as in Example 1, except that the wrapped laminate was not compressed between rollers, that is, cutting of the fibers was not conducted.

Performance Evaluation:

The absorbent members obtained in Examples and Comparative Examples were evaluated for absorption capacity, structural stability, and pliability in accordance with the following test methods. The results obtained are shown in Table 1 below.

(1) Absorption Capacity

The absorbent member was fixed to an inclined plate set at 45°. A given amount of physiological saline was poured at a given time interval at a position 200 mm below the upper end of the absorbent member. The total amount of physiological saline that had been poured until it began to leak from the lower end of the absorbent member was compared. Taking the absorption capacity of Comparative Example 1 as 1.0, the results were expressed relatively by calculation using formula:

Absorption capacity (relative)=absorption capacity of sample/absorption capacity of Comparative Example 1

(2) Structural Stability (2-1) While Dry

The absorbent member measuring 100 mm by 200 mm was cut at the central portion thereof to prepare a 100 mm×100 mm test piece. The cut piece was given 20 shakes with an amplitude of 5 cm at a rate of one shake per second with the cut edge down. The polymer particles fallen from the cut edge was weighed. The polymer supporting properties of the absorbent member was rated based on the ratio of the fallen polymer as follows.

A: The ratio of the fallen polymer is within 10%.
B: The ratio of the fallen polymer is higher than 10% and not higher than 25%.
C: The ratio of the fallen polymer is higher than 25%.

(2-2) While Wet

A 100 mm by 200 mm cut piece of the absorbent member was almost evenly impregnated with 200 g of physiological saline and then gently lifted to see if the absorbent member broke with the naked eye. Apart from the above evaluation, the fallen absorbent polymer was weighed. The weight was divided by a water retention per unit weight of the absorbent polymer previously determined by a centrifugal dewatering method to obtain the dry weight of the fallen absorbent polymer. The ratio of the fallen absorbent polymer was calculated therefrom relative to the amount of the polymer having been supported. The amount of the absorbent polymer that had been supported was determined as follows. An absorbent member to be analyzed, the weight of which had been measured, was immersed in an aqueous ascorbic acid solution and exposed to sunlight for a sufficient period of time to dissolve the absorbent polymer completely, followed by washing with water. The decomposition of the absorbent polymer and washing of the absorbent member with water were repeated until the absorbent polymer was completely dissolved. The absorbent member was then dried and weighed. The weight of the dried absorbent member was subtracted from the weight of the absorbent member before the absorbent polymer decomposition to estimate the amount of the absorbent polymer that had been present in the absorbent polymer.

A: The ratio of the fallen polymer is 10% or lower. No structural destruction of the absorbent member is observed.
B: The ratio of the fallen polymer is higher than 10% and not higher than 25%. No structural destruction of the absorbent member is observed.
C: The ratio of the fallen polymer is higher than 25%, or structural destruction of the absorbent member is observed.

A: The "handle" is 2N or less.
B: The "handle" is more than 2N and not more than 4N.
C: The "handle" is more than 4N.

(4) Spread Directionality

The absorbent member was placed horizontally, and a fluid was poured on the center of the absorbent member. The spread directionality was expressed by the difference in length of the spread area in the major and the minor axes. Forty grams of a fluid was poured at a rate of 5 g/sec. After 5 minutes from completion of absorption, the lengths of the spread area in the major and the minor axes were measured. In the case where the spreading properties differ between the sites of measurements, for example, between the skin facing surface and the inside or between the middle portion and the side portion of the absorbent member, the measurement was taken on both sites, and the results showing a greater spread directionality (a greater difference between the lengths in the two axes) were taken for rating the spread directionality.

A: The ratio of major axis length to minor axis length is 1.5 or greater.
B: The ratio of major axis length to minor axis length is 1.2 or greater and smaller than 1.5.
C: The ratio of major axis length to minor axis length is 1.0 or greater and smaller than 1.2.

TABLE 1

|  | Example 1 | Example 2 | Example 3 | Comp. Example 1 | Comp. Example 2 | Comp. Example 3 |
|---|---|---|---|---|---|---|
| Structural Characteristics | Continuous fibers are cut. | Same as on the left | Staple fiber web and continuous fiber web are superposed. | Pulp and absorbent polymer are mixed uniformly. | Same as on the left | Continuous fibers are not cut. |
|  | Absorbent polymer is spread on the laterally middle portion. | Absorbent polymer is spread on the laterally middle portion intermittently in the longitudinal direction. | Same as in Example 1 |  |  | Same as in Example 1 |
| Absorption Capacity | 1.0 | 1.0 | 1.0 | 1.0 | 0.6 | 1.0 |
| Structural Stability Dry | A | A | A | A | A | A |
| Structural Stability Wet | A | A | A | A | A | A |
| Pliability | A | A | A | C | A | A |
| Spread Directionality | A | A | A | C | C | A |
| Mode of Absorption | Different between the middle and side portions Middle: uniform spread Sides: longitudinal spread | Different between the middle, side, and front/rear portions Middle, front and rear: uniform spread Side: longitudinal spread | Different between the surface and inside Surface: uniform spread Inside: longitudinal spread | Uniform spread | Uniform spread | Longitudinal spread all over the absorbent member (large spread area causing skin wetting) |

(3) Pliability

Pliability (flexibility) of the absorbent member was evaluated by the use of a handle-o-meter. The smaller the "handle" value as measured with a handle-o-meter, the easier to put on and the snugger the fit. Measurement with a handle-o-meter was carried out as follows in accordance with JIS L1096 (stiffness and softness measuring method). A specimen measuring 50 mm in the width direction and 150 mm in the longitudinal direction was placed on the platform, which has a 60 mm wide slot, with the length perpendicular to the slot. The force required for a 2 mm thick penetrator blade to force the center of the specimen into the slot was read. In the present invention, a handle-o-meter HOM-3 available from Daiei Kagaku Seiki Co., Ltd. was used. The measurement was made on three points to obtain an average. The pliability was rated as follows.

It is seen from above that the absorbent members of Examples exhibit spread directionality or have different spreading properties in different portions thereof.

Example 11

Figure 28A:
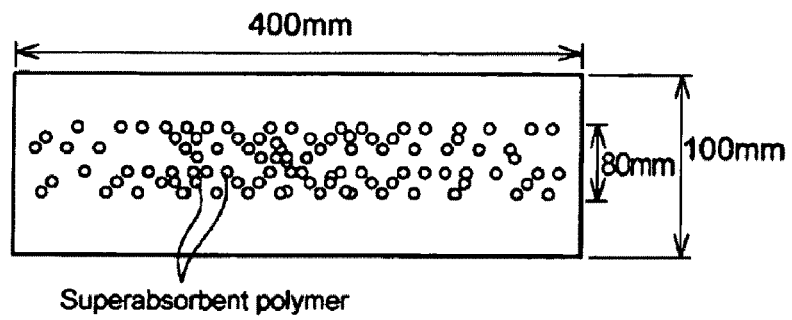
Figure 28B:
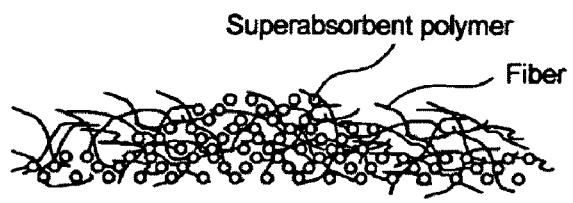
Figure 28C:
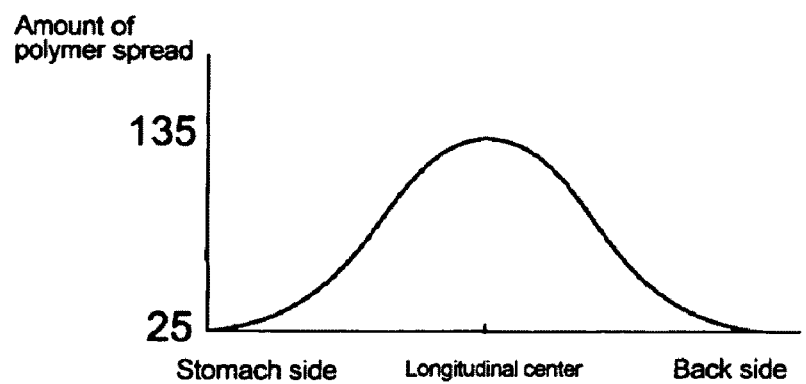

A tow of crimped, continuous cellulose acetate fibers was prepared. The individual continuous fibers had a thickness of 2.1 dtex, and the total linear density of the tow was 25,000 dtex. The tow was fed under tension and opened in an air opening unit. The tow-opened web was passed between a roller having a large number of discs arrayed around its periphery in an axial direction at a given interval and a smooth anvil roller, between which the web was combed. The width of the web was adjusted to 100 mm. The running speed of the web was slowed down, and the web was transferred onto a vacuum conveyor. The web was released from the tension on the vacuum conveyor to develop the crimp. The continuous fibers of the web had a crimp percentage of 30%, and the number of the crimps per centimeter was 15. The fiber interstices in the web were thus broadened to help an absorbent polymer enter and to make the web bulkier thereby to improve polymer supporting capability. In this state, lumpy superabsorbent polymer particles having an average particle size of 350 μm and a bulk density of 0.68 g/cm$^3$ (polyacrylic superabsorbent polymer available from Kao Corp.) were spread on the web over a width of 80 mm and embeddedly supported therein while varying the amount to be spread as shown in FIGS. 28(a) to 28(c). The basis weight of the web was 35 g/m$^2$, and the amount of the absorbent polymer spread was varied continuously within a range of from 25 to 135 g/m$^2$ (see FIG. 28(c)). More specifically, spreading started from the front end (stomach side end) at the lowest basis weight of 25 g/m$^2$, and the amount of the polymer to be spread gradually increased and reached the maximum of 135 g/m$^2$ at 200 mm from the front end and then gradually decreased to the lowest basis weight of 25 g/m$^2$ at the opposite rear end (back side end).

Separately, 100 parts by weight of opened fluff pulp and 100 parts by weight of a superabsorbent polymer were uniformly mixed in an air stream and accumulated on a generally T-shaped frame to obtain an airlaid fiber layer having a basis weight of 300 g/m$^2$. The T-shaped frame was made up of a horizontal portion with a width of 100 mm and a length of 125 mm and a vertical portion with a length of 300 mm and a width of 70 mm in the crotch section thereof (to a length of 100 mm from the horizontal portion) and 100 mm in the rest thereof. The airlaid fiber layer contained 150 g/m$^2$ of the fluff pulp and 150 g/m$^2$ of the superabsorbent polymer. The web was superposed on the airlaid fiber layer, and the resulting laminate was wrapped in tissue paper having a basis weight of 16 g/m$^2$ on which a hot-melt adhesive had been sprayed. The wrapped laminate was compressed between a metal roller and a rubber roller having a clearance of 0 mm therebetween, whereby the constituting fibers of the web were cut by the superabsorbent polymer particles, and the web and the tissue paper were united to provide an absorbent member.

The tissue paper was stripped off the skin facing side of the resulting absorbent member, and the length of the fibers was determined in accordance with the method described above. The fibers were classified into the first to fourth groups using the criteria according to the first aspect of the invention. The found proportions of the fibers classified in the four groups were as follows.
Fibers classified as 1st group (fiber length of less than 100 mm): 10%
Fibers classified as 2nd group (fiber length of 100 mm or longer and shorter than 200 mm): 30%
Fibers classified as 3rd group (fiber length of 200 mm or longer and shorter than 300 mm): 43%
Fibers classified as 4th group (fiber length of 300 mm or loner): 17%

Example 12

Figure 29A:
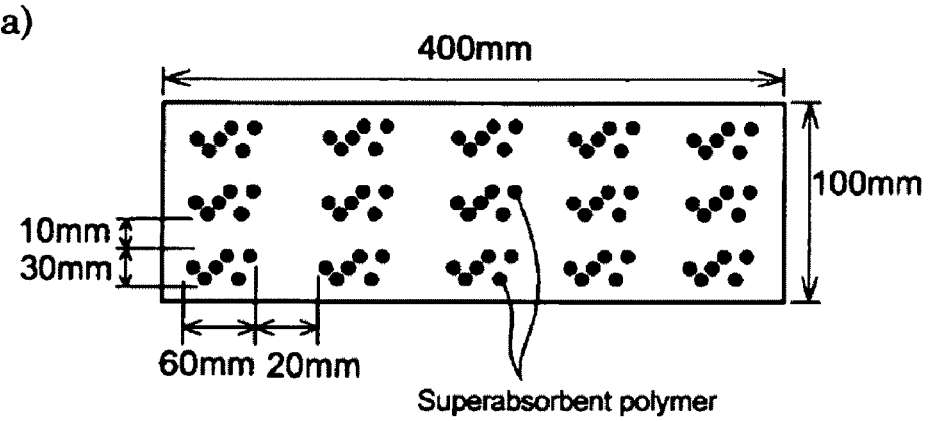
Figure 29B:
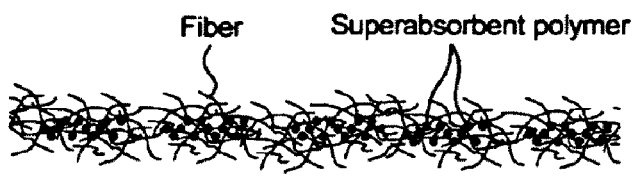
Figure 29C:
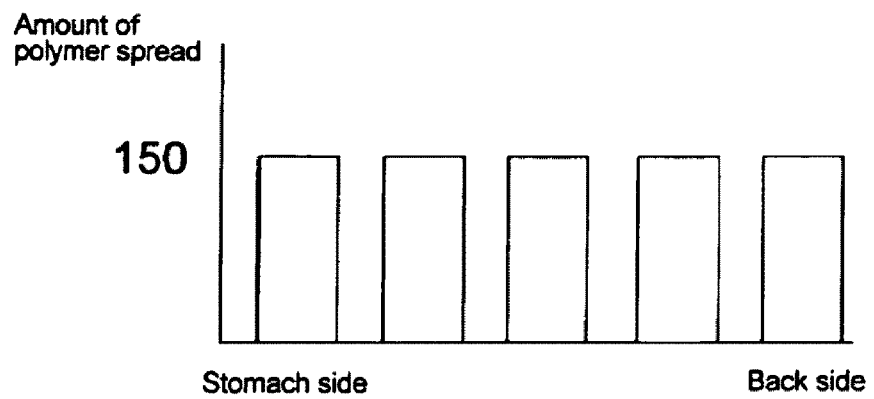

A tow-opened web having a superabsorbent polymer embedded therein was prepared in the same manner as in Example 11, except that the pattern of spreading was changed as illustrated in FIG. 29 and that the amount of the polymer spread per m$^2$ was 150 g. The pattern was composed of a plurality of units each measuring 30 mm in width direction of the web and 60 mm in length direction of the web arranged at a 20 mm spacing in the longitudinal direction and a 10 mm spacing in the width direction. Separately, fluff pulp was accumulated within a generally T-shaped frame having the same geometry as in Example 11 to make an airlaid fiber layer weighing 100 g/m$^2$. The web was superposed on the airlaid fiber layer, and the laminate was wrapped in a hydrophilized SMMS nonwoven fabric having a basis weight of 16 g/m$^2$. The wrapped laminate was compressed between a metal roller and a rubber roller in the same manner as in Example 11 to cut the fibers constituting the web by the superabsorbent polymer particles.

The fibers of the resulting absorbent member were classified according to the same criteria as used in Example 11. The proportion of the fibers classified in each group is shown in Table 2.

Example 13

A web was prepared in the same manner as in Example 11. After adjusting the width to 100 mm, the web was passed between two sets of gears having different pitches to cut the fibers twice. After the running speed of the web was slowed down, the web was processed in the same manner as in Example 11. The fibers of the resulting absorbent member were classified in the same manner as in Example 11. The proportion of the fibers classified in each group is shown in Table 2.

Separately, 100 parts by weight of fluff pulp and 100 parts by weight of the superabsorbent polymer were uniformly mixed in an air stream and accumulated within a T-shaped frame to make an airlaid fiber layer weighing 300 g/m$^2$ (the same as the one used in Example 11). The airlaid fiber layer was superposed on tissue paper having a basis weight of 16 g/m$^2$ and having a hot-melt adhesive previously sprayed thereto.

Comparative Example 11

A hundred parts by weight of opened fluff pulp and 100 parts by weight of a superabsorbent polymer were uniformly mixed in an air stream and accumulated to make an airlaid fiber layer weighing 520 g/m$^2$, in which the basis weights of the fluff pulp and the superabsorbent polymer were both 260 g/m$^2$. The resulting airlaid fiber layer was wrapped in tissue paper having a basis weight of 16 g/m$^2$ and having 5 g/m$^2$ of a hot-melt adhesive previously sprayed thereto. The fibers had an average length of 3 mm.

Comparative Example 12

An airlaid fiber layer having a basis weight of 300 g/m$^2$ was prepared by uniformly mixing 100 parts by weight of opened fluff pulp and 100 parts by weight of a superabsorbent polymer in an air stream in the same manner as in Comparative Example 11. The basis weights of the fluff pulp and the superabsorbent polymer were both 150 g/m$^2$. An absorbent member was made in otherwise the same manner as in Comparative Example 11. The fiber length was 3 mm in average.

Comparative Example 13

An absorbent member was made in the same manner as in Example 11, except that cutting of the fibers by compression between rollers was not carried out, so that the resulting absorbent member might contain substantially no stable fibers.

Performance Evaluation:

The absorbent members obtained in Examples and Comparative Examples were evaluated for absorption capacity and surface flow distance in accordance with the test methods described below. They were also evaluated for structural stability and pliability in accordance with the methods described above. Additionally, the spread area on the absorbent member surface was measured as follows. The results obtained are shown in Table 2.

were processed using image processing software (Image-Pro Plus from Media Cybernetics, Inc.) to obtain a spread area. The spread area was expressed relative to that of Comparative Example 11. The spread area on the absorbent member surface was adopted for evaluation, taking influences to the skin of a wearer into consideration.

TABLE 2

|  | Example 11 | Example 12 | Example 13 | Comp. Example 11 | Comp. Example 12 | Comp. Example 13 |
|---|---|---|---|---|---|---|
| Structural Characteristics | Core layer: web having absorbent polymer supported therein in varying amount Another layer: pulp/absorbent polymer airlaid fiber layer | Core layer: web having absorbent polymer spread in specific pattern at constant basis area Another layer: pulp/absorbent polymer airlaid fiber layer | Same as in Example 11, except that the web fibers are cut by gears. | Pulp/absorbent polymer uniformly mixed airlaid fiber layer | Same as on the left | Same as in Example 11, but the web fibers are not cut. |
| Absorption Capacity | 1.0 | 1.0 | 1.0 | 1.0 | 0.6 | 0.6 |
| Surface Flow Distance (mm) | 73 | 65 | 58 | 64 | 130 | 110 |
| Thickness (mm) | 2.2 | 1.9 | 2.1 | 4.3 | 2.6 | 2.2 |
| Fiber Proportion 1st Group | 10 | 30 | 37 | 3 mm on average | 3 mm on average | — |
| 2nd Group | 30 | 47 | 47 | — | — | — |
| 3rd Group | 43 | 11 | 13 | — | — | — |
| 4th Group | 17 | 12 | 3 | — | — | ≈100 |
| Structural Stability Dry | A | A | A | A | A | A |
| Wet | A | A | A | A | A | A |
| Pliability | A | A | A | C | A | A |
| Spread Area on Absorbent Member Surface (relative to Comp. Example 1) | 0.75 | 0.80 | 0.75 | 1.00 | 1.75 | 1.30 |
| Mode of Absorption | spread inside the absorbent member with small spread area on the surface | partial swell, resulting in reduced contact area with skin | similar to Example 11 | uniform spread | uniform spread but with a large spread area to wet a large area of skin | longitudinal spread all over the absorbent member (large spread area to wet a large area of skin) |

(1) Absorption Capacity and Surface Flow Distance

The absorbent member was fixed to an inclined plate set at 45°. A given amount of physiological saline was poured at a given time interval at a position 200 mm below the upper end of the absorbent member. The total amount of physiological saline that had been poured until it began to leak from the lower end of the absorbent member was compared. Taking the absorption capacity of Comparative Example 11 as 1.0, the results were expressed relatively by calculation using formula:

Absorption capacity (relative)=absorption capacity of sample/absorption capacity of Comparative Example 11

For every pour of saline, the distance the liquid flowed on the surface of the absorbent member was measured to obtain an average. When the distance of liquid flow changed during absorption, the maximum distance was measured. The larger the absorption capacity, the higher the performance. The shorter the flow distance, the higher the downward wicking properties.

(2) Spread Area on Absorbent Member Surface

After 5 minutes following pouring of a liquid, the outline of the liquid spread on the surface of the absorbent member was traced on a transparent sheet. In the case where the spread on the surface of the absorbent member (the spread on the tissue paper in the case of Examples and Comparative Examples) and that inside the absorbent member are different, both the spread areas were recorded. If desired, the resulting images Example 21

A tow of crimped, continuous cellulose acetate fibers was prepared. The individual continuous fibers had a thickness of 2.1 dtex, and the total linear density of the tow was 25,000 dtex. The tow was fed under tension and opened in an air opening unit. The tow-opened web was passed between a roller having a large number of discs arrayed around its periphery in an axial direction at a given interval and a smooth anvil roller, between which the web was combed. The width of the web was adjusted to 100 mm, and the web was passed between a set of gears to cut the fibers in the laterally middle portion of the web (the 15 mm wide strip along each edge was left intact). After the running speed of the web was slowed down, the web was transferred onto a vacuum conveyor. The web was released from the tension on the vacuum conveyor to develop the crimp. The continuous fibers of the web had a crimp percentage of 30%, and the number of the crimps per centimeter was 15. The fiber interstices in the web were thus broadened to help an absorbent polymer enter and to make the web bulkier thereby to improve polymer supporting capability. In this state, lumpy superabsorbent polymer particles having an average particle size of 350 μm and a bulk density of 0.68 g/cm$^3$ (polyacrylic superabsorbent polymer available from Kao Corp.) were spread on the web over a width of 80 mm and embeddedly supported therein. The basis weight of the web was 25 g/m$^2$, and the amount of the absorbent polymer spread was 132 g/m$^2$.

Separately, 100 parts by weight of opened fluff pulp and 100 parts by weight of an superabsorbent polymer were uniformly mixed in an air stream and accumulated on a generally T-shaped frame to obtain an airlaid fiber layer having a basis weight of 300 g/m². The T-shaped frame was made up of a horizontal portion with a width of 100 mm and a length of 125 mm and a vertical portion with a length of 300 mm and a width of 70 mm in the crotch section thereof (to a length of 100 mm from the horizontal portion) and 100 mm in the rest thereof. The airlaid fiber layer contained 150 g/m² of the fluff pulp and 150 g/m² of the absorbent polymer. The web was superposed on the airlaid fiber layer, and the resulting laminate was wrapped in tissue paper having a basis weight of 16 g/m² on which a hot-melt adhesive had been sprayed. The wrapped laminate was compressed between a metal roller and a rubber roller having a clearance of 0 mm therebetween to unite the web and the tissue paper.

The fluff pulp/superabsorbent polymer mixed airlaid fiber layer was removed from the resulting absorbent member, and the degree of orientation of the web containing the continuous fibers and staple fibers was determined in accordance with the method described above. As a result, the degree of orientation was found to be 1.34. The staple fibers were localized in the 80 mm wide, laterally middle portion of the web, i.e., the portion where the superabsorbent polymer had been spread. The proportion of the staple fibers in the laterally middle portion of the web was 86% (the proportion of the continuous fibers was 14%), while that in the side portions was 18%. The distribution of the staple and the continuous fibers was measured as follows.

Method of Measuring Fiber Distribution:

A hundred fibers were randomly drawn from the skin facing side of the longitudinally middle portion of the absorbent member, and their lengths were measured in accordance with the mean fiber length measurement method (method C) specified in JIS L1015. The data were plotted into a histogram. The proportion of the fibers shorter than 70 mm was calculated from the histogram to give the proportion of the staple fibers.

An air-through nonwoven fabric having a basis weight of 25 g/m² was used as a topsheet. The air-through nonwoven fabric was made of linear low density polyethylene sheath/polypropylene core conjugate fibers (thickness: 2.3 dtex; having been hydrophilized with a surface active agent to have liquid permeability). A composite of a porous film weighing 20 g/m² and a spun-bonded polypropylene nonwoven fabric weighing 20 g/m², bonded with 1.5 g/m² of a hot melt adhesive, was used as a backsheet. The porous film was produced by blown-film extruding a uniform mixture of 100 parts by weight of linear low density polyethylene (density: 0.925 g/cm³), 150 parts by weight of calcium carbonate, and 4 parts by weight of an ester compound as a third component and longitudinally stretching the blown film to double the length. A disposable diaper was assembled in otherwise the same manner as commonly used in the manufacture of disposable diapers. The absorbent member was disposed with the orientation direction of the web coinciding with the longitudinal direction of the diaper and with the continuous fiber web side facing the skin of a wearer.

Example 22

A tow-opened web having an absorbent polymer embedded therein was prepared in the same manner as in Example 21, except that the polymer was spread intermittently. Specifically, the polymer was spread on a laterally middle portion of the web having a width of 80 mm and extending from a position 100 mm away from the front edge to a position 350 mm away from the front edge (over an area of 80 mm in the web width direction by 250 mm in the web length direction). The web was passed between a set of gears to cut the fibers in the laterally middle portion of the web (the 15 mm wide strip along each edge was left intact). Opened fluff pulp was airlaid in a generally T-shaped frame having the same geometry as that used in Example 21 to make an airlaid fiber layer having a basis weight of 100 g/m². The web was superposed on the airlaid fiber layer, and the laminate was wrapped in a hydrophilized SMMS nonwoven fabric having a basis weight of 16 g/m². The wrapped laminate was compressed between a metal roller and a rubber roller in the same manner as in Example 21.

The fluff pulp/superabsorbent polymer mixed layer was removed from the resulting absorbent member, and the degree of orientation of the web containing the continuous fibers and staple fibers was determined in accordance with the method described above. As a result, the degree of orientation was found to be 1.29. The proportion of the staple fibers in the region where the superabsorbent polymer had been spread was 78% (the proportion of the continuous fibers was 22%), while that in the regions where the polymer was not spread was 12%. A disposable diaper was made otherwise in the same manner as in Example 21.

Example 23

A web (designated web P1) having a superabsorbent polymer embedded therein was prepared in the same manner as in Example 21. The web P1 had a degree of fiber orientation of 1.41. Bicomponent conjugate fibers having a polyethylene sheath and a polypropylene core (3.3 dtex, 51 mm, having been surface treated with a surface active agent to have hydrophilic properties and antistatic properties) were carded to make a web (designated web P2) having a basis weight of 30 g/m². The web P2 was treated with 135° C. hot air to fuse-bond the fibers to one another and, as longitudinally stretched between sets of rollers having different rotating speeds, superposed on the web P1 having the absorbent polymer embedded therein.

Separately, 100 parts by weight of fluff pulp and 100 parts by weight of a superabsorbent polymer were uniformly mixed in an air stream and accumulated within a T-shaped frame to make an airlaid fiber layer weighing 300 g/m² (the same as the one used in Example 21). The airlaid fiber layer was superposed on tissue paper having a basis weight of 16 g/m² and having a hot-melt adhesive previously sprayed thereto. The above prepared laminate of P1 and P2 was superposed thereon. On the resulting stack of fiber layers, was superposed another tissue paper having a basis weight of 16 g/m² and having a hot-melt adhesive previously sprayed thereon and wrapped to make an absorbent member.

The P1/P2 laminate had a degree of fiber orientation of 1.33. The proportion of staple fibers on the skin facing side of the absorbent member was 100%. The proportion of staple fibers on the opposite side was 4%, which seems ascribed to unintentional cutting of the continuous fibers during the processing steps involved. The resulting absorbent member was assembled into a disposable diaper with the web P1 being adopted to face the skin of a wearer. A disposable diaper was made otherwise in the same manner as in Example 21.

Comparative Example 21

A hundred parts by weight of opened fluff pulp and 100 parts by weight of a superabsorbent polymer were uniformly mixed in an air stream and accumulated to make an airlaid fiber layer having a basis weight of 520 g/m² (having 260 g/m² of the fluff pulp and 260 g/m² of the superabsorbent polymer). The resulting airlaid fiber layer was wrapped in tissue paper having a basis weight of 16 g/m², with 5 g/m² of a hot-melt adhesive sprayed therebetween, to obtain an absorbent member. The resulting absorbent member had a total basis weight of 562 g/m², a thickness of 4.3 mm, and a degree of fiber orientation of 1.05. A disposable diaper was made otherwise in the same manner as in Example 21.

Comparative Example 22

An absorbent member was made in the same manner as in Comparative Example 21, except that 100 parts by weight of opened fluff pulp and 100 parts by weight of a superabsorbent polymer were uniformly mixed in an air stream and accumulated to make an airlaid fiber layer having a basis weight of 300 g/m² (having 150 g/m² of the fluff pulp and 150 g/m² of the absorbent polymer). An absorbent member was made otherwise in the same manner as in Comparative Example 1. The resulting absorbent member had a total basis weight of 342 g/m² and a thickness of 2.6 mm. A disposable diaper was made otherwise in the same manner as in Example 21. The fibers in the absorbent member had a degree of orientation of 1.10.

Comparative Example 23

An absorbent member was made in the same manner as in Example 21, except that the wrapped laminate was not compressed between rollers, that is, cutting of the fibers was not conducted so that the resulting absorbent member might contain substantially no staple fibers. A disposable diaper was made otherwise in the same manner as in Example 21.

Performance Evaluation:

The absorbent members obtained in Examples and Comparative Examples were evaluated for absorption capacity and surface flow distance in the same manner as described above. The absorption capacity was relatively expressed, taking the absorption capacity of Comparative Example 21 as 1.0. In addition, the absorbent members were evaluated for structural stability and pliability in the same manner as described above. The results obtained are shown in Table 3 below.

TABLE 3

| | Example 21 | Example 22 | Example 23 | Comp. Example 21 | Comp. Example 22 | Comp. Example 23 |
|---|---|---|---|---|---|---|
| Structural Characteristics | Continuous fibers are cut. | Same as on the left | Staple fiber web and continuous fiber web are superposed. | Pulp and absorbent polymer are mixed uniformly. | Same as on the left | Continuous fibers are not cut. |
| | Absorbent polymer is spread in the laterally middle portion. | Absorbent polymer is intermittently spread in the longitudinal direction in the laterally middle portion. | Same as in Example 21 | | | Same as in Example 21 |
| Absorbent Member Thickness (mm) | 2.2 | 2.2 | 2.4 | 3.7 | 2.0 | 2.2 |
| Degree of Orientation of Total Web | 1.34 | 1.29 | 1.33 | 1.05 | 1.10 | 1.34 |
| Degree of Orientation of Staple Fibers of Web | 1.32 (in the middle portion of absorbent member) | Same as on the left | 1.18 | 1.05 | 1.10 | — |
| Degree of Orientation of Continuous Fibers of Web | 1.35 (in the side portions of absorbent member) | Same as on the left | 1.41 | — | — | 1.37 |
| Absorption Capacity (relative to Comp. Example 1) | 1.0 | 1.0 | 1.0 | 1.0 | 0.6 | 1.0 |
| Surface Flow Distance (mm) | 73 | 65 | 48 | 64 | 130 | 100 |
| Spread Directionality | A | A | A | C | C | A |
| Mode of Absorption | Different between the middle and side portions Middle: uniform spread Side: longitudinal spread | Different between the middle, the side, and the front/rear portions Middle, front and rear: uniform spread Side: longitudinal spread | Different between the surface and the inside Surface: uniform spread Inside: longitudinal spread | Uniform spread | Uniform spread | Longitudinal spread all over the absorbent member (large spread area to cause skin wetting) |

Example 31

A tow of crimped, continuous cellulose acetate fibers was prepared. The individual continuous fibers had a thickness of 2.1 dtex, and the total linear density of the tow was 25,000 dtex. The tow was fed under tension and opened in an air opening unit. The tow-opened web was passed between a roller having a large number of discs arrayed around its periphery in an axial direction at a given interval and a smooth anvil roller, between which the web was combed. The width of the web was adjusted to 100 mm. The running speed of the web was slowed down, and the web was transferred onto a vacuum conveyor. The web was released from the tension on the vacuum conveyor to develop the crimp. The continuous fibers of the web had a crimp percentage of 30%, and the number of the crimps per centimeter was 15. Lumpy absorbent polymer particles (IM930, available from San-Dia Polymers, Ltd.) were spread on a 70 mm wide, laterally middle portion of the web in an amount of 130 g/m² to obtain a first web p1 having the polymer particles embeddedly supported therein.

The same procedures were repeated to make a second web p2. The first web p1 and the second web p2 were superposed on each other with a fluff pulp layer having a basis weight of 50 g/m² interposed therebetween. A fluff pulp layer having a basis weight of 100 g/m² was disposed beneath the second web p2. The second web and the two fluff pulp layers had the same width as the first web (100 mm).

The stack of the fiber layers was wrapped in tissue paper having a basis weight of 16 g/m² on which 5 g/m² of a hot-melt adhesive had been sprayed to obtain an absorbent member p3 in which the fluff pulp layer with a basis weight of 100 g/m² was located farthest from the skin. The absorbent member weighed 390 g/m² and was 2.2 mm thick. The basis weight of each tow-opened web was 13 g/m². The absorbent member p3 was passed through a set of smooth rollers, one made of an elastic material, and the other a hard material, to cut the continuous fibers present in a 70 mm wide, laterally middle portion of the absorbent member into staple fibers. The absorbent member was then heat embossed between a heated embossing roller having a large number of projections on its peripheral surface and a smooth backup roll to bond the staple fibers of continuous fiber origin to one another. The projections of the embossing roller were 0.5 cm diameter circles arranged in a staggered pattern at spacing of 0.5 cm.

The absorbent member was evaluated assuming that the orientation direction of the webs coincided with the longitudinal direction of a diaper.

Example 32

An absorbent member was obtained in the same manner as in Example 31 with the following exception. A web p1 having absorbent polymer particles embeddedly supported therein was prepared in the same manner as in Example 31, except that the amount of the absorbent polymer spread was 110 g/m². A hundred parts by weight of opened fluff pulp and 100 parts by weight of an absorbent polymer were uniformly mixed in an air stream and accumulated to make a mixed fiber layer having a basis weight of 300 g/m² (having 150 g/m² of the fluff pulp and 150 g/m² of the absorbent polymer). The mixed fiber layer was superposed on the web p1, and the laminate was wrapped in a hydrophilized spunbonded-meltblown-spunbonded (SMS) nonwoven fabric having a basis weight of 16 g/m². The resulting absorbent member had a basis weight of 362 g/m² and a thickness of 2 mm.

Example 33

An absorbent member was obtained in the same manner as in Example 32, except that the web was prepared from a tow of continuous fibers having an individual thickness of 6.7 dtex and a total linear density of 17,000 dtex, and that the continuous fibers of the web had a crimp percentage of 24% and 10 crimps per cm. The web had a basis weight of 30 g/m².

Comparative Example 31

An absorbent member was obtained in the same manner as in Example 31 with the following exception. A hundred parts by weight of opened fluff pulp and 100 parts by weight of an absorbent polymer were uniformly mixed in an air stream and accumulated to make an airlaid fiber layer having a basis weight of 520 g/m² (having 260 g/m² of the fluff pulp and 260 g/m² of the absorbent polymer). The resulting airlaid fiber layer was wrapped in tissue paper having a basis weight of 16 g/m², with 5 g/m² of a hot-melt adhesive sprayed therebetween to unite them together.

Comparative Example 32

An absorbent member was obtained in the same manner as in Comparative Example 31, except that 100 parts by weight of opened fluff pulp and 100 parts by weight of an absorbent polymer were uniformly mixed in an air stream and accumulated to make an airlaid fiber layer having a basis weight of 300 g/m² (having 150 g/m² of the fluff pulp and 150 g/m² of the absorbent polymer). An absorbent member was obtained otherwise in the same manner as in Example 31.

Comparative Example 33

An absorbent member was prepared in the same manner as in Example 31, except the compression between rollers, i.e., cutting of the fibers was not conducted.

Performance Evaluation:

The absorbent members obtained in Examples and Comparative Examples were evaluated for absorption capacity, structural stability, and pliability in accordance with the methods described below.

(1) Absorption Capacity

Measurement was made in accordance with the method previously described, provided that the results were relatively expressed, taking the absorption capacity of Comparative Example 31 as 1.0.

(2) Structural Stability (2-1) While Dry

Measured in accordance with the method described above.

(2-2) While Wet

Measured in accordance with the method described above.

(2-3) Wet Break Strength

A 70 mm by 100 mm cut piece of the absorbent member (the length of the piece coincide with the longitudinal direction of the absorbent member) was impregnated with 1.0 g of physiological saline per 1.0 cm² of the cut piece. After completion of absorption by the absorbent polymer (after the surface of the absorbent member generally turned white), the piece was clamped at their ends by the jaws of a Tensilon tester (RTC-1150A from Orientec Co., Ltd.) and pulled at a rate of 300 mm/min to measure the breaking strength. Five pieces per sample were tested to obtain an average. Before the pulling, the paper carrier sheet was cut with, e.g., a cutter knife to exclude the influence of the strength of the paper carrier sheet.

(3) Surface Spreading Properties

A liquid was poured into the center of a horizontally placed absorbent member having a topsheet overlaid thereon, and the spread of the liquid on the topsheet surface was examined. Specifically, 40 g of a liquid was poured at a rate of 5 g/sec. After 5 minutes from completion of absorption, the outline of the liquid spread was traced on a transparent sheet, and the spread area was obtained by image processing. In the case where the spreading behavior differed from portion to portion, for example, between the skin facing surface and inside the absorbent member or between the middle and the side portions of the absorbent member, the spread area on the skin facing surface was recorded. The measured spread area was divided by that of the absorbent member of Comparative Example 31 to give a relative value taking the value of Comparative Example 31 as 1.0. When the relative value exceeded 1.0, the spread area was regarded as being wider. The criteria of rating are as follows.

A: The spread area is 0.8 or less relative to the value of Comparative Example 31.

B: The spread area is more than 0.8 and less than 1.0 relative to the value of Comparative Example 31.

C: The spread area is 1.0 or more relative to the value of Comparative Example 31 (indicating that the spreading properties are equal to or larger than that of Comparative Example 31).

TABLE 4

|  | Example 31 | Example 32 | Example 33 | Comp. Example 31 | Comp. Example 32 | Comp. Example 33 |
| --- | --- | --- | --- | --- | --- | --- |
| Structural Characteristics | Two webs are superposed with SAP supported therebetween. | One web | Fiber thickness is changed (2.1→6.7 dtex) | Pulp and absorbent polymer are uniformly mixed. | Same as on the left | Continuous fibers are not cut. |
| Absorption Capacity | 1.0 | 1.0 | 1.0 | 1.0 | 0.6 | 1.0 |
| Thickness (mm) | 2.2 | 1.9 | 2.1 | 3.7 | 2.0 | 2.2 |
| Structural Stability  Dry | A | A | A | A | A | A |
| Structural Stability  Wet | A | A | A | A | A | A |
| Breaking Strength (cN/70 mm) | >1000 | >1000 | >1000 | 200 | 70 | >1000 |
| Pliability | A | A | A | C | A | A |
| Spread Area on Absorbent Member Surface | 0.75 A | 0.80 A | 0.75 A | 1.00 B | 1.50 C | 1.20 C |
| Mode of Absorption | Small spread area on the surface, large spread in the inside | Same as on the left | Same as on the left | Uniform spread | Uniform spread but with a large spread area to wet a large area of skin | longitudinal spread all over the absorbent member (large spread area to wet a large area of skin) |

Note:
The structural characteristics of Examples 32 and 33 shown in Table 4 are alterations to Example 31.

It is seen from Table 4 that the absorbent members of Examples exhibit spread directionality or different spreading properties in different portions thereof.

INDUSTRIAL APPLICABILITY

The absorbent member of the present invention is pliable, excellent in absorbing performance, capable of controlling the spread of a fluid to efficiently prevent leakage, and yet easy to produce. The production method of the invention produces such an absorbent member efficiently.

The absorbent member of the first and second aspects of the invention are pliable, excellent in downward wicking properties, and resistant to destruction and bunching by an outer force imposed during use. The production method of the invention produces such an absorbent member efficiently.

The absorbent member of the third aspect of the invention is capable of controlling the spread of a fluid to efficiently prevent leakage.

The invention claimed is:

1. An absorbent member comprising a fiber aggregate containing continuous fibers and synthetic or semisynthetic staple fibers and lumpy particles;
   wherein the absorbent member comprises a middle region and two side regions;
   wherein the continuous fibers are located in the side regions, the lumpy particles are located in the middle region, and the staple fibers are located only in the middle region;
   wherein the continuous fibers are oriented in the longitudinal direction of the absorbent member; and
   wherein the staple fibers in the middle region are formed by cutting continuous fibers.

2. The absorbent member according to claim 1, wherein the continuous fibers and the staple fibers are in a mixed state.

3. The absorbent member according to claim 1, further comprising an absorbent polymer, the absorbent polymer being localized in a specific site in a planar direction or a thickness direction of the absorbent member.

4. The absorbent member according to claim 1, wherein the lumpy particles are localized in a specific site in a planar or thickness direction of the absorbent member, and the lumpy particles are present in the same site as the staple fibers.

5. The absorbent member according to claim 1, wherein the fiber aggregate containing continuous fibers and synthetic or semisynthetic staple fibers has its constituent fibers not bonded to one another.

6. An absorbent article comprising the absorbent member according to claim 1, the staple fibers being present in a zone adapted to face a point of discharge of a wearer during use of the absorbent article.

7. A method of producing the absorbent member according to claim 1, comprising the steps of providing a web of continuous fibers and pressing a cutting member having randomly arranged cutting projections onto the web to cut the continuous fibers into a variety of lengths.

8. An absorbent member comprising a web of continuous fibers and lumpy particles held in the web,
   the continuous fibers in at least part of a region where the particles are distributed in a planar direction of the web have been cut into a plurality of staple fibers;
   wherein the absorbent member comprises a middle region and two side regions;
   wherein the continuous fibers are located in the side regions, the lumpy particles are located in the middle region, and the staple fibers are located only in the middle region; and
   wherein the continuous fibers are oriented in the longitudinal direction of the absorbent member.

9. A method of producing an absorbent member having a web of continuous fibers and lumpy particles held in the web, wherein the continuous fibers in part of the web have been cut into a plurality of staple fibers, the method comprising the steps of:
   spreading lumpy particles on a web of hydrophilic continuous fibers to provide a region with the particles spread and
   pressing at least part of the region in its thickness direction to press the continuous fibers in the at least part of the region onto the particles to cut the continuous fibers;

wherein the absorbent member comprises a middle region and two side regions;

wherein the continuous fibers are located in the side regions, the lumpy particles are located in the middle region, and the staple fibers are located only in the middle region; and wherein the continuous fibers are oriented in the longitudinal direction of the absorbent member.

* * * * *